(12) United States Patent
Chamberlain et al.

(10) Patent No.: US 12,421,285 B2
(45) Date of Patent: Sep. 23, 2025

(54) MICRO-DYSTROPHINS AND RELATED METHODS OF USE

(71) Applicant: University of Washington, Seattle, WA (US)

(72) Inventors: Jeffrey S. Chamberlain, Seattle, WA (US); Julian Ramos, Seattle, WA (US); Stephen D. Hauschka, Seattle, WA (US)

(73) Assignee: University of Washington, Seattle, WA (US)

( * ) Notice: Subject to any disclaimer, the term of this patent is extended or adjusted under 35 U.S.C. 154(b) by 1531 days.

(21) Appl. No.: 16/593,840

(22) Filed: Oct. 4, 2019

(65) Prior Publication Data

US 2020/0031890 A1    Jan. 30, 2020

Related U.S. Application Data

(62) Division of application No. 15/541,870, filed as application No. PCT/US2016/013733 on Jan. 15, 2016, now Pat. No. 10,479,821.

(60) Provisional application No. 62/104,537, filed on Jan. 16, 2015.

(51) Int. Cl.
| | |
|---|---|
| *C07K 14/47* | (2006.01) |
| *A61K 38/00* | (2006.01) |
| *A61K 48/00* | (2006.01) |
| *A61P 21/00* | (2006.01) |
| *C07H 21/04* | (2006.01) |
| *C12N 15/85* | (2006.01) |
| *C12N 15/86* | (2006.01) |

(52) U.S. Cl.
CPC ...... *C07K 14/4708* (2013.01); *A61K 48/0058* (2013.01); *A61P 21/00* (2018.01); *C07H 21/04* (2013.01); *C07K 14/4707* (2013.01); *C07K 14/4716* (2013.01); *C12N 15/85* (2013.01); *C12N 15/86* (2013.01); *A61K 38/00* (2013.01); *C07K 2319/30* (2013.01); *C12N 2750/14143* (2013.01); *C12N 2830/008* (2013.01)

(58) Field of Classification Search
None
See application file for complete search history.

(56) References Cited

U.S. PATENT DOCUMENTS

| | | |
|---|---|---|
| 7,906,111 B2 | 3/2011 | Wilson et al. |
| 10,166,272 B2 | 1/2019 | Dickson et al. |
| 2007/0202587 A1 | 8/2007 | Hwang et al. |
| 2008/0044393 A1 | 2/2008 | White et al. |
| 2008/0167260 A1 | 7/2008 | Chamberlain et al. |
| 2008/0249052 A1 | 10/2008 | Duan et al. |
| 2011/0229971 A1 | 9/2011 | Knop et al. |
| 2013/0136729 A1 | 5/2013 | French et al. |
| 2014/0234255 A1 | 8/2014 | Lai et al. |
| 2015/0329609 A1 | 11/2015 | Acharjee |
| 2016/0186139 A1 | 6/2016 | Regnier et al. |

FOREIGN PATENT DOCUMENTS

| | | |
|---|---|---|
| CN | 107250364 A | 10/2017 |
| EP | 3245291 A2 | 11/2017 |
| HK | 1238297 B | 4/2018 |
| IN | 201717024223 A | 10/2017 |
| JP | 20100516252 | 5/2010 |
| JP | 2018503374 A5 | 2/2018 |
| WO | 2008088895 A3 | 7/2008 |
| WO | 2016115543 A | 7/2016 |

OTHER PUBLICATIONS

Himeda CL, Chen X, Hauschka SD. Design and testing of regulatory cassettes for optimal activity in skeletal and cardiac muscles. Methods Mol Biol. 2011;709:3-19. doi: 10.1007/978-1-61737-982-6_1. PMID: 21194018. (Year: 2011).*

Lai et al., "Dystrophins carrying spectrin-like repeats 16 and 17 anchor nNOS to the sarcolemma and enhance exercise performance in a mouse model of muscular dystrophy." J. Clin. Invest. 119(3):624-635 (2009).

International Search Report and Written Opinion dated Jul. 28, 2016 as received in International Application No. PCT/US2016/013733.

Kobayashi et al. "Sarcolemma-Localized nNOS is Required to Maintain Activity after Mild Exercise" Nature 456, (7221.),511-515, (2008).

Matari et al. "Partial Rescue of Growth Failure in Growth Hormone (GH)-Deficient Mice by a Single Injection of a Double-Stranded Adeno-Associated Viral Vector Expressing the GH Gene Driven by a Muscle-Specific Regulatory Cassette", Human Gene Therapy 20: 759-766 (2009).

Gonçalves, Manuel AFV, et al. "Transcription factor rational design improves directed differentiation of human mesenchymal stem cells into skeletal myocytes." Molecular Therapy 19.7 (2011): 1331-1341.

(Continued)

*Primary Examiner* — Allison M Fox
*Assistant Examiner* — Alyssa G Weston
(74) *Attorney, Agent, or Firm* — Nixon Peabody LLP; Mark J. FitzGerald; Alissa R. Young

(57) ABSTRACT

Nucleotide sequences including a micro-dystrophin gene are provided. The micro-dystrophin genes may be operatively linked to a regulatory cassette. Methods of treating a subject having, or at risk of developing, muscular dystrophy, sarcopenia, heart disease, or cachexia are also provided. The methods may include administering a pharmaceutical composition including the micro-dystrophin gene and a delivery vehicle to a subject. Further, the methods may include administering the pharmaceutical composition a subject having Duchenne muscular dystrophy or Becker muscular dystrophy.

6 Claims, 32 Drawing Sheets
Specification includes a Sequence Listing.

(56) References Cited

OTHER PUBLICATIONS

Zhang et al., "Novel mini-dystrophin gene dual adeno-associated virus vectors restore neuronal nitric oxide synthase expression at the sarcolemma", Human Gene Therapy, 23, (1.), 98-103, (2012).
Abmayr et al. "Chapter 2—The Structure and Function of Dystrophin" Molecular Mechanisms of Muscular Distrophies (2005).
Banks et al. "Molecular and Cellular Adaptations for Chronic Myotendious Strain Injury in mdx Mice Expressing a Truncated Dystrophin" Human Molecular Genetics. vol. 17, No. 24. 3975-3986. (2008).
Banks et al. "The Polyproline Site in Hinge 2 Influences the Functional Capacity of Truncated Dystrophins" PLoS Genetics. vol 6. pp. 1-10. (2010).
Barr et al. "Somatic gene therapy for cardiovascualr disease— Recent advances, Trends in Cardiovascular Medicine" Elsevier Science. vol 4. No 2. 57-63 (1994).
Chamberlain et al. "PCR-Mediated Mutagenesis" Encyclopedia of Life Sciences (2004).
Crawford et al. "Assembly of the Dystrophin-Associated Protein Complex Does Not Require the Dystrophin COOH-Terminal Domain" The Journal of Cell Biology. vol 150. 1399-1409. (2000).
European Search Report dated May 2, 2018 for European Application No. 16738022.
Extended European Search Report dated Aug. 20, 2018 for EP Application 16738022.9.
Goncalves et al., "Transcription Factor Rational Design Improves Directed Differentiation of Human Mesenchymal Stem Cells into Skeletal Myocytes" Biosis Biosciences Information Service (online), (2011).
Gregorevic et al. "rAAV6-Microdystrophin Preserves Muscle Function and Extends Lifespan in Severely Dystrophio Mice" Nature Medicine. vol 12. p. 253 (2002).
Harper et al. "Modular Flexibility of Dystrophin: Implications for Gene Therapy of Duchenne Muscular Dystrophy" Nature Medicine. vol 8. p. 253. (2002).
Judge et al. "Dissecting the Signaling and Mechanical Functions of the Dystrophin-Glycoprotein Complex" Journal of Cell Science ePress Publication. Research Article 1537. (2006).
Odom et al., "Gene Therapy of mdx Mice with Large Truncated Dystrophins Generated by Recombination Using AAV6" The American Society of Gene and Cell Therapy. vol 19. 36-45. (2011).
Rafael et al. "Forced expression of Dystrophin Deletion Constructs Reveals Structure-Function Correlations" The Journal of Cell Biology. vol 134. 93-102. (1996).
Salva et al., "Design of Tissue-Specific Regulatory Cassettes for High-Level rAAV-mediated Expression in Skeletal and Cardiac Muscle" Molecular Therapy, vol. 15. No 2. 320-329. (2007).
Seto et al. "Gene Replacement Therapies for Duchenne Muscular Dystrophy Using Adeno-Associated Viral Vectors" Current Gene Therapy. p. 12 (2012).
Shin et al. "Microdystrophin Ameliorates Muscular Dystrophy in the Canine Model of Duchenne Muscular Dystrophy" The American Society of Gene & Cell Therapy. vol 21. 750-757. (2013).
Warner et al. "Expression of Dp260 in Muscle Tethers the Actin Cytoskeleton to the Dystrophin-Glycoprotein Complex and Partially Prevents Dystrophy" Human Molecular Genetics. vol 11. 1095-1105. (2002).
Winder et al. "Dystrophin and Utrophin: The Missing Links!" Federation of European Biochemical Societies 15470. Letters 369. pp. 27-33. (1995).
Written Opinion dated Apr. 5, 2018 from the Intellectual Property Office of Singapore for Singapore Application No. 11201705324U.
Corrado et al., "Transgenic mdx mice expressing dystrophin with a deletion in the actin-binding domain display a "mild Becker" phenotype", J Cell Biol 134(4): 873-884 (1996).
Cox et al. "Dp71 can restore the dystrophin-associated glycoprotein complex in muscle but fails to prevent dystrophy", Nat Gen 8(4): 333-339 (1994).
Gardner et al. "Restoration of all dystrophin protein interactions by functional domains in trans does not rescue dystrophy" Gene Ther 13(9): 744-751 (2006).
Greenberg et al. "Exogenous Dp71 restores the levels of dystrophin associated proteins but does not alleviate muscle damage in mdx mice" Nat Gen 8(4): 340-344 (1994).
Koo et al., "Triple Trans-Splicing Adeno-Associated Virus Vectors Capable of Transferring the Coding Sequence for Full-Length Dystrophin Protein into Dystrophic Mice" Hum Gen Ther 25(2): 89-108 (2014).
Rafael et al. "Forced expression of dystrophin deletion constructs reveals structure-function correlations", J Cell Biol. 134(1): 93-102 (1996).
Thomas et al. "Scalable Recombinant Adeno-Associated Virus Production Using Recombinant Herpes Simplex Virus Type 1 Coinfection of Suspension-Adapted Mammalian Cells", Hum Gen Ther 20(8):861-870 (2009).
Winder et al. "The membrane—cytoskeleton interface: the role of dystrophin and utrophin", J Musc Res Cell Motility 18(6): 617-629 (1997).
Adamson-Small et al., "A scalable method for the production of high-titer and high-quality adeno-associated type 9 vectors using the HSV platform", Hum. Gene Ther. Meth., 28, (1.), 1-14, (2017).

* cited by examiner

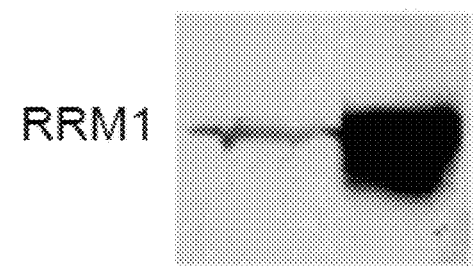
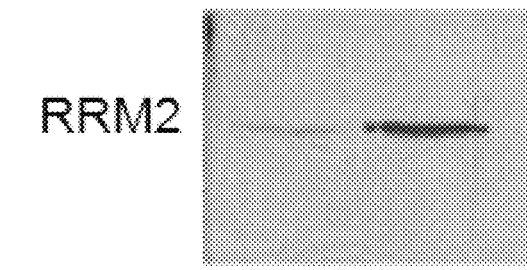
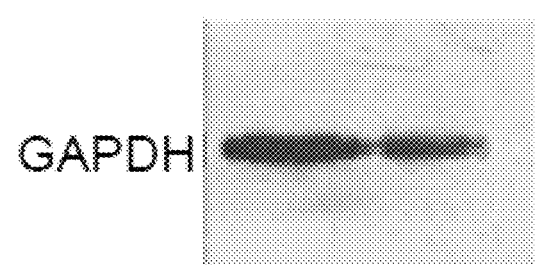
FIG. 10A
FIG. 10B
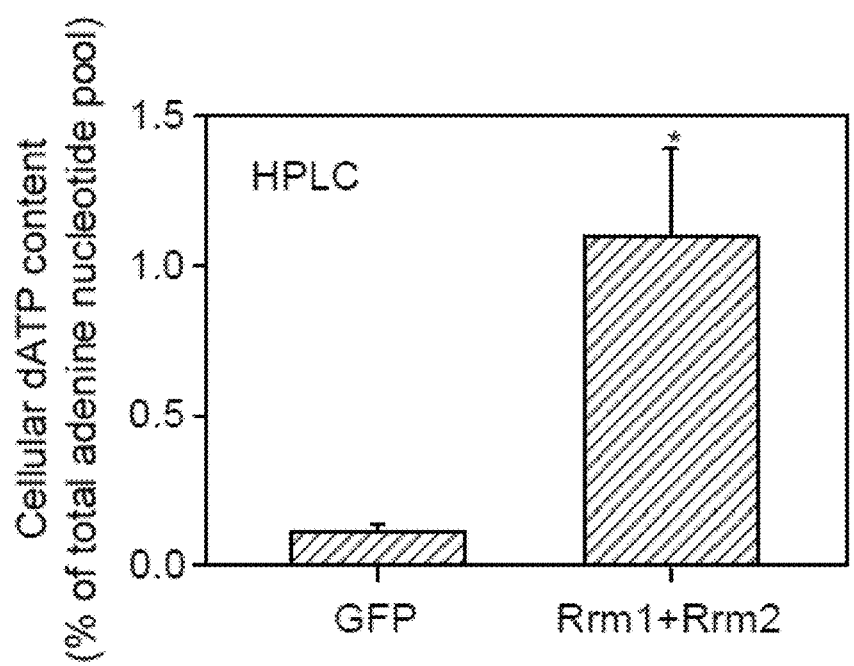
FIG. 10C

MICRO-DYSTROPHINS AND RELATED METHODS OF USE

CROSS-REFERENCE TO RELATED APPLICATIONS

This application is a divisional under 35 U.S.C. § 121 of U.S. application Ser. No. 15/541,870 filed on Jul. 6, 2017, which is a 35 U.S.C. § 371 National Phase Entry of the International Application No. PCT/US2016/013733 filed on Jan. 15, 2016, which designates the U.S., and claims benefit under 35 U.S.C. 119 (e) of U.S. Provisional Patent Application No. 62/104,537, filed on Jan. 16, 2015, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jul. 6, 2017 is named 034186-095700US-PX.txt and is 141,620 bytes in size.

STATEMENT REGARDING FEDERALLY SPONSORED RESEARCH

This invention was made with government support under Grant No. R01 AG033610, awarded by the National Institutes of Health. The government has certain rights in the invention.

TECHNICAL FIELD

The present disclosure relates generally to micro-dystrophins. The present disclosure also relates to methods of treating a subject having muscular dystrophy, sarcopenia, heart failure, or cachexia. The present disclosure also relates to methods of prophylactically treating a subject at risk of developing muscular dystrophy, sarcopenia, heart failure, or cachexia. In particular, the methods may include administering a pharmaceutical composition including a micro-dystrophin gene and a delivery vehicle to a subject. More particularly, the methods may include administering the pharmaceutical composition to a subject having Duchenne muscular dystrophy or Becker muscular dystrophy.

BACKGROUND

Duchenne muscular dystrophy (DMD) is a recessively-inherited muscle wasting disorder that affects approximately 1 in 3500 males. DMD patients carry a mutation in the dystrophin gene that causes aberrant expression or loss of expression of the dystrophin protein. DMD patients experience progressive wasting of skeletal muscles and cardiac dysfunction, which leads to loss of ambulation and premature death, primarily due to cardiac or respiratory failure. Unfortunately, currently available treatments are generally only able to slow the pathology of DMD. Accordingly, there is an urgent need for compositions and methods for treating DMD.

SUMMARY OF THE INVENTION

The present disclosure is based, at least in part, on novel micro-dystrophins, compositions thereof, and related methods of use.

In some embodiments of the present disclosure, the isolated and purified nucleotide sequence, includes: (a) a micro-dystrophin gene encoding a protein including: an amino-terminal actin-binding domain; a β-dystroglycan binding domain; and a spectrin-like repeat domain, including at least four spectrin-like repeats, such that two of the at least four spectrin-like repeats include a neuronal nitric oxide synthase binding domain; and (b) a regulatory cassette.

In one embodiment, the at least four spectrin-like repeats include spectrin-like repeat 1 (SR1), spectrin-like repeat 16 (SR16), spectrin-like repeat 17 (SR17), and spectrin-like repeat 24 (SR24).

In another embodiment, the protein encoded by the micro-dystrophin gene further includes at least a portion of a hinge domain.

In yet another embodiment, the hinge domain is selected from at least one of a Hinge 1 domain, a Hinge 2 domain, a Hinge 3 domain, a Hinge 4 domain, and a hinge-like domain.

In still another embodiment, the regulatory cassette is selected from the group consisting of a CK8 promoter and a cardiac troponin T (cTnT) promoter.

In one embodiment, the protein encoded by the micro-dystrophin gene has between five spectrin-like repeats and eight spectrin-like repeats.

In another embodiment, the protein encoded by the micro-dystrophin gene has at least 80% sequence identity to the amino acid sequence of SEQ ID NO:4.

In yet another embodiment, the protein encoded by the micro-dystrophin gene has at least 90% sequence identity to the amino acid sequence of SEQ ID NO:4.

In still another embodiment, the protein encoded by the micro-dystrophin gene has at least 80% sequence identity to the amino acid sequence of SEQ ID NO:5.

In one embodiment, the protein encoded by the micro-dystrophin gene has at least 90% sequence identity to the amino acid sequence of SEQ ID NO:5.

In another embodiment, the regulatory cassette is the CK8 promoter, and wherein the CK8 promoter has at least 80% sequence identity to the nucleic acid sequence of SEQ ID NO: 19.

In yet another embodiment, the regulatory cassette is the CK8 promoter, and wherein the CK8 promoter has at least 90% sequence identity to the nucleic acid sequence of SEQ ID NO: 19.

In still another embodiment, the regulatory cassette is the cTnT promoter, and wherein the cTnT promoter has at least 80% sequence identity to the nucleic acid sequence of SEQ ID NO:1.

In one embodiment, the regulatory cassette is the cTnT promoter, and wherein the cTnT promoter has at least 90% sequence identity to the nucleic acid sequence of SEQ ID NO:1.

In certain embodiments of the present disclosure, the isolated and purified nucleotide sequence, includes: a micro-dystrophin gene encoding a protein including: an amino-terminal actin-binding domain; and at least two spectrin-like repeats that are directly coupled to each other, wherein the at least two spectrin-like repeats that are directly coupled to each other are selected from at least one of spectrin-like repeat 1 directly coupled to spectrin-like repeat 2, spectrin-like repeat 2 directly coupled to spectrin-like repeat 3, spectrin-like repeat 1 directly coupled to spectrin-like repeat 16, spectrin-like repeat 17 directly coupled to spectrin-like repeat 23, spectrin-like repeat 17 directly coupled to spectrin-like repeat 24, and spectrin-like repeat 23 directly coupled to spectrin-like repeat 24.

In certain other embodiments of the present disclosure, the isolated and purified nucleotide sequence, includes: a micro-dystrophin gene encoding a protein including, in order: a Hinge 1 domain (H1); a spectrin-like repeat 1 (SR1); a spectrin-like repeat 16 (SR16); a spectrin-like repeat 17 (SR17); a spectrin-like repeat 24 (SR24); and a Hinge 4 domain (H4).

In one embodiment, the H1 is directly coupled to the SR1.

In another embodiment, the SR 1 is directly coupled to the SR16.

In yet another embodiment, the SR16 is directly coupled to the SR17.

In still another embodiment, the SR 17 is directly coupled to the SR24.

In another embodiment, the SR24 is directly coupled to the H4.

In yet another embodiment, the protein encoded by the micro-dystrophin gene further includes, between the SR1 and the SR16, in order, a spectrin-like repeat 2 (SR2) and a spectrin-like repeat 3 (SR3).

In still another embodiment, the SR1 is directly coupled to the SR2 and the SR2 is further coupled to the SR3.

In some embodiments of the present disclosure, the isolated and purified nucleotide sequence, includes: a micro-dystrophin gene encoding a protein including, in order: a Hinge 1 domain (H1); a spectrin-like repeat 1 (SR1); a spectrin-like repeat 16 (SR16); a spectrin-like repeat 17 (SR17); a spectrin-like repeat 23 (SR 23); a spectrin-like repeat 24 (SR24); and a Hinge 4 domain (H4).

In one embodiment, the H1 is directly coupled to the SR1, the SR1 is directly coupled to the SR16, the SR16 is directly coupled to the SR17, the SR17 is directly coupled to the SR23, the SR23 is directly coupled to the SR24, and the SR24 is directly coupled to the H4.

In certain embodiments of the present disclosure, the pharmaceutical composition, includes: an isolated and purified nucleotide sequence described herein; and a delivery vehicle.

In one embodiment, the delivery vehicle includes a recombinant adeno-associated virus vector.

In another embodiment, the delivery vehicle expresses the micro-dystrophin gene, such that the protein encoded by the micro-dystrophin gene has at least 80% sequence identity to the amino acid sequence of SEQ ID NO:4.

In yet another embodiment, the delivery vehicle expresses the micro-dystrophin gene, such that the protein encoded by the micro-dystrophin gene has at least 90% sequence identity to the amino acid sequence of SEQ ID NO:4.

In still another embodiment, the delivery vehicle expresses the micro-dystrophin gene, such that the protein encoded by the micro-dystrophin gene has at least 80% sequence identity to the amino acid sequence of SEQ ID NO:5.

In another embodiment, the delivery vehicle expresses the micro-dystrophin gene, such that the protein encoded by the micro-dystrophin gene has at least 90% sequence identity to the amino acid sequence of SEQ ID NO:5.

In some embodiments of the present disclosure, the pharmaceutical compositions described herein include a regulatory cassette, such that the regulatory cassette is the CK8 promoter, and the CK8 promoter has at least 80% sequence identity to the nucleic acid sequence of SEQ ID NO: 19.

In certain embodiments of the present disclosure, the pharmaceutical compositions described herein include a regulatory cassette, such that the regulatory cassette is the CK8 promoter, and the CK8 promoter has at least 90% sequence identity to the nucleic acid sequence of SEQ ID NO: 19.

In some embodiments of the present disclosure, the pharmaceutical compositions described herein include a regulatory cassette, such that the regulatory cassette is the cTnT promoter, and the cTnT promoter has at least 80% sequence identity to the nucleic acid sequence of SEQ ID NO:1.

In certain embodiments of the present disclosure, the pharmaceutical compositions described herein include a regulatory cassette, such that the regulatory cassette is the cTnT promoter, and the cTnT promoter has at least 90% sequence identity to the nucleic acid sequence of SEQ ID NO:1.

In some embodiments of the present disclosure, the pharmaceutical composition is configured to reduce a pathological effect or symptom of a muscular dystrophy selected from at least one of myotonic muscular dystrophy, Duchenne muscular dystrophy, Becker muscular dystrophy, limb-girdle muscular dystrophy, facioscapulohumeral muscular dystrophy, congenital muscular dystrophy, oculopharyngeal muscular dystrophy, distal muscular dystrophy, and Emery-Dreifuss muscular dystrophy.

In certain embodiments of the present disclosure, the pharmaceutical composition is configured to reduce a pathological effect or symptom of a muscular dystrophy selected from at least one of Duchenne muscular dystrophy and Becker muscular dystrophy.

In some embodiments of the present disclosure, the pharmaceutical composition is configured to reduce a pathological effect or symptom of at least one of sarcopenia, heart disease, and cachexia.

In particular embodiments of the present disclosure, the pharmaceutical composition, includes: a micro-dystrophin gene including the nucleic acid sequence of SEQ ID NO:16; and an adeno-associated virus (AAV) vector or a recombinant adeno-associated virus (rAAV) vector. In certain embodiments, the serotype of the AAV vector or the rAAV vector is selected from at least one of serotype 6, serotype 8, and serotype 9.

In some embodiments of the present disclosure, the pharmaceutical composition, includes: a micro-dystrophin gene encoding a protein, such that the protein includes the amino acid sequence of SEQ ID NO:4; and an adeno-associated virus (AAV) vector or a recombinant adeno-associated virus (rAAV) vector. In certain embodiments, the serotype of the AAV vector or the rAAV vector is selected from at least one of serotype 6, serotype 8, and serotype 9.

In certain embodiments of the present disclosure, the pharmaceutical composition, includes: a micro-dystrophin gene including the nucleic acid sequence of SEQ ID NO:18; and an adeno-associated virus (AAV) vector or a recombinant adeno-associated virus (rAAV) vector. In some embodiments, the serotype of the AAV vector or the rAAV vector is selected from at least one of serotype 6, serotype 8, and serotype 9.

In particular embodiments of the present disclosure, the pharmaceutical composition, includes: a micro-dystrophin gene encoding a protein, such that the protein includes the amino acid sequence of SEQ ID NO:5; and an adeno-associated virus (AAV) vector or a recombinant adeno-associated virus (rAAV) vector. In some embodiments, the serotype of the AAV vector or the rAAV vector is selected from at least one of serotype 6, serotype 8, and serotype 9.

In some embodiments of the present disclosure, the pharmaceutical compositions suitable for use in the treatment or prophylactic treatment of muscular dystrophy, include: a micro-dystrophin gene including the nucleic acid sequence of SEQ ID NO: 16 or SEQ ID NO:18; and an adeno-associated virus (AAV) vector or a recombinant adeno-associated virus (rAAV) vector, such that the serotype of the AAV vector or the rAAV vector is selected from at least one of serotype 6, serotype 8, and serotype 9.

In certain embodiments of the present disclosure, the pharmaceutical compositions suitable for the treatment or prophylactic treatment of muscular dystrophy, include: a micro-dystrophin gene including the nucleic acid sequence of SEQ ID NO:16 or SEQ ID NO:18; and an adeno-associated virus (AAV) vector or a recombinant adeno-associated virus (rAAV) vector, such that the serotype of the AAV vector or the rAAV vector is selected from at least one of serotype 6, serotype 8, and serotype 9.

In particular embodiments of the present disclosure, the methods for treating a subject having muscular dystrophy, include: administering to the subject a therapeutically effective amount of a pharmaceutical composition including a micro-dystrophin gene operably coupled to a regulatory cassette.

In one embodiment, the regulatory cassette is selected from the group consisting of a CK8 promoter and a cardiac troponin T (cTnT) promoter.

In another embodiment, the regulatory cassette is configured to express the micro-dystrophin gene such that a level of expression of the micro-dystrophin gene is at least 100-fold higher in striated muscle cells than the level of expression of the micro-dystrophin gene in non-muscle cells.

In certain embodiments of the present disclosure, the pharmaceutical compositions described herein further include a recombinant adeno-associated virus vector configured to express the micro-dystrophin gene in the subject.

In one embodiment, the micro-dystrophin gene encodes a protein having at least 80% sequence identity to the amino acid sequence of SEQ ID NO:4.

In another embodiment, the micro-dystrophin gene encodes a protein having at least 90% sequence identity to the amino acid sequence of SEQ ID NO:4.

In yet another embodiment, the micro-dystrophin gene encodes a protein having at least 80% sequence identity to the amino acid sequence of SEQ ID NO:5.

In still another embodiment, the micro-dystrophin gene encodes a protein having at least 90% sequence identity to the amino acid sequence of SEQ ID NO:5.

In one embodiment, the regulatory cassette is the CK8 promoter, and the CK8 promoter has at least 80% sequence identity to the nucleic acid sequence of SEQ ID NO: 19.

In another embodiment, the regulatory cassette is the CK8 promoter, and the CK8 promoter has at least 90% sequence identity to the nucleic acid sequence of SEQ ID NO:19.

In yet another embodiment, the regulatory cassette is the cTnT promoter, and the cTnT promoter has at least 80% sequence identity to the nucleic acid sequence of SEQ ID NO: 1.

In still another embodiment, the regulatory cassette is the cTnT promoter, and the cTnT promoter has at least 90% sequence identity to the nucleic acid sequence of SEQ ID NO: 1.

In one embodiment, the micro-dystrophin gene expresses a micro-dystrophin protein in one or more muscles of the subject such that contractility of the one or more muscles is enhanced.

In another embodiment, the micro-dystrophin gene expresses a micro-dystrophin protein in one or more skeletal muscles of the subject such that a specific-force generating capacity of at least one of the one or more skeletal muscles is increased to within at least 40% of a normal specific-force generating capacity.

In yet another embodiment, the micro-dystrophin gene expresses a micro-dystrophin protein in one or more cardiac muscles of the subject such that a baseline end-diastolic volume defect is restored to within at least 40% of a normal end-diastolic volume.

In still another embodiment, the micro-dystrophin gene expresses a micro-dystrophin protein such that localization of the neuronal nitric oxide synthase to the dystrophin-glycoprotein complex is enhanced in the subject.

In some embodiments, the muscular dystrophy is selected from at least one of myotonic muscular dystrophy, Duchenne muscular dystrophy, Becker muscular dystrophy, limb-girdle muscular dystrophy, facioscapulohumeral muscular dystrophy, congenital muscular dystrophy, oculopharyngeal muscular dystrophy, distal muscular dystrophy, and Emery-Dreifuss muscular dystrophy.

In certain embodiments, the muscular dystrophy is selected from at least one of Duchenne muscular dystrophy and Becker muscular dystrophy.

In some embodiments of the present disclosure, the pharmaceutical composition reduces a pathological effect or symptom of the muscular dystrophy.

In particular embodiments, the pathological effect or symptom of the muscular dystrophy is selected from at least one of muscle pain, muscle weakness, muscle fatigue, muscle atrophy, fibrosis, inflammation, increase in average myofiber diameter in skeletal muscle, cardiomyopathy, reduced 6-minute walk test time, loss of ambulation, and cardiac pump failure.

In some embodiments, the methods described herein include identifying the subject having the muscular dystrophy.

In certain embodiments, the subject is a mammal.

In particular embodiments, the subject is a human.

In some embodiments of the present disclosure, the methods for prophylactically treating a subject at risk of developing muscular dystrophy, include administering to the subject a therapeutically effective amount of a pharmaceutical composition including a micro-dystrophin gene operably coupled to a regulatory cassette.

In one embodiment, the regulatory cassette is selected from the group consisting of a CK8 promoter and a cardiac troponin T (cTnT) promoter.

In further embodiments, the regulatory cassette is configured to express the micro-dystrophin gene such that a level of expression of the micro-dystrophin gene is at least 100-fold higher in striated muscle cells than the level of expression of the micro-dystrophin gene in non-muscle cells.

In particular embodiments, the pharmaceutical composition further includes a recombinant adeno-associated virus vector configured to express the micro-dystrophin gene in the subject.

In certain embodiments, the micro-dystrophin gene encodes a protein having at least 80% sequence identity to the amino acid sequence of SEQ ID NO:4.

In another embodiment, the micro-dystrophin gene encodes a protein having at least 90% sequence identity to the amino acid sequence of SEQ ID NO:4.

In some embodiments, the micro-dystrophin gene encodes a protein having at least 80% sequence identity to the amino acid sequence of SEQ ID NO:5.

In yet another embodiment, the micro-dystrophin gene encodes a protein having at least 90% sequence identity to the amino acid sequence of SEQ ID NO:5.

In certain embodiments, the regulatory cassette is the CK8 promoter, and the CK8 promoter has at least 80% sequence identity to the nucleic acid sequence of SEQ ID NO: 19.

In another embodiment, the regulatory cassette is the CK8 promoter, and the CK8 promoter has at least 90% sequence identity to the nucleic acid sequence of SEQ ID NO:19.

In yet another embodiment, the regulatory cassette is the cTnT promoter, and the cTnT promoter has at least 80% sequence identity to the nucleic acid sequence of SEQ ID NO:1.

In still another embodiment, the regulatory cassette is the cTnT promoter, and the cTnT promoter has at least 90% sequence identity to the nucleic acid sequence of SEQ ID NO:1.

In particular embodiments, the micro-dystrophin gene expresses a micro-dystrophin protein in one or more muscles of the subject such that contractility of the one or more muscles is enhanced.

In another embodiment, the micro-dystrophin gene expresses a micro-dystrophin protein in one or more skeletal muscles of the subject such that a specific-force generating capacity of at least one of the one or more skeletal muscles is increased to within at least 40% of a normal specific-force generating capacity.

In some embodiments, the micro-dystrophin gene expresses a micro-dystrophin protein in one or more cardiac muscles of the subject such that a baseline end-diastolic volume defect is restored to within at least 40% of a normal end-diastolic volume.

In certain embodiments, the micro-dystrophin gene expresses a micro-dystrophin protein such that localization of the neuronal nitric oxide synthase to the dystrophin-glycoprotein complex is enhanced in the subject.

In particular embodiments, the muscular dystrophy is selected from at least one of myotonic muscular dystrophy, Duchenne muscular dystrophy, Becker muscular dystrophy, limb-girdle muscular dystrophy, facioscapulohumeral muscular dystrophy, congenital muscular dystrophy, oculopharyngeal muscular dystrophy, distal muscular dystrophy, and Emery-Dreifuss muscular dystrophy.

In some embodiments, the muscular dystrophy is selected from at least one of Duchenne muscular dystrophy and Becker muscular dystrophy.

In certain embodiments, the pharmaceutical compositions described herein reduce a risk of developing a pathological effect or symptom of the muscular dystrophy.

In one embodiment, the pathological effect or symptom of the muscular dystrophy is selected from at least one of muscle pain, muscle weakness, muscle fatigue, muscle atrophy, fibrosis, inflammation, increase in average myofiber diameter in skeletal muscle, cardiomyopathy, reduced 6-minute walk test time, loss of ambulation, and cardiac pump failure.

In some embodiments of the present disclosure, the methods described herein further include identifying the subject at risk of developing the muscular dystrophy.

In one embodiment, the subject is a mammal.

In another embodiment, the subject is a human.

Other features and advantages of the disclosure will be apparent from the following detailed description and claims.

BRIEF DESCRIPTION OF THE DRAWINGS

The embodiments disclosed herein will become more fully apparent from the following description and appended claims, taken in conjunction with the accompanying drawings.

Figure 1A:
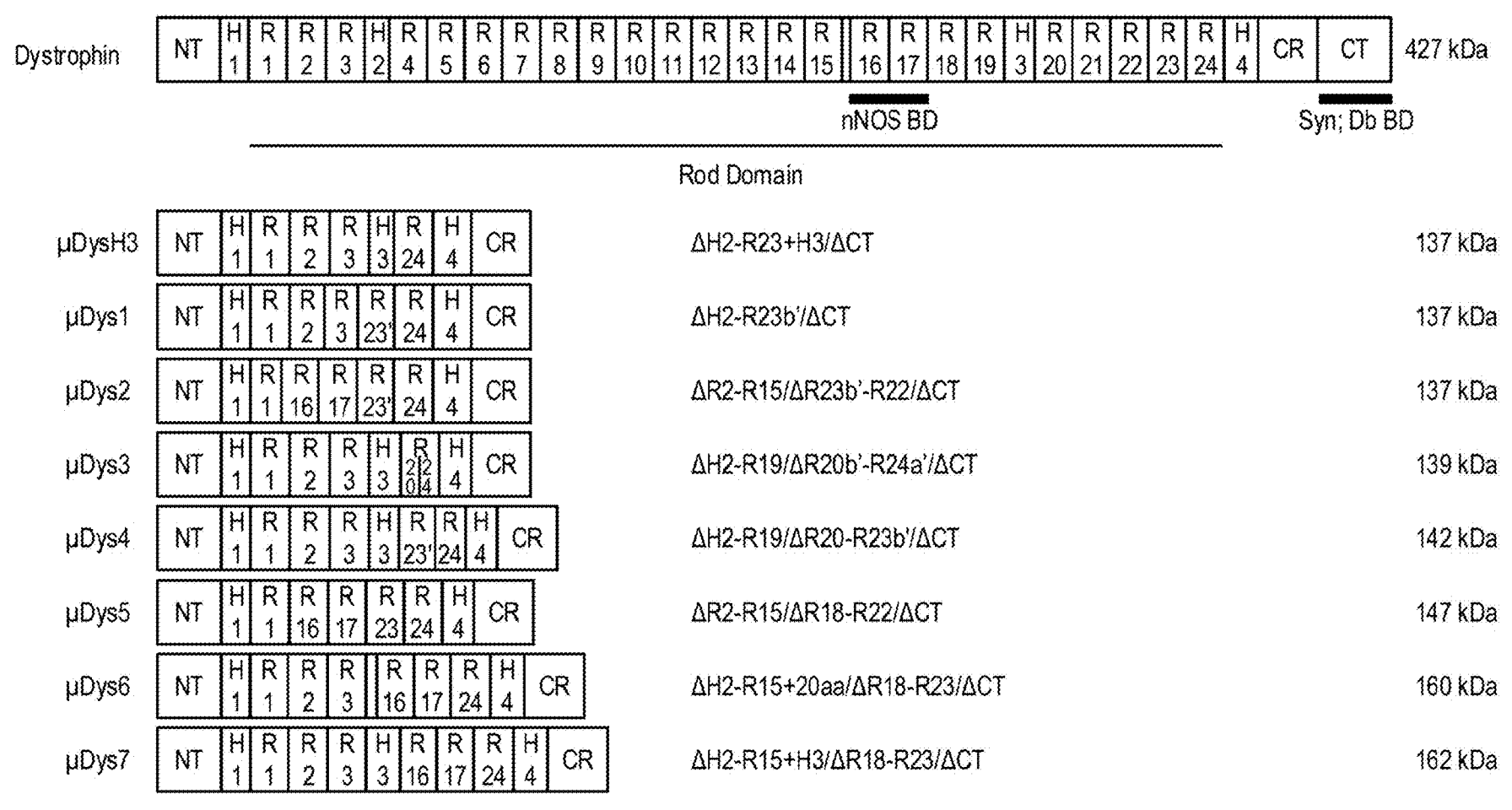

FIG. 1A depicts protein structure diagrams of embodiments of truncated dystrophin constructs as disclosed herein. NT, amino terminal domain; H, hinge; R, spectrin-like repeat; nNOS BD, neuronal nitric oxide synthase binding domain; CR, cysteine-rich domain; CT, carboxyl terminal domain; Syn, syntrophin binding domain; Db BD, dystrobrevin binding domain; the unlabeled region marks 20-amino acids between R15 and R16; aa, amino acid; and kDa, kilodalton.

FIG. 7 depicts protein structure diagrams of embodiments of novel micro-dystrophin constructs as disclosed herein. The top protein structure diagram is of full-length dystrophin showing many of the known functional domains: NT, amino terminal actin-binding domain; H, hinge; R, spectrin-like repeat; nNOS BD, neuronal nitric oxide synthase binding domain; CR, cysteine-rich domain; CT, carboxyl terminal domain; Dg BD, dystroglycan binding domain; Syn, syntrophin binding domain; Db BD, dystrobrevin binding domain; and the unlabeled region marks 20-amino acids between R15 and R16. The WW domain is within Hinge 4. On the left are shown the micro-dystrophin protein structures, with the designated name to the left of the protein structure diagram, and the domain structure listed to the right of the schematic diagram.

FIG. 10A is a Western blot for R1, with GAPDH as a loading control.

FIG. 10B is a Western blot for R2, with GAPDH as a loading control.

FIG. 10C is a graph depicting HPLC of transfected cardiomyocytes [dATP].

FIG. 14 also provides data for heart tissue from non-injected (panel "B") vs. AAV6-alkaline phosphatase (panel "C") injected mice (see Rafael, J. A., et al., The Journal of Cell Biology 134, 93-102 (1996)) after 20 months, suggesting AAV6-R1R2$^{cTnT455}$ may provide stable, long-term R1R2 over-expression.

DETAILED DESCRIPTION

Figure 1B:
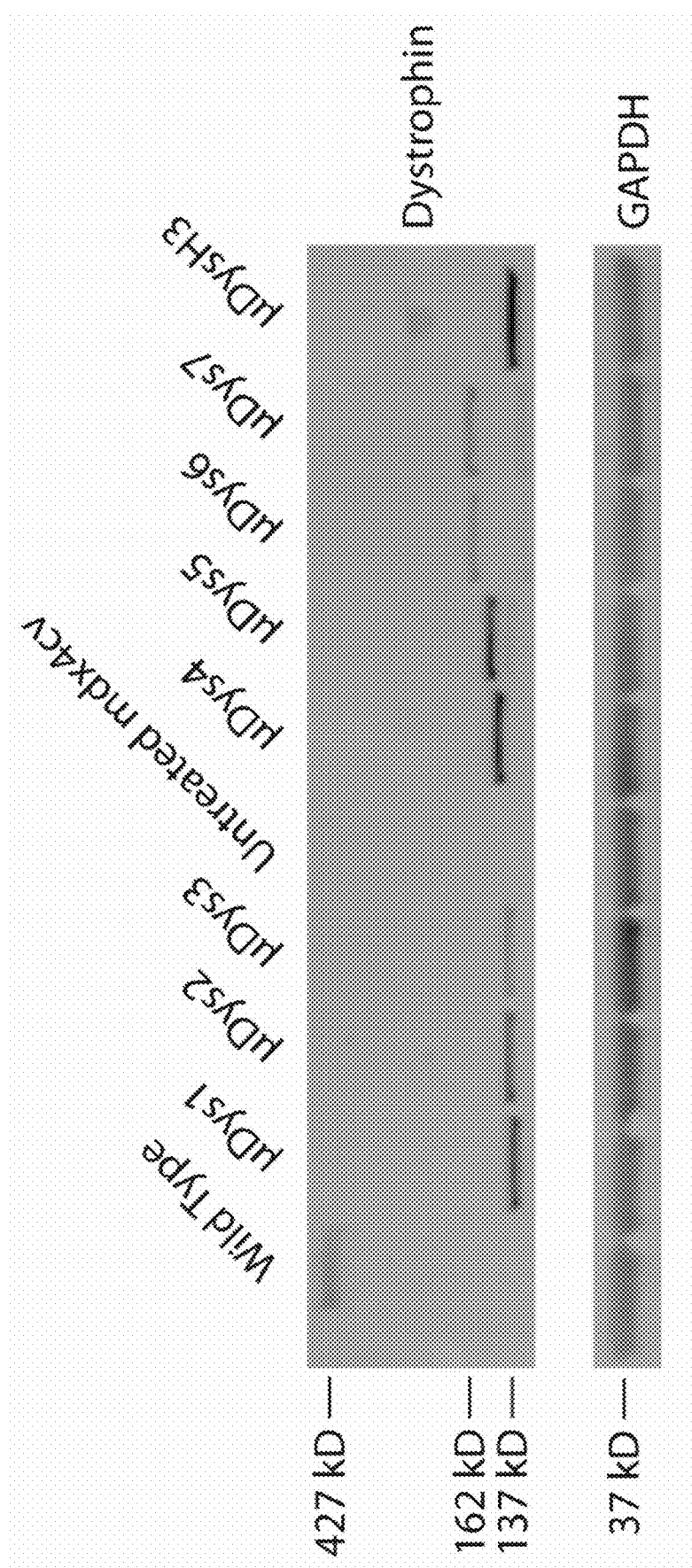
FIG. 1B is a Western blot illustrating the results of injecting dystrophic mdx$^{4cv}$ mice with $5\times10^{10}$ vector genomes (vg) of rAAV/CMV-µDys into one tibialis anterior (TA) muscle while, the contralateral muscle served as an internal, untreated control. Expression of all tested constructs was verified at 4 weeks after treatment by Western blot analysis of TA muscle lysates, along with wild type and untreated mdx$^{4cv}$ controls. Glyceraldehyde-3-phosphate dehydrogenase (GAPDH) served as an internal loading control.

The present disclosure features compositions and methods for treating Duchenne muscular dystrophy (DMD). More particularly, the present disclosure relates to methods for producing mini-dystrophin proteins for treating a subject having muscular dystrophy, DMD, sarcopenia, heart failure, and/or cachexia. As described in detail below, the present disclosure is based, at least in part, on the unexpected discovery that mini-dystrophin proteins comprising specific combinations of protein domains (e.g., a mini-dystrophin protein including an N-terminal domain, H1 domain, SR1 domain, SR16 domain, SR17 domain, SR 23 domain, SR24 domain, H4 domain, and CR domain) from the dystrophin protein are able to restore dystrophin function to levels sufficient to treat muscular dystrophy, DMD, sarcopenia, heart failure, and/or cachexia.

Duchenne muscular dystrophy (DMD) is a recessively-inherited muscle wasting disorder afflicting approximately 1 in 3500 males. DMD patients carry a mutation in the dystrophin gene, resulting in aberrant or absent expression of the dystrophin protein. DMD patients experience progressive wasting of skeletal muscles and cardiac dysfunction, leading to loss of ambulation and premature death, primarily due to cardiac or respiratory failure. Current available treatments are generally only able to slow the pathology of DMD (see Emery, A. E. H. and Muntoni, F., Duchenne Muscular Dystrophy, Third Edition (Oxford University Press, 2003)). Gene therapy approaches for DMD have been demonstrated in dystrophic animal models by either directly targeting a class of mutations, as with exon skipping, or replacing the mutated gene with viral-vector mediated delivery (see Koo, T. and Wood, M. J. Human Gene Therapy 24, (2013); Benedetti, S., et al., The FEBS Journal 280, 4263-4280, (2013); and Seto, J. T., et al., Current Gene Therapy 12, 139-151 (2012)). Recombinant adeno-associated virus (rAAV) vectors are a potential vehicle for gene therapy, being already tested in clinical trials for both DMD and limb-girdle muscular dystrophies (see Mendell, J. R., et al., The New England Journal of Medicine 363, 1429-1437, (2010); Mendell, J. R., et al., Annals of Neurology 68, 629-638 (2010); and Herson, S., et al., Brain: A Journal of Neurology 135, 483-492, (2012)). Several serotypes of adeno-associated virus (AAV) demonstrate a high degree of tropism for striated muscles (see Seto, J. T., et al., Current Gene Therapy 12, 139-151 (2012)).

Pre-clinical studies designing and testing newer generations of therapeutic constructs for DMD can be confined by the approximately 4.9 kb size of a single-stranded rAAV vector genome (see Dong, B., et al., Molecular Therapy: The Journal of the American Society of Gene Therapy 18, 87-92, (2010) and Wu, Z., et al., Molecular Therapy: The Journal of the American Society of Gene Therapy 18, 80-86, (2010)). Packaging the entire approximately 13.9 kb cDNA of the muscle-specific isoform of dystrophin into a single rAAV capsid cannot be achieved, accordingly, miniaturized, synthetic versions of the muscle-specific isoform of dystrophin cDNA may be used. Although in vivo recombination of two and three rAAV vector genomes has been demonstrated to deliver a mini- or full-length dystrophin coding sequence (see, Odom, G. L., et al., Molecular Therapy: The Journal of the American Society of Gene Therapy 19, 36-45, (2011); Lostal, W., et al., Human Gene Therapy, (2014); and Koo, T., et al., Human Gene Therapy 25, 98-108, (2014)), the efficiency of delivering multiple vectors for reconstituting full-length dystrophin may be suboptimal and can increase the overall dose of viral capsid proteins needed for delivering vectors. However, beneficial rAAV-mediated gene therapy has been achieved using rationally-designed miniature versions of the dystrophin cDNA based in part on mRNA expressed in mild Becker muscular dystrophy patients carrying in-frame deletions within the gene (see Beggs, A. H., et al., American Journal of Human Genetics 49, 54-67 (1991); Koenig, M., et al., American Journal of Human Genetics 45, 498-506 (1989); Goldberg, L. R., et al., Annals of Neurology 44, 971-976, (1998); and England, S. B., et al., Nature 343, 180-182 (1990)). Studies in transgenic and vector treated dystrophic mice expressing various dystrophin truncations have identified several elements of the dystrophin gene that may be present in a functional micro-dystrophin (µDys) (see Harper, S. Q., et al., Nature Medicine 8, 253-261, (2002)).

The full-length striated muscle isoform of dystrophin can play a role in transmitting contractile force through the sarcolemma and out to the extracellular matrix. In addition to maintaining the mechanical link between the intracellular cytoskeleton and the membrane bound dystrophin glycoprotein complex (DGC), dystrophin can also be a scaffold for signaling proteins (see Ozawa, E. in Myology (ed. Franzini-Armstrong C Engel A) 455-470 (McGraw-Hill, 2004); Winder, S. J. Journal of Muscle Research and Cell Motility 18, 617-629 (1997); and Campbell, K. P. and Kahl, S. D. Nature 338, 259-262, (1989)). The amino-terminal domain of dystrophin can bind to F-actin filaments of the intracellular cytoskeleton (see Way, M., et al., FEBS Letters 301, 243-245 (1992); Hemmings, L., et al., The Journal of Cell Biology 116, 1369-1380 (1992); Fabbrizio, E., et al., Biochemistry 32, 10457-10463 (1993); and Pavalko, F. M. and Otey, C. A. Proceedings of the Society for Experimental Biology and Medicine 205, 282-293 (1994)). The middle, rod domain is the largest and is composed of 24 spectrin-like repeats (SRs) that are flanked and interspersed with at least four hinge sub-domains. The rod domain can give dystrophin elasticity and flexibility for maintaining the integrity of the sarcolemma during muscle contractility (see Winder, S. J. Journal of Muscle Research and Cell Motility 18, 617-629 (1997)). Various SRs provide unique regions that can serve as additional binding sites for the intracellular cytoskeleton, the sarcolemma, as well as members of the DGC (see Rybakova, I. N., et al., The Journal of Cell Biology 135, 661-672 (1996); Warner, L. E., et al., Human Molecular Genetics 11, 1095-1105 (2002); Metzinger, L., et al., Human Molecular Genetics 6, 1185-1191 (1997); Lai, Y., et al., The Journal of Clinical Investigation 119, 624-635, (2009)). In particular, the cysteine-rich domain and the adjacent Hinge 4 region form the β-dystroglycan binding domain (Dg BD) (see Blake, D. J., et al., Physiological Reviews 82, 291-329, (2002); Ishikawa-Sakurai, M., et al., Human Molecular Genetics 13, 693-702, (2004)), while the carboxy-terminal domain is a scaffold for additional DGC components (see Abmayr S, in Molecular Mechanisms of Muscular Dystrophies (ed. Winder, S. J.) 14-34 (Landes Biosciences, 2006)).

Partially functional micro-dystrophins can improve the dystrophic pathology in striated muscle by protecting the sarcolemma from contraction-induced injury and increasing the capacity to generate force. These parameters can be achieved by binding to F-actin filaments and β-dystroglycan through the amino-terminal domain and the Dg BD (see Harper, S. Q., et al., Nature Medicine 8, 253-261, (2002); Warner, L. E., et al., Human Molecular Genetics 11, 1095-1105 (2002); Cox, G. A., et al., Nature Genetics 8, 333-339, (1994); Greenberg, D. S., et al., Nature Genetics 8, 340-344, (1994); Gardner, K. L., et al., Gene Therapy 13, 744-751, (2006); Corrado, K., et al., The Journal of Cell Biology 134, 873-884 (1996); and Rafael, J. A., et al., The Journal of Cell Biology 134, 93-102 (1996)). Without being bound by any one particular theory, prior studies indicate these two domains must be connected by at least four SRs from the central rod domain, but there are numerous ways in which miniaturized dystrophins containing at least four SRs can be constructed. While some combinations of SRs have been shown to improve the dystrophic pathophysiology, other combinations have not yielded proteins with significant functional capacity (see Harper, S. Q., et al., Nature Medicine 8, 253-261, (2002) and Abmayr S, in Molecular Mechanisms of Muscular Dystrophies (ed. Winder, S. J.) 14-34 (Landes Biosciences, 2006)). Selection of specific SRs in µDys design can restore additional DGC components to the sarcolemma. Neuronal nitric oxide synthase (nNOS) is a signaling protein that can be involved in vasodilation in response to muscle contractile activity (see Stamler, J. S. and Meissner, G. Physiological Reviews 81, 209-237 (2001); Brenman, J. E., et al., Cell 82, 743-752 (1995); Kobayashi, Y. M., et al., Nature 456, 511-515, (2008); and Torelli, S., et al., Neuropathology and Applied Neurobiology 30, 540-545, (2004)), and the presence of SRs 16 and 17 can be involved in proper association of nNOS with the DGC (see 28 Lai, Y. et al., The Journal of Clinical Investigation 119, 624-635, (2009) and Lai, Y., et al., Proceedings of the National Academy of Sciences of the United States of America 110, 525-530, (2013)).

Sequences within spectrin-like repeats 20-24 as well as Hinge 4 can play a role in proper association of dystrophin with microtubules, which can be important for maintaining the intracellular architecture and torque production in skeletal muscle (see Prins, K. W. et al., The Journal of Cell Biology 186, 363-369, (2009) and Belanto, J. J., et al., Proceedings of the National Academy of Sciences of the United States of America 111, 5723-5728, (2014)). Nonetheless, the carboxy-terminal domain and most of the SR domains have been found dispensable without severely compromising the health of striated muscles (see McCabe, E. R., et al., The Journal of Clinical Investigation 83, 95-99, (1989); Crawford, G. E., et al., The Journal of Cell Biology 150, 1399-1410 (2000); and Dunckley, M. G., et al., FEBS Letters 296, 128-134 (1992)).

Several of the best micro-dystrophins tested to date can protect muscles from contraction-induced injury and restore some, but generally not all, of the specific force generating capacity to dystrophic mouse and canine models for DMD (see Seto, J. T., et al., Current Gene Therapy 12, 139-151 (2012) and Wang, Z., et al., Frontiers in Microbiology 2, 201, (2011)). Other micro-dystrophins carrying different combinations of SRs and hinges may function less well in dystrophic muscles, and the reasons for differences in functionality are not clear. However, without being bound by any one particular theory, they may relate to effects on micro-dystrophin elasticity, folding, stability, and the ability to assemble sub-portions of the DGC without steric hindrance.

The present disclosure relates generally to micro-dystrophins. The micro-dystrophins may be operatively linked to a regulatory cassette. The present disclosure also relates to methods of treating a subject having muscular dystrophy, sarcopenia, heart failure, or cachexia. Further, the present disclosure relates to methods of prophylactically treating a subject at risk of developing muscular dystrophy, sarcopenia, heart failure, or cachexia. The methods for treating a subject having, or at risk of developing, muscular dystrophy, sarcopenia, heart failure, or cachexia may comprise administering a pharmaceutical composition including a micro-dystrophin gene and a delivery vehicle to the subject.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

Unless specifically defined otherwise, the technical terms, as used herein, have their normal meaning as understood in the art. The following terms are specifically defined with examples for the sake of clarity.

As used herein, "peptide" and "polypeptide" may be used in their broadest senses to refer to a sequence of subunit amino acids. The peptides or polypeptides of the disclosure may comprise L-amino acids, D-amino acids (which can be resistant to L-amino acid-specific proteases in vivo), or a combination of D- and L-amino acids. The terms peptide and polypeptide can be used interchangeably. The peptides and polypeptides described herein may be chemically synthesized or recombinantly expressed. The peptides and polypeptides may be linked to any other moiety as deemed useful for a given purpose. Such linkage can comprise covalent linkages or non-covalent linkages as is understood by those of skill in the art.

Amino acid residues as disclosed herein can be modified by conservative substitutions to maintain, or substantially maintain, overall polypeptide structure and/or function. As used herein, "conservative amino acid substitution" indicates that: hydrophobic amino acids (i.e., Ala, Cys, Gly, Pro, Met, Val, Ile, and Leu) can be substituted with other hydrophobic amino acids; hydrophobic amino acids with bulky side chains (i.e., Phe, Tyr, and Trp) can be substituted with other hydrophobic amino acids with bulky side chains; amino acids with positively charged side chains (i.e., Arg, His, and Lys) can be substituted with other amino acids with positively charged side chains; amino acids with negatively charged side chains (i.e., Asp and Glu) can be substituted with other amino acids with negatively charged side chains;

and amino acids with polar uncharged side chains (i.e., Ser, Thr, Asn, and Gln) can be substituted with other amino acids with polar uncharged side chains.

Treating a subject can comprise delivering an effective amount or delivering a prophylactic treatment and/or a therapeutic treatment to a subject (e.g., a patient). An "effective amount" is an amount of a compound that can result in a desired physiological change in a subject. Effective amounts may also be administered for research purposes.

A "prophylactic treatment" comprises a treatment administered to a subject who does not display signs or symptoms of a disease or condition, or a subject who displays only early signs or symptoms of a disease or condition, such that treatment is administered for the purpose of diminishing, preventing, and/or decreasing the risk of further developing the disease or condition or of diminishing, preventing, and/or decreasing the risk of developing the disease or condition. Thus, a prophylactic treatment may function as a preventive treatment against a disease or condition.

A "therapeutic treatment" comprises a treatment administered to a subject who displays symptoms or signs of a disease or a condition and the therapeutic treatment is administered to the subject for the purpose of diminishing or eliminating the symptoms or the signs of the disease or the condition.

"Therapeutically effective amounts" comprise amounts that provide prophylactic treatment and/or therapeutic treatment. Therapeutically effective amounts need not fully prevent or cure the disease or the condition but can also provide a partial benefit, such as a delay of onset or an alleviation or an improvement of at least one symptom of the disease or the condition.

For administration, effective amounts and therapeutically effective amounts (also referred to herein as doses) can be initially estimated based on results from in vitro assays and/or animal model studies. For example, a dose can be formulated in animal models to achieve a circulating concentration range that includes the $IC_{50}$ as determined in cell culture. Such information can be used to more accurately determine useful doses in subjects of interest.

The actual dose amount administered to a particular subject can be determined by a physician, a veterinarian, or a researcher, taking into account parameters such as, but not limited to, physical and physiological factors including body weight, severity of condition, type of disease, previous or concurrent therapeutic interventions, idiopathy of the subject, and/or route of administration.

Doses can range from $1\times10^8$ vector genomes per kg (vg/kg) to $1\times10^{15}$ vg/kg, from $1\times10^9$ vg/kg to $1\times10^{14}$ vg/kg, from $1\times10^{10}$ vg/kg to $1\times10^{13}$ vg/kg, or from $1\times10^{11}$ vg/kg to $1\times10^{12}$ vg/kg. In other non-limiting examples, a dose can comprise about $1\times10^8$ vg/kg, about $1\times10^9$ vg/kg, about $1\times10^{10}$ vg/kg, about $1\times10^{11}$ vg/kg, about $1\times10^{12}$ vg/kg, about $1\times10^{13}$ vg/kg, about $1\times10^{14}$ vg/kg, or about $1\times10^{15}$ vg/kg. Therapeutically effective amounts can be achieved by administering single or multiple doses during the course of a treatment regimen (i.e., days, weeks, months, etc.).

Pharmaceutically acceptable salts, tautomers, and isomers of the compounds disclosed herein can also be used. Exemplary salts can include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The formulations described herein can be administered by, without limitation, injection, infusion, perfusion, inhalation, lavage, and/or ingestion. Routes of administration can include, but are not limited to, intravenous, intradermal, intraarterial, intraperitoneal, intralesional, intracranial, intraarticular, intraprostatic, intrapleural, intratracheal, intranasal, intravitreal, intravaginal, intrarectal, topically, intratumoral, intramuscular, intravesicular, intrapericardial, intraumbilical, intraocularal, mucosal, oral, subcutaneous, and/or subconjunctival. In other non-limiting examples, administration can be performed by intramuscular injection, intravascular injection, intraperitoneal injection, or any other method suitable for delivery of vector to musculature.

In some embodiments, for injection, formulations can be made as aqueous solutions, such as in buffers including, but not limited to, Hanks' solution, Ringer's solution, and/or physiological saline. The solutions can contain formulatory agents such as suspending, stabilizing, and/or dispersing agents. Alternatively, the formulation can be in lyophilized and/or powder form for constitution with a suitable vehicle control (e.g., sterile pyrogen-free water) before use.

Any formulation disclosed herein can advantageously comprise any other pharmaceutically acceptable carrier or carriers which comprise those that do not produce significantly adverse, allergic, or other untoward reactions that may outweigh the benefit of administration, whether for research, prophylactic, and/or therapeutic treatments. Exemplary pharmaceutically acceptable carriers and formulations are disclosed in Remington's Pharmaceutical Sciences, 18th Ed., Mack Printing Company, 1990, which is incorporated by reference herein for its teachings regarding the same. Moreover, formulations can be prepared to meet sterility, pyrogenicity, general safety, and purity standards as required by the United States FDA's Division of Biological Standards and Quality Control and/or other relevant U.S. and foreign regulatory agencies.

Exemplary, generally used pharmaceutically acceptable carriers may comprise, but are not limited to, bulking agents or fillers, solvents or co-solvents, dispersion media, coatings, surfactants, antioxidants (e.g., ascorbic acid, methionine, and vitamin E), preservatives, isotonic agents, absorption delaying agents, salts, stabilizers, buffering agents, chelating agents (e.g., EDTA), gels, binders, disintegration agents, and/or lubricants.

Exemplary buffering agents may comprise, but are not limited to, citrate buffers, succinate buffers, tartrate buffers, fumarate buffers, gluconate buffers, oxalate buffers, lactate buffers, acetate buffers, phosphate buffers, histidine buffers, and/or trimethylamine salts.

Exemplary preservatives may comprise, but are not limited to, phenol, benzyl alcohol, meta-cresol, methylparaben, propyl paraben, octadecyldimethylbenzyl ammonium chloride, benzalkonium halides, hexamethonium chloride, alkyl parabens (such as methyl or propyl paraben), catechol, resorcinol, cyclohexanol, and/or 3-pentanol.

Exemplary isotonic agents may comprise polyhydric sugar alcohols comprising, but not limited to, trihydric or higher sugar alcohols, (e.g., glycerin, erythritol, arabitol, xylitol, sorbitol, and/or mannitol).

Exemplary stabilizers may comprise, but are not limited to, organic sugars, polyhydric sugar alcohols, polyethylene glycol, sulfur-containing reducing agents, amino acids, low molecular weight polypeptides, proteins, immunoglobulins, hydrophilic polymers, and/or polysaccharides.

Formulations can also be depot preparations. In some embodiments, such long-acting formulations may be administered by, without limitation, implantation (e.g., subcutaneously or intramuscularly) or by intramuscular injection. Thus, for example, compounds can be formulated with suitable polymeric and/or hydrophobic materials (e.g., as an emulsion in an acceptable oil) or ion exchange resins, or as sparingly soluble derivatives (e.g., as a sparingly soluble salt).

Additionally, in various embodiments, compounds can be delivered using sustained-release systems, such as semipermeable matrices of solid polymers comprising at least one compound. Various sustained-release materials have been established and are well known by those of ordinary skill in the art. Sustained-release capsules may, depending on their chemical nature, release the compound following administration for a few weeks up to over 100 days.

Gene therapy methods can be used for delivering (e.g., at sustained levels) specific proteins into patients or subjects. These methods allow practitioners to introduce DNA coding for a gene of interest directly into a patient or subject (in vivo gene therapy) or into cells isolated from a patient, a subject, or a donor (ex vivo gene therapy). The introduced DNA then directs the patient's or subject's own cells or grafted cells to produce the desired protein product. Gene delivery, therefore, can obviate the need for daily injections. Gene therapy may also allow practitioners to select specific organs or cellular targets (e.g., muscle, liver, blood cells, brain cells, etc.) for therapy.

DNA may be introduced into a subject's cells in several ways. There are transfection methods, including chemical methods such as calcium phosphate precipitation and liposome-mediated transfection, and physical methods such as electroporation. In general, transfection methods are not suitable for in vivo gene delivery. There are also methods that use recombinant viruses. Current viral-mediated gene delivery methods include, but are not limited to, retrovirus, adenovirus, herpes virus, pox virus, and adeno-associated virus (AAV) vectors.

One viral system that has been used for gene delivery is adeno-associated virus (AAV). AAV is a parvovirus which belongs to the genus Dependoparvovirus. AAV has several attractive features not found in other viruses. First, AAV can infect a wide range of host cells, including non-dividing cells. Second, AAV can infect cells from different species. Third, AAV has not been associated with any human or animal disease and does not appear to alter the biological properties of the host cell upon integration. Indeed, it is estimated that 80-85% of the human population has been exposed to the virus. Finally, AAV is stable at a wide range of physical and chemical conditions which lends itself to production, storage, and transportation requirements.

The AAV genome is a linear, single-stranded DNA molecule containing 4681 nucleotides. The AAV genome generally comprises an internal non-repeating genome flanked on each end by inverted terminal repeats (ITRs). The ITRs are approximately 145 base pairs (bp) in length. The ITRs have multiple functions, including as origins of DNA replication and as packaging signals for the viral genome.

The internal non-repeated portion of the genome includes two large open reading frames, known as the AAV replication (rep) and capsid (cap) genes. The rep and cap genes code for viral proteins that allow the virus to replicate and package the viral genome into a virion. In particular, a family of at least four viral proteins are expressed from the AAV rep region, Rep78, Rep68, Rep52, and Rep40, named according to their apparent molecular weight. The AAV cap region encodes at least three proteins, VP1, VP2, and VP3.

AAV is a helper-dependent virus; that is, it requires co-infection with a helper virus (e.g., adenovirus, herpesvirus, or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. While AAV can infect cells from different species, the helper virus must be of the same species as the host cell. Thus, for example, human AAV will replicate in canine cells co-infected with a canine adenovirus.

"Gene transfer" or "gene delivery" comprises methods or systems for inserting foreign DNA into host cells. Gene transfer can result in transient expression of non-integrated transferred DNA, extrachromosomal replication, and expression of transferred replicons (e.g., episomes), or integration of transferred genetic material into the genomic DNA of host cells.

A "vector" comprises any genetic element, such as, but not limited to, a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors.

An "AAV vector" comprises a vector derived from an adeno-associated virus serotype, including without limitation, AAV1, AAV2, AAV3, AAV4, AAV5, AAV6, AAV7, AAV8, and AAV9. AAV vectors can have one or more of the AAV wild-type genes deleted in whole or part, e.g., the rep and/or cap genes, but retain functional flanking ITR sequences. Functional ITR sequences are necessary for the rescue, replication, and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

A "recombinant AAV vector" or "rAAV vector" comprises an infectious, replication-defective virus composed of an AAV protein shell encapsulating a heterologous nucleotide sequence of interest that is flanked on both sides by AAV ITRs. An rAAV vector is produced in a suitable host cell comprising an AAV vector, AAV helper functions, and accessory functions. In this manner, the host cell is rendered capable of encoding AAV polypeptides that are required for packaging the AAV vector (containing a recombinant nucleotide sequence of interest) into infectious recombinant virion particles for subsequent gene delivery.

A first aspect of the disclosure relates to nucleotide sequences including a micro-dystrophin gene encoding a protein. The nucleotide sequences may also include a regulatory cassette. Additionally, the nucleotide sequences may be isolated and/or purified.

In some embodiments, the protein encoded by the micro-dystrophin gene may include an amino-terminal actin-binding domain, a dystroglycan-binding domain, and/or a spectrin-like repeat domain. The spectrin-like repeat domain may include at least four spectrin-like repeats or portions of at least four spectrin-like repeats. Two of the at least four spectrin-like repeats may comprise a neuronal nitric oxide synthase binding domain. Stated another way, the at least four spectrin-like repeats may include spectrin-like repeats 16 and 17 or portions thereof. In some embodiments, the at least four spectrin-like repeats may include spectrin-like repeats 1 and 24 or portions thereof. In alternative embodiments, the at least four spectrin-like repeats may include other suitable spectrin-like repeats or portions thereof (e.g., spectrin-like repeats 2, 3, 4, 5, 6, 7, 8, 9, 10, 11, 12, 13, 14, 15, 18, 19, 20, 21, 22, and/or 23).

In certain embodiments, the spectrin-like repeat domain may include four, five, six, seven, eight, or more spectrin-like repeats or portions thereof. In certain other embodiments, the protein encoded by the micro-dystrophin gene may include between five spectrin-like repeats and eight spectrin-like repeats (e.g., five, six, seven, or eight spectrin-like repeats). In yet certain other embodiments, the spectrin-like repeat domain may include another suitable number of spectrin-like repeats or portions thereof.

In some embodiments, the protein encoded by the micro-dystrophin gene may further comprise a hinge domain or a portion thereof. For example, the protein encoded by the micro-dystrophin gene may include at least a portion of a hinge domain selected from at least one of a Hinge 1 domain, a Hinge 2 domain, a Hinge 3 domain, a Hinge 4 domain, and/or a hinge-like domain (such as the hinge-like domains encoded by the sequences downstream from spectrin-like repeat 15 (SEQ ID NO: 20) and within spectrin-like repeat 23 (SEQ ID NO:21)).

In various embodiments, the micro-dystrophin gene may include a portion of the nucleic acid sequence of SEQ ID NO: 16. In various other embodiments, the micro-dystrophin gene may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO:16. In yet various other embodiments, the micro-dystrophin gene may have 100% sequence identity to the nucleic acid sequence of SEQ ID NO: 16.

In some embodiments, the protein encoded by the micro-dystrophin gene may include a portion of the amino acid sequence of SEQ ID NO:4. In some other embodiments, the protein encoded by the micro-dystrophin gene may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:4. In yet some other embodiments, the protein encoded by the micro-dystrophin gene may have 100% sequence identity to the amino acid sequence of SEQ ID NO:4.

In certain embodiments, the micro-dystrophin gene may include a portion of the nucleic acid sequence of SEQ ID NO: 18. In certain other embodiments, the micro-dystrophin gene may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO:18. In yet various other embodiments, the micro-dystrophin gene may have 100% sequence identity to the nucleic acid sequence of SEQ ID NO: 18.

In various embodiments, the protein encoded by the micro-dystrophin gene may include a portion of the amino acid sequence of SEQ ID NO:5. In various other embodiments, the protein encoded by the micro-dystrophin gene may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:5. In yet various other embodiments, the protein encoded by the micro-dystrophin gene may have 100% sequence identity to the amino acid sequence of SEQ ID NO:5.

Figure 7:
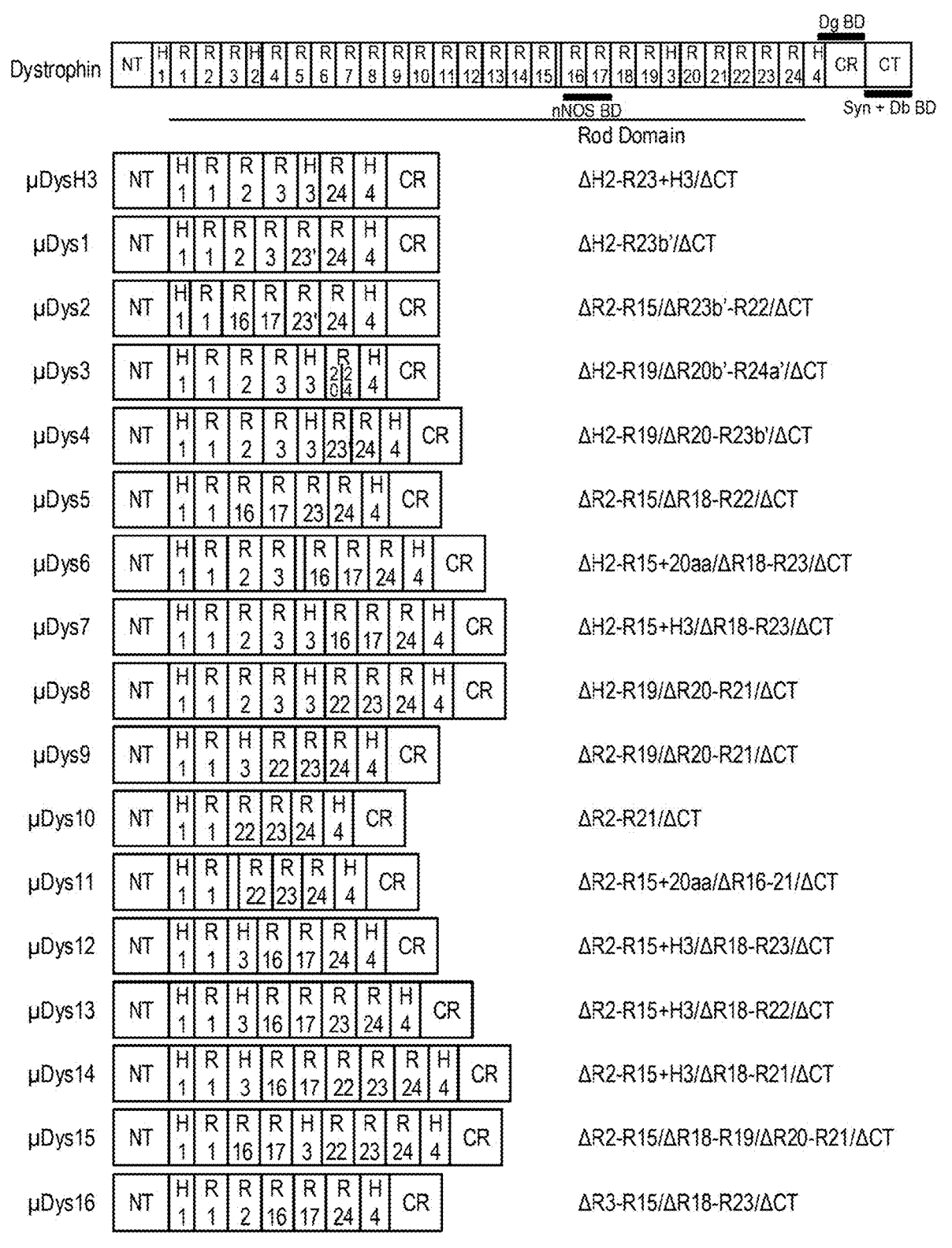

Further, the micro-dystrophin gene may include a portion of one or more of the nucleic acid sequences of SEQ ID NOs: 11-18. In certain embodiments, the protein encoded by the micro-dystrophin gene may include a portion of one or more of the amino acid sequences of SEQ ID NO:3-10. In certain other embodiments, the protein encoded by the micro-dystrophin gene may include a portion of one or more of the proteins depicted in the protein structure diagrams of FIG. 7 (e.g., µDysH3 and µDys1-µDys16).

In some embodiments, the regulatory cassette may be selected from at least one of a CK8 promoter, a cardiac troponin T (cTnT) promoter, and/or another suitable regulatory cassette. In certain embodiments, the regulatory cassette may be the CK8 promoter and the CK8 promoter may comprise a portion of the nucleic acid sequence of SEQ ID NO:19. In certain other embodiments, the regulatory cassette may be the CK8 promoter and the CK8 promoter may have at least at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO:19. In yet certain other embodiments, the regulatory cassette may be the CK8 promoter and the CK8 promoter may have 100% sequence identity to the nucleic acid sequence of SEQ ID NO: 19.

In various embodiments, the regulatory cassette may be the cTnT promoter and the cTnT promoter may comprise a portion of the nucleic acid sequence of SEQ ID NO: 1. In various other embodiments, the regulatory cassette may be the cTnT promoter and the cTnT promoter may have at least at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO:1. In yet various other embodiments, the regulatory cassette may be the cTnT promoter and the cTnT promoter may have 100% sequence identity to the nucleic acid sequence of SEQ ID NO: 1.

Another aspect of the disclosure relates to pharmaceutical compositions comprising nucleotide sequences as discussed above. In some embodiments, the pharmaceutical compositions may further include a delivery vehicle. For example, the pharmaceutical compositions may comprise a nucleotide sequence including a regulatory cassette and a micro-dystrophin gene encoding a protein and the pharmaceutical compositions may further comprise a delivery vehicle. The nucleotide sequences of the pharmaceutical compositions may be isolated and purified nucleotide sequences.

In various embodiments, the delivery vehicle may comprise an adeno-associated virus (AAV) vector or a recombinant adeno-associated virus (rAAV) vector. The AAV vector may be a serotype 6 AAV (AAV6). Likewise, the rAAV vector may be a serotype 6 rAAV (rAAV6). The AAV vector may be a serotype 8 AAV (AAV8). Likewise, the rAAV vector may be a serotype 8 rAAV (rAAV8). The AAV vector may be a serotype 9 AAV (AAV9). Likewise, the rAAV vector may be a serotype 9 rAAV (rAAV9). The rAAV vector may be comprised of AAV2 genomic inverted terminal repeat (ITR) sequences pseudotyped with capsid proteins derived from AAV serotype 6 (rAAV2/6). Other suitable serotypes of the AAV or rAAV are also within the scope of this disclosure.

In some embodiments, as discussed above, the delivery vehicle may express, or be configured to express, the micro-dystrophin gene. In various embodiments, the micro-dystrophin gene may include a portion of the nucleic acid sequence of SEQ ID NO:16. In various other embodiments, the micro-dystrophin gene may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO:16. In yet various other embodiments, the micro-dystrophin gene may have 100% sequence identity to the nucleic acid sequence of SEQ ID NO: 16.

In some embodiments, the protein encoded by the micro-dystrophin gene may include a portion of the amino acid sequence of SEQ ID NO:4. In some other embodiments, the protein encoded by the micro-dystrophin gene may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:4. In yet some other embodiments, the protein encoded by the micro-dystrophin gene may have 100% sequence identity to the amino acid sequence of SEQ ID NO:4.

In certain embodiments, the micro-dystrophin gene may include a portion of the nucleic acid sequence of SEQ ID NO: 18. In certain other embodiments, the micro-dystrophin gene may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO:18. In yet certain other embodiments, the micro-dystrophin gene may have 100% sequence identity to the nucleic acid sequence of SEQ ID NO: 18.

In various embodiments, the protein encoded by the micro-dystrophin gene may include a portion of the amino acid sequence of SEQ ID NO:5. In various other embodiments, the protein encoded by the micro-dystrophin gene may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:5. In yet various other embodiments, the protein encoded by the micro-dystrophin gene may have 100% sequence identity to the amino acid sequence of SEQ ID NO:5.

Also, as discussed above, the regulatory cassette may be selected from at least one of a CK8 promoter, a cardiac troponin T (cTnT) promoter, and/or another suitable regulatory cassette. In certain embodiments, the regulatory cassette may be the CK8 promoter and the CK8 promoter may comprise a portion of the nucleic acid sequence of SEQ ID NO:19. In certain other embodiments, the regulatory cassette may be the CK8 promoter and the CK8 promoter may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO:19. In yet certain other embodiments, the regulatory cassette may be the CK8 promoter and the CK8 promoter may have 100% sequence identity to the nucleic acid sequence of SEQ ID NO: 19.

In various embodiments, the regulatory cassette may be the cTnT promoter and the cTnT promoter may comprise a portion of the nucleic acid sequence of SEQ ID NO: 1. In various other embodiments, the regulatory cassette may be the cTnT promoter and the cTnT promoter may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO:1. In yet various other embodiments, the regulatory cassette may be the cTnT promoter and the cTnT promoter may have 100% sequence identity to the nucleic acid sequence of SEQ ID NO: 1.

In some embodiments, the pharmaceutical composition may be configured to reduce a pathological effect or symptom of a muscular dystrophy. The muscular dystrophy may be selected from at least one of myotonic muscular dystrophy, Duchenne muscular dystrophy, Becker muscular dystrophy, limb-girdle muscular dystrophy, facioscapulohumeral muscular dystrophy, congenital muscular dystrophy, oculopharyngeal muscular dystrophy, distal muscular dystrophy, Emery-Dreifuss muscular dystrophy, and/or another suitable muscular dystrophy. In some other embodiments, the pharmaceutical composition may be configured to reduce a pathological effect or symptom of a muscular dystrophy selected from at least one of Duchenne muscular dystrophy and/or Becker muscular dystrophy. In certain embodiments, the pharmaceutical composition may be configured to reduce a pathological effect or symptom of at least one of sarcopenia, heart disease, and/or cachexia.

Another aspect of the disclosure relates to methods for treating a subject having muscular dystrophy, sarcopenia, heart disease, and/or cachexia. The methods may comprise administering to the subject a pharmaceutical composition comprising a micro-dystrophin gene coupled to a regulatory cassette. The methods may comprise administering to the subject a therapeutically effective amount of the pharmaceutical composition. Furthermore, the micro-dystrophin gene may be operably coupled to the regulatory cassette.

In some embodiments, the method may comprise administering to the subject a pharmaceutical composition wherein the pharmaceutical composition further comprises an AAV vector, an rAAV vector, and/or another suitable delivery vehicle. The delivery vehicle may express, or be configured to express, the micro-dystrophin gene in the subject.

As discussed above, in various embodiments, the micro-dystrophin gene may include a portion of the nucleic acid sequence of SEQ ID NO:16. In various other embodiments, the micro-dystrophin gene may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO:16. In yet various other embodiments, the micro-dystrophin gene may have 100% sequence identity to the nucleic acid sequence of SEQ ID NO: 16.

In some embodiments, the protein encoded by the micro-dystrophin gene may include a portion of the amino acid sequence of SEQ ID NO:4. In some other embodiments, the protein encoded by the micro-dystrophin gene may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:4. In yet some other embodiments, the protein encoded by the micro-dystrophin gene may have 100% sequence identity to the amino acid sequence of SEQ ID NO:4.

In certain embodiments, the micro-dystrophin gene may include a portion of the nucleic acid sequence of SEQ ID NO:18. In certain other embodiments, the micro-dystrophin gene may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO:18. In yet certain other embodiments, the micro-dystrophin gene may have 100% sequence identity to the nucleic acid sequence of SEQ ID NO:18.

In various embodiments, the protein encoded by the micro-dystrophin gene may include a portion of the amino acid sequence of SEQ ID NO:5. In various other embodiments, the protein encoded by the micro-dystrophin gene may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO:5. In yet various other embodiments, the protein encoded by the micro-dystrophin gene may have 100% sequence identity to the amino acid sequence of SEQ ID NO:5.

In some embodiments, the regulatory cassette may express, or be configured to express, the micro-dystrophin gene such that a level of expression of the micro-dystrophin gene is at least 100-fold higher in striated muscle cells than the level of expression of the micro-dystrophin gene in non-muscle cells. For example, the level of expression of the micro-dystrophin gene may be at least 100-fold higher in the striated muscle cells of the subject than in lung cells of the subject. In some other embodiments, the regulatory cassette may express, or be configured to express, the micro-dystrophin gene such that a level of expression of the micro-dystrophin gene is between at least 50-fold higher and 150-fold higher, between at least 75-fold higher and 125-fold higher, or between at least 90-fold higher and 110-fold higher in striated muscle cells than the level of expression of the micro-dystrophin gene in non-muscle cells.

As discussed above, the regulatory cassette may be selected from at least one of a CK8 promoter, a cardiac troponin T (cTnT) promoter, and/or another suitable regulatory cassette. In certain embodiments, the regulatory cassette may be the CK8 promoter and the CK8 promoter may comprise a portion of the nucleic acid sequence of SEQ ID NO:19. In certain other embodiments, the regulatory cassette may be the CK8 promoter and the CK8 promoter may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO:19. In yet certain other embodiments, the regulatory cassette may be the CK8 promoter and the CK8 promoter may have 100% sequence identity to the nucleic acid sequence of SEQ ID NO: 19.

In various embodiments, the regulatory cassette may be the cTnT promoter and the cTnT promoter may comprise a portion of the nucleic acid sequence of SEQ ID NO: 1. In various other embodiments, the regulatory cassette may be the cTnT promoter and the cTnT promoter may have at least 20%, at least 30%, at least 40%, at least 50%, at least 60%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence of SEQ ID NO:1. In yet various other embodiments, the regulatory cassette may be the cTnT promoter and the cTnT promoter may have 100% sequence identity to the nucleic acid sequence of SEQ ID NO: 1.

In some embodiments, the micro-dystrophin gene may express, or be configured to express, a micro-dystrophin protein in one or more muscles of the subject such that contractility of the one or more muscles is enhanced or increased. In certain embodiments, the micro-dystrophin gene may express, or be configured to express, a micro-dystrophin protein in one or more skeletal muscles of the subject such that a specific-force generating capacity of at least one of the one or more skeletal muscles is enhanced or increased to within at least 10%, at least 20%, at least 30%, or at least 40% of a normal specific-force generating capacity. In certain other embodiments, the micro-dystrophin gene may express, or be configured to express, a micro-dystrophin protein in one or more cardiac muscles of the subject such that a baseline end-diastolic volume defect is restored to within at least 10%, at least 20%, at least 30%, or at least 40% of a normal end-diastolic volume. In various embodiments, the micro-dystrophin gene may express, or be configured to express, a micro-dystrophin protein such that localization of the neuronal nitric oxide synthase to the dystrophin-glycoprotein complex is enhanced or increased in the subject.

In some embodiments, as discussed above, the methods may comprise treating a subject having at least one of myotonic muscular dystrophy, Duchenne muscular dystrophy, Becker muscular dystrophy, limb-girdle muscular dystrophy, facioscapulohumeral muscular dystrophy, congenital muscular dystrophy, oculopharyngeal muscular dystrophy, distal muscular dystrophy, Emery-Dreifuss muscular dystrophy, and/or another suitable muscular dystrophy. In some other embodiments, the methods may comprise treating a subject having at least one of Duchenne muscular dystrophy and/or Becker muscular dystrophy.

In certain embodiments, the pharmaceutical composition may reduce, or be configured to reduce, a pathological effect or symptom of the muscular dystrophy, sarcopenia, heart disease, and/or cachexia. The pathological effect or symptom of the muscular dystrophy may be selected from at least one of muscle pain, muscle weakness, muscle fatigue, muscle atrophy, fibrosis, inflammation, increase in average myofiber diameter in skeletal muscle, cardiomyopathy, reduced 6-minute walk test time, loss of ambulation, cardiac pump failure, and/or one or more other suitable pathological effects or symptoms. The pathological effect or symptom of sarcopenia may be selected from at least one of muscle wasting and/or muscle weakness. The pathological effect or symptom of heart disease may be selected from at least one of cardiomyopathy, reduced hemodynamics, and/or arrhythmia. The pathological effect or symptom of cachexia may be selected from at least one of muscle wasting and/or muscle weakness.

The methods of treating a subject having muscular dystrophy may further comprise identifying a subject having muscular dystrophy. Similarly, the methods of treating a subject having sarcopenia, heart disease, and/or cachexia may further comprise identifying a subject having sarcopenia, heart disease, and/or cachexia, respectively. In some embodiments, the subject may be a mammal. In certain embodiments, the subject may be a human.

Another aspect of the disclosure relates to methods for prophylactically treating a subject at risk of developing muscular dystrophy, sarcopenia, heart disease, and/or cachexia. The methods may comprise administering to the subject a pharmaceutical composition as described above in reference to the methods of treating a subject having a muscular dystrophy, sarcopenia, heart disease, and/or cachexia.

In some embodiments, the methods may comprise treating a subject at risk of developing at least one of myotonic muscular dystrophy, Duchenne muscular dystrophy, Becker muscular dystrophy, limb-girdle muscular dystrophy, facioscapulohumeral muscular dystrophy, congenital muscular dystrophy, oculopharyngeal muscular dystrophy, distal muscular dystrophy, Emery-Dreifuss muscular dystrophy, and/or another suitable muscular dystrophy. In some other embodiments, the methods may comprise treating a subject at risk of developing at least one of Duchenne muscular dystrophy and/or Becker muscular dystrophy.

In certain embodiments, the pharmaceutical composition may reduce, or be configured to reduce, a risk of developing a pathological effect or symptom of a muscular dystrophy, sarcopenia, heart disease, and/or cachexia. The methods of treating a subject at risk of developing muscular dystrophy, sarcopenia, heart disease, and/or cachexia may further comprise identifying a subject at risk of developing muscular dystrophy, sarcopenia, heart disease, and/or cachexia, respectively. In some embodiments, the subject may be a mammal. In certain embodiments, the subject may be a human.

Another aspect of the disclosure relates to regulatory cassettes including enhancers and/or promoters that enhance and/or target expression of a pharmaceutical composition (e.g., a micro-dystrophin gene). In some embodiments, the enhancers or promoters for enhancing and/or targeting expression of a pharmaceutical composition may include at least a portion of a gene, a peptide, a polypeptide, and/or a regulatory RNA. Targeting expression of the pharmaceutical composition may include expression the pharmaceutical composition in a specific cell type, tissue, and/or organ of a subject. For example, cTnT455 (SEQ ID NO:1) may be used for cardiac-specific expression.

In certain embodiments, the enhancers or promoters may express, or be configured to express, a pharmaceutical composition comprising a peptide. In various embodiments, the enhancers or promoters may express, or be configured to express, the peptide in developing, injured, and/or diseased muscle (i.e., muscle that may be undergoing regeneration). The hum-cTnT455 RC (SEQ ID NO:1) may not be transcriptionally active in steady state mature skeletal muscle.

As discussed above, the enhancers and/or promoters may be operatively linked to a pharmaceutical composition, i.e., for enhancing expression and/or targeting of the pharmaceutical composition. Additionally, the pharmaceutical composition may be operatively linked to one or enhancers and/or promoters. In some embodiments, expression of the pharmaceutical compositions disclosed herein may assist in regenerating cardiac muscle. For example, the hum-cTnT455 RC (SEQ ID NO:1) may enhance or target the transient expression of the pharmaceutical composition in wounded and/or regenerating cardiac muscle. In some embodiments, expression of the pharmaceutical compositions disclosed herein may assist in preventing loss of cardiac muscle and/or of cardiomyocytes. In certain embodiments, expression of the pharmaceutical compositions disclosed herein may assist in regenerating skeletal muscle. In various embodiments, expression of the pharmaceutical compositions disclosed herein may assist in preventing necrosis and/or wasting of skeletal muscle.

Another aspect of the disclosure relates to nucleotide sequences comprising a micro-dystrophin gene, wherein the micro-dystrophin gene may encode a protein comprising at least two spectrin-like repeats that are directly coupled to each other. In some embodiments, the at least two spectrin-like repeats that are directly coupled to each other may be selected from at least one of a spectrin-like repeat 1 (SR1) directly coupled to a spectrin-like repeat 2 (SR2), an SR2 directly coupled to a spectrin-like repeat 3 (SR3), an SR1 directly coupled to a spectrin-like repeat 16 (SR16), a spectrin-like repeat 17 (SR17) directly coupled to a spectrin-like repeat 23 (SR23), an SR17 directly coupled to a spectrin-like repeat 24 (SR24), and/or an SR23 directly coupled to an SR24. The micro-dystrophin gene may also encode a protein comprising an amino-terminal actin-binding domain and/or a β-dystroglycan binding domain.

Another aspect of the disclosure relates to nucleotide sequences comprising a micro-dystrophin gene, wherein the micro-dystrophin gene may encode a protein comprising, in order, a Hinge 1 domain (H1), an SR1, an SR16, an SR17, an SR24, and/or a Hinge 4 domain (H4). In some embodiments, the H1 may be directly coupled to the SR1. In various embodiments, the SR 1 may be directly coupled to the SR16. In certain embodiments, the SR16 may be directly coupled to the SR17. In some embodiments, the SR17 may be directly coupled to the SR24. In various embodiments, the SR24 may be directly coupled to the H4.

In some embodiments, the protein encoded by the micro-dystrophin gene may further comprise, in order, an SR2 and an SR3, wherein the SR2 and the SR3 may be disposed between the SR1 and the SR16. Furthermore, the SR1 may be directly coupled to the SR2 and the SR2 may be further coupled to the SR3.

Another aspect of the disclosure relates to nucleotide sequences comprising a micro-dystrophin gene encoding a protein, wherein the micro-dystrophin gene may encode a protein comprising, in order, a H1, an SR1, an SR16, an SR17, an SR 23, an SR24, and/or a H4. In some embodiments, the H1 may be directly coupled to the SR1, the SR1 may be directly coupled to the SR 16, the SR 16 may be directly coupled to the SR 17, the SR 17 may be directly coupled to the SR 23, the SR 23 may be directly coupled to the SR 24, and/or the SR 24 may be directly coupled to the H4.

Another aspect of the disclosure relates to pharmaceutical compositions that may comprise a micro-dystrophin gene comprising the nucleic acid sequence of SEQ ID NO:16 and an adeno-associated virus (AAV) vector or a recombinant adeno-associated virus (rAAV) vector. In some embodiments, a serotype of the AAV vector or the rAAV vector may selected from at least one of serotype 6, serotype 8, serotype 9, or another suitable serotype.

Another aspect of the disclosure relates to pharmaceutical composition that may comprise a micro-dystrophin gene encoding a protein, wherein the protein may comprise the amino acid sequence of SEQ ID NO:4 and an AAV vector or an rAAV vector. In certain embodiments, a serotype of the AAV vector or the rAAV vector may be selected from at least one of serotype 6, serotype 8, serotype 9, or another suitable serotype.

Another aspect of the disclosure relates to pharmaceutical compositions that may comprise a micro-dystrophin gene comprising the nucleic acid sequence of SEQ ID NO:18 and an AAV vector or an rAAV vector. In various embodiments, a serotype of the AAV vector or the rAAV vector is selected from at least one of serotype 6, serotype 8, serotype 9, or another suitable serotype.

Another aspect of the disclosure relates to pharmaceutical compositions that may comprise a micro-dystrophin gene encoding a protein, wherein the protein may comprise the amino acid sequence of SEQ ID NO:5 and an AAV vector or an rAAV vector. In some embodiments, a serotype of the AAV vector or the rAAV vector is selected from at least one of serotype 6, serotype 8, serotype 9, or another suitable serotype.

Another aspect of the disclosure relates to pharmaceutical compositions for use in the treatment or prophylactic treatment of muscular dystrophy, sarcopenia, heart failure, and/or cachexia. In some embodiments, the pharmaceutical compositions may comprise a micro-dystrophin gene. In certain embodiments, the micro-dystrophin gene may comprise the nucleic acid sequence of SEQ ID NO: 16 or SEQ ID NO:18 and an AAV vector or an rAAV vector. In various embodiments, a serotype of the AAV vector or the rAAV vector may be selected from at least one of serotype 6, serotype 8, serotype 9, or another suitable serotype.

Another aspect of the disclosure relates to pharmaceutical compositions for the treatment or prophylactic treatment of muscular dystrophy sarcopenia, heart failure, and/or cachexia. In some embodiments, the pharmaceutical compositions may comprise a micro-dystrophin gene. In certain embodiments, the micro-dystrophin gene may comprise the nucleic acid sequence of SEQ ID NO: 16 or SEQ ID NO: 18 and an AAV vector or an rAAV vector. In various embodiments, a serotype of the AAV vector or the rAAV vector may be selected from at least one of serotype 6, serotype 8, serotype 9, or another suitable serotype.

EXAMPLES

The following examples are illustrative of disclosed methods and compositions. In light of this disclosure, those of skill in the art will recognize that variations of these examples and other examples of the disclosed methods and compositions would be possible without undue experimentation.

Example 1—Development of Micro-Dystrophins

To develop micro-dystrophins with improved performance a variety of structural modifications of the dystrophin central rod domain, which accounts for approximately 80% of the coding region, were assessed. Novel constructs were generated that comprise unique combinations of between four and six of the 24 spectrin-like repeats (SRs) present in the full-length protein as well as the presence or absence of internal hinge domains. These novel micro-dystrophins were evaluated by rAAV-mediated delivery to dystrophic mdx mice followed by pathophysiologic analysis of skeletal muscles after three and six months.

Several versions of μDys clones were designed with a focus on increasing functional activity while allowing more complete restoration of the dystrophin glycoprotein complex (DGC). The designed μDys clones were compared with a previously characterized ΔH2-R23+H3/ΔCT clone, μDysH3, which can be highly functional in striated muscles of mdx mice (see Banks, G. B., et al., PLOS Genetics 6, e1000958, (2010)). The design of these constructs focused, at least in part, on the central rod domain in efforts to improve the contractility of muscles expressing the constructs and to restore neuronal nitric oxide synthase (nNOS) localization to the DGC (see Lai, Y., et al., The Journal of Clinical Investigation 119, 624-635, (2009) and Lai, Y., et al., Proceedings of the National Academy of Sciences of the United States of America 110, 525-530, (2013)). Also tested, were the functional capacity and the ability to deliver larger constructs carrying 4, 5, or 6 SRs. To allow stable packaging of these larger μDys clones, a small gene regulatory cassette (RC) modified from the muscle creatine kinase gene was incorporated. This CK8 RC can display strong, muscle-restricted expression, yet this CK8 RC is less than 500 bps in size (see Goncalves, M. A., et al., Molecular Therapy: The Journal of the American Society of Gene Therapy 19, 1331-1341, (2011) and Martari, M., et al., Human Gene Therapy 20, 759-766, (2009)).

Example 2—Design of Micro-Dystrophin Clones

Seven novel micro-dystrophin (μDys) clones were designed to test variations of the rod domain structure. Each of the seven micro-dystrophin clones retained coding sequences for the N-terminal actin-binding domain (N-ABD) and the dystroglycan-binding domain (Dg BD), however, each μDys clone incorporated novel combinations of SR and hinge domains, with a goal of generating μDys clones with improved functional properties that may be delivered and expressed from an rAAV vector. Each of the μDys clones were also tested in a mouse model for Duchenne muscular dystrophy (DMD), as described below. The SEQ ID NOs of the amino acid sequences and nucleic acid sequences of μDysH3 and these seven novel μDys constructs are listed in Table 1.

TABLE 1

Micro-dystrophin Construct Sequences

| Micro-dystrophin Construct | Amino Acid Sequence | Nucleic Acid Sequence |
|---|---|---|
| μDysH3 | SEQ ID NO: 3 | SEQ ID NO: 11 |
| μDys1 | SEQ ID NO: 6 | SEQ ID NO: 12 |
| μDys2 | SEQ ID NO: 7 | SEQ ID NO: 13 |
| μDys3 | SEQ ID NO: 8 | SEQ ID NO: 14 |
| μDys4 | SEQ ID NO: 9 | SEQ ID NO: 15 |
| μDys5 | SEQ ID NO: 4 | SEQ ID NO: 16 |
| μDys6 | SEQ ID NO: 10 | SEQ ID NO: 17 |
| μDys7 | SEQ ID NO: 5 | SEQ ID NO: 18 |

Previous studies suggest that the choice of hinge domains within a μDys clone can impact the function of the protein (see Banks, G. B., et al., PLOS Genetics 6, e1000958, (2010)). It was assessed whether alternative and/or shorter hinge domains could be substituted for the Hinge 3 domain, which was used in the μDys clone, μDysH3 (see id.). It has been indicated that inclusion of SRs 16 and 17 can improve the function of some μDys clones (e.g., by recruiting nNOS to the DGC). Accordingly, SRs 16 and 17 were also tested in the context of various hinge domains and other SRs. Creation of novel junctions was also minimized (i.e., junctions wherein domains not normally adjacent to one another in the full-length protein are brought together). Additionally, the effect of the inclusion of combinations of either 5 or 6 SRs on μDys-clone function was also assessed. The structure of the seven novel μDys clones, in comparison to the μDysH3 clone and the full-length protein, are illustrated in FIG. 1A.

Figure 21:
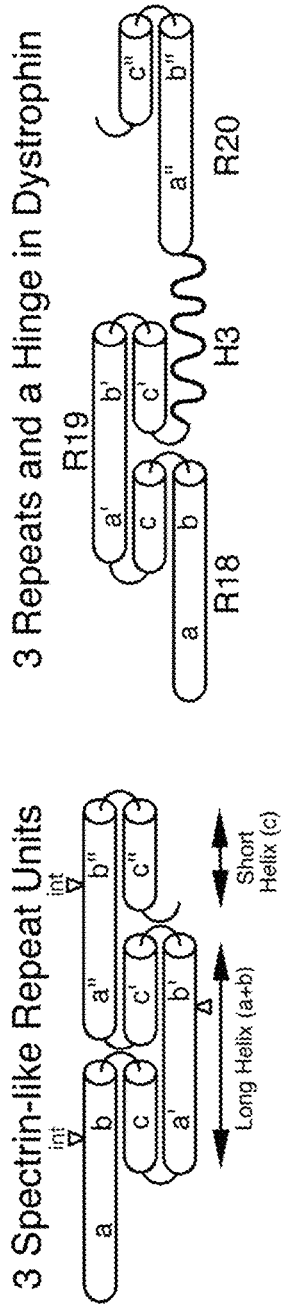
FIG. 21 is a series of schematic illustrations of the structure of dystrophin spectrin-like repeats and the juxtaposition with hinge domains. Top left, interdigitated folding of individual spectrin-like repeats is illustrated to show how 3 adjacent repeats can fold together, with the different alpha-helical segments highlighted (a, b, c; a', b', c'; and a", b", c" representing the helical domains of the three different spectrin-like repeats). Top right, in native dystrophin and utrophin, some spectrin-like repeats are separated by hinge domains that disrupt the normal interdigitated folding of adjacent spectrin-like repeats. Shown at the top right is the folding pattern of Spectrin-like repeats 18, 19, and 20 and their separation by Hinge 3. Middle left, Optimized miniand micro-dystrophins typically display maximal functional activity when the spectrin-like repeats domains are arranged in such a way as to preserve normal folding patterns; this normal folding is disrupted when non-integral units of spectrin-like repeats are present in a mini- or micro-dystrophin proteins, such as when a natural occurring deletion that removes whole exons occurs in a Becker muscular dystrophy patient. This latter situation is illustrated in the schematic illustration at the middle right, which represents the predicted structure of the junctional domain of dystrophin from a patient with a genomic deletion removing exons 17-48. The bottom schematic illustrations show the folding pattern predicted in the µDysH2 (left) and µDysH3 (right) proteins, and also illustrate the unpredictable nature of the functional activity of miniaturized dystrophin proteins. While µDysH2 and µDysH3 have similar folding patterns, µDysH2 leads to ringbinden when expressed in mdx mouse skeletal muscles, whereas µDysH3 does not lead to ringbinden (see Banks, G. B., et al., PLOS Genetics 6, e1000958, (2010)).
Figure 21:
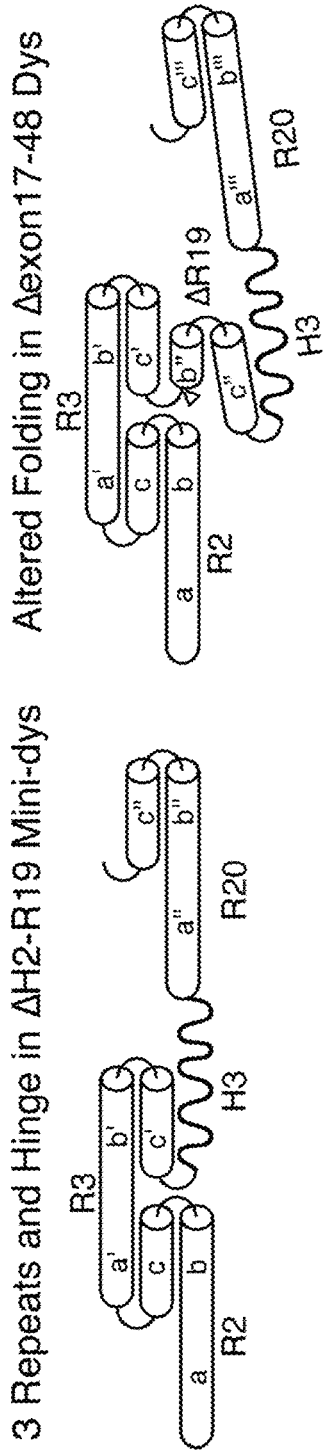
Figure 21:
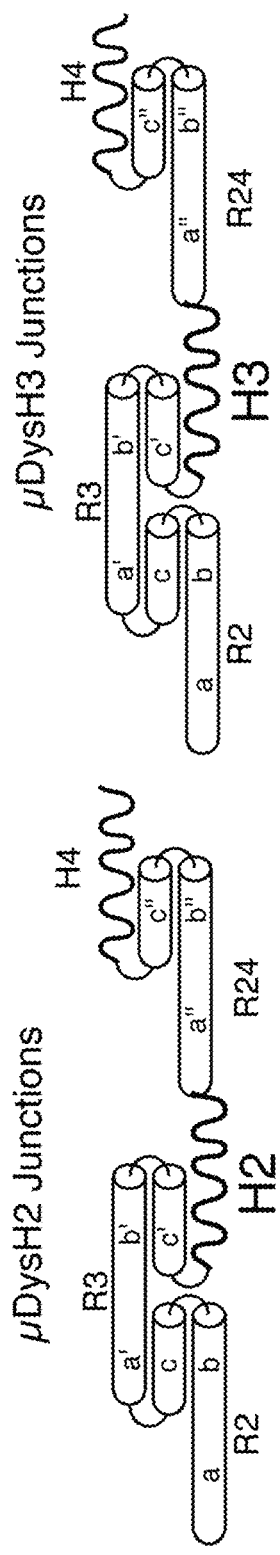

Two regions in the dystrophin were tested for their ability to substitute for Hinge 3. The hinge regions of the rod domain are proline rich and lack alpha-helical signature motifs that compose the triple-helical coiled-coil of a spectrin-like repeat (see Winder, S. J., et al., FEBS Letters 369, 27-33 (1995)). SR23 contains a proline-rich linker between alpha-helices b and c (see, e.g., FIG. 21). It was assessed if this sequence (with alpha-helix c of SR23) could be used as a hinge domain either by itself (μDys1), adjoining SR16-17 (μDys2), or together with H3 (μDys4). One additional construct replaced Hinge 3 with the entire SR23 (μDys5; see FIG. 1A). A second hinge-like region (SEQ ID NO:20) composed of a 20 amino acid insertion previously noted to be located between SR15 and SR16 was also tested (μDys6) (see Winder, S. J., et al., FEBS Letters 369, 27-33 (1995)). Additional constructs were designed to test various combinations of the SR domains in the context of these hinges. It has been suggested that the context of SR domains can be important for their function, as such, it was tested whether a hybrid SR, composed of the first half of SR20 and the final half of SR24, would improve μDys function (μDys3). This hybrid SR merges the portion of SR20 normally adjacent to Hinge 3 with the portion of SR24 that merges into Hinge 4 (see FIG. 1A). Similar considerations influenced the design of the μDys6 construct noted above, where the novel hinge located between SR15 and SR16 was used in its normal context adjacent to the nNOS location region in SR16-17. This latter construct was also compared directly with a similar construct but which used Hinge 3 instead of the short hinge-like region from between SR15 and SR16 (see FIG. 1B). It was also noted that μDys clones 5-7, which incorporate either 5 or 6 SR domains, potentially increase the overall function of the protein (see Harper, S. Q. et al., Nature Medicine 8, 253-261, (2002)).

Example 3—Functionality of Partial Spectrin-Like Repeats can be Dependent on the Rod Domain Composition An initial functional screen of μDys clones 1-7 was made in comparison to the μDysH3 clone by generating rAAV6 vectors regulated by the CMV promoter. A dose of $5 \times 10^{10}$ vector genomes (vg) was intramuscularly injected into one tibialis anterior (TA) muscle of 5-6 week old dystrophic mdx$^{4cv}$ male mice (see Chapman, V. M., et al., Proceedings of the National Academy of Sciences of the United States of America 86, 1292-1296 (1989)), with the contralateral muscle serving as an internal negative control (N=4-5 mice per construct).

Figure 1C:
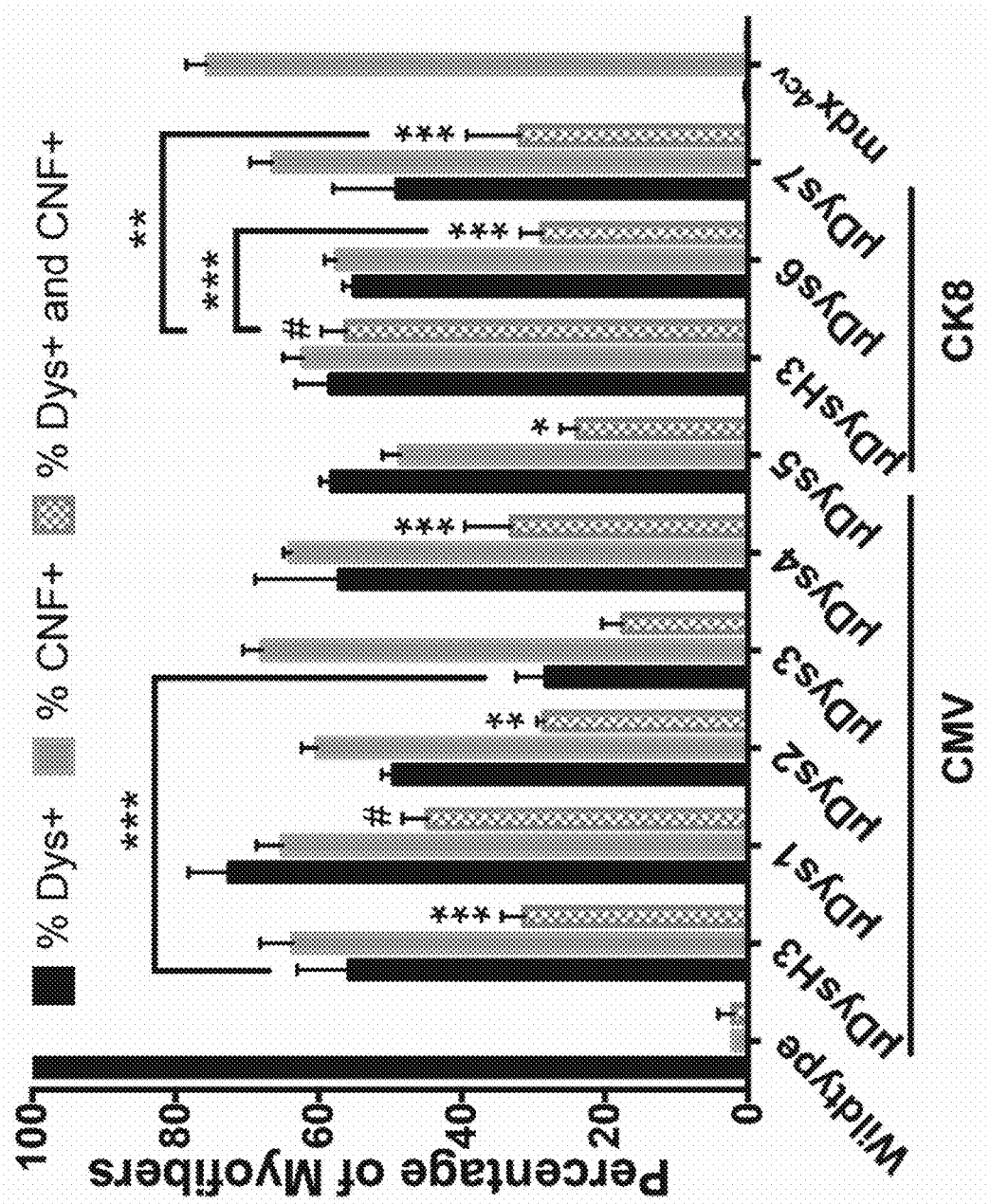
FIGS. 1C and 1D are graphs depicting quantification of myofibers from TA cross sections for dystrophin expression and central nucleation at 4 or 12 weeks post-treatment, respectively (N=3-5 per cohort for each time point, mean±S.E.M.). µDysH3 served as a comparative gauge of performance. µDys6 and µDys7 were too large to be cloned into AAV-expression vectors using the ubiquitous cytomegalovirus (CMV) promoter, consequently, the CMV promoter was replaced with the myogenic-specific CK8 promoter to allow efficient packaging and in vivo evaluation. Accordingly, µDysH3 was re-evaluated with the CK8 regulatory expression cassette. Characters denote significance from wild type mice. *$P<0.05$, $P<0.01$, *$P<0.001$, #$P<0.0001$.
Figure 1D:
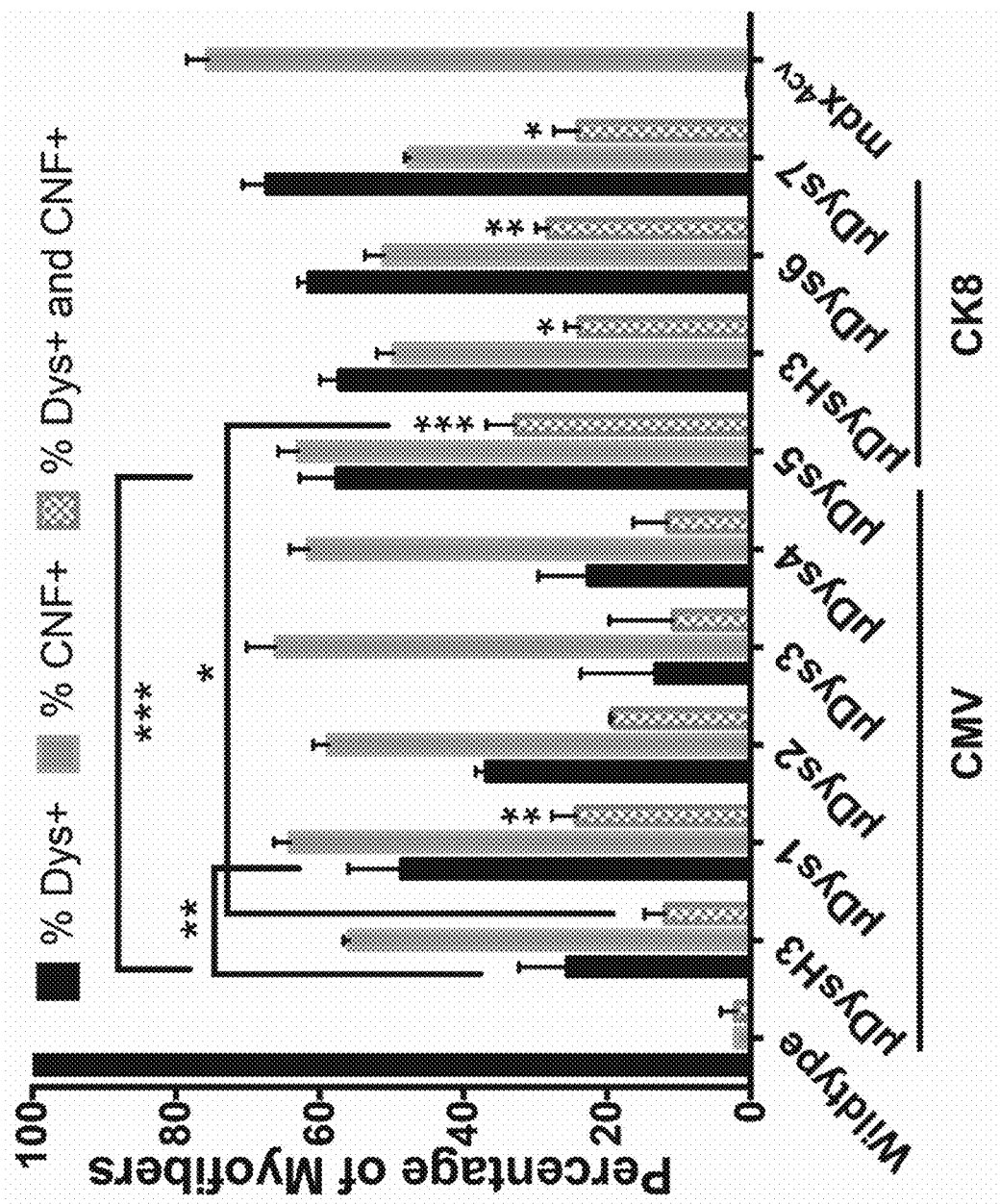

Dystrophin expression and central nucleation, a hallmark of degeneration/regeneration, was measured at 4 weeks and 12 weeks post-injection (see FIGS. 1C and 1D) to determine how well each construct was expressed, whether expression persisted, and whether the constructs were able to prevent or reduce ongoing myofiber necrosis. All constructs generated μDys proteins of the predicted sizes, as shown by Western blot analysis (see FIG. 1B). At this age and vector dose per injected TA muscle, all treated mdx$^{4cv}$ cohorts had significantly fewer dystrophin-positive (Dys+) myofibers compared to wild type C57BL/6 mice (P<0.001), yet differences of functionality were observed among the micro-dystrophins. Constructs μDys3 and μDys4 performed less well than μDysH3, as evidenced by a reduction in dystrophin-positive myofibers between 4 and 12 weeks post-injection. Constructs μDys-1, 2, and 5 exhibited more dystrophin-positive myofibers than μDysH3 by 12 weeks post-injection (see FIG. 1D). An initial screen of μDys6 and μDys7 was made against μDysH3 driven by the CK8 promoter. Both the new constructs generated comparable levels of transduced (Dys+) and centrally nucleated (CNF+) myofibers by 12 weeks post-injection relative to μDysH3 (see FIG. 1D). Myofibers exhibiting both dystrophin expression and central nucleation were quantified at both time points (see FIGS. 1C and 1D). Levels of Dys+ and CNF+myofibers decreased from 4 to 12 weeks post-injection in the treated cohorts, yet remained higher than in wild type muscles. Whether this was the result of poor functionality or sub-optimal dose of a micro-dystrophin construct remained uncertain with the initial screen alone, which prompted a systemic administration for further evaluation.

Figure 2:
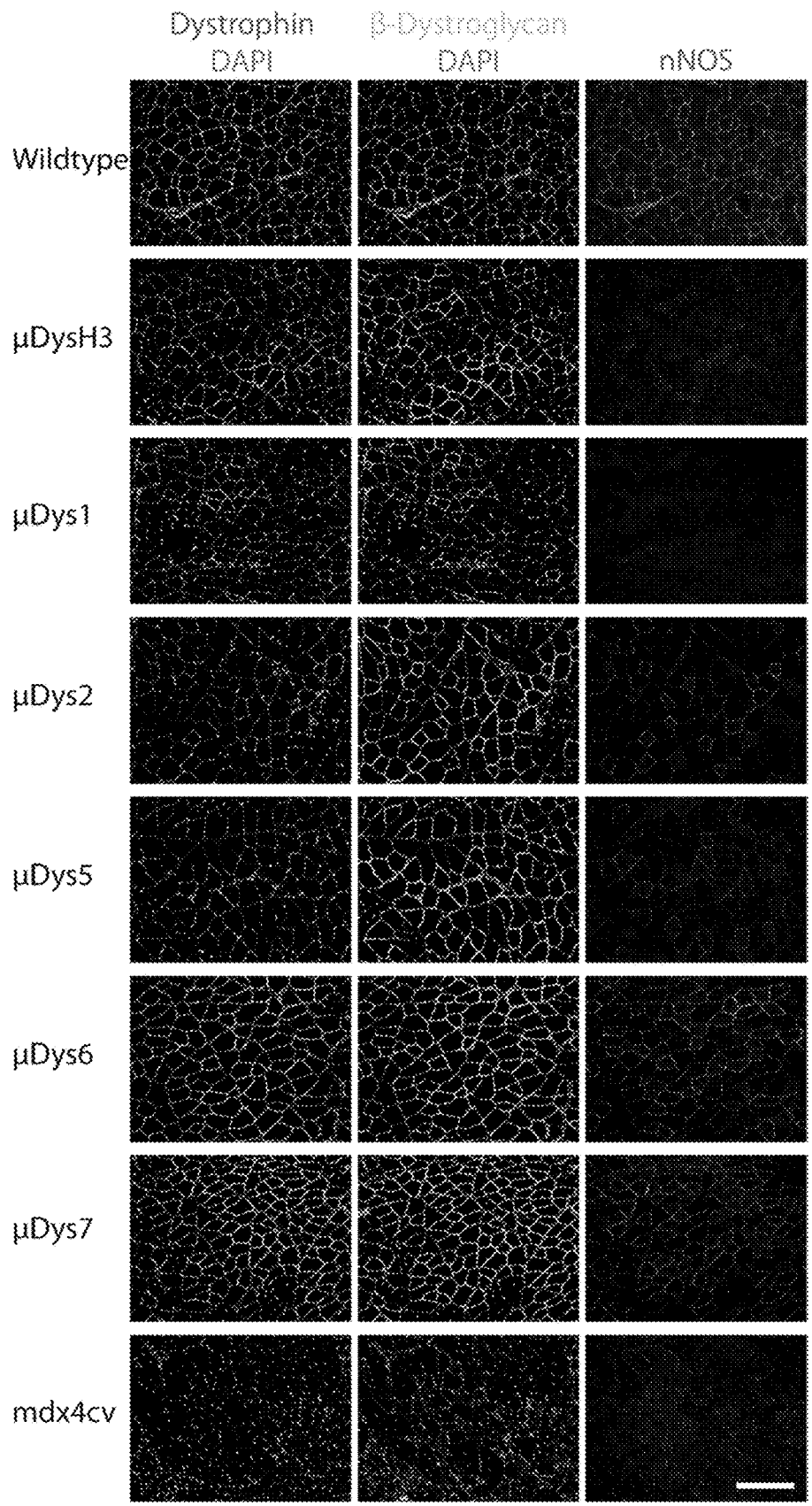
FIG. 2 is a series of micrographs depicting representative gastrocnemius cross sections at six months post-treatment. Dystrophin and DAPI-stained nuclei are shown in the left column, β-dystroglycan and DAPI are shown in the middle column, and neuronal nitric oxide synthase (nNOS) is shown in the right column, as indicated. Each row depicts representative results from cohorts of wild type, treated mdx$^{4cv}$, and untreated mdx$^{4cv}$ mice. Scale bar, 200 µm. Recruitment of dystrophin glycoprotein complex (DGC) members is generally dependent on binding domains within µDys constructs. Dystrophic mdx$^{4cv}$ mice were injected retro-orbitally with $1\times10^{13}$ vg of rAAV6/CK8-µDys at 14 days of age. Three and six months post-treatment, skeletal muscles were immunostained for DGC members.

Example 4—Novel μDys Constructs Attenuate Pathology in Respiratory and Hind Limb Skeletal Muscles The μDys-1, 2, 3, 4, 5, and μDysH3 vectors were recloned to replace the CMV with the smaller and muscle-specific CK8 promoter, enabling a direct comparison with the larger six SR-containing constructs (μDys6 and 7). For systemic treatment, a bolus of $10^{13}$ vg was delivered to 14-day old mdx$^{4cv}$ male mice via retro-orbital injection. Treated mice were assessed at either 3 or 6 months post-injection, along with age matched untreated and wild type controls. This experiment was designed to monitor expression of the μDys constructs and assess the relative extent to which they may halt dystrophic pathophysiology. Persistence of μDys expression was measured by immunofluorescence staining of gastrocnemius muscle and diaphragm muscle cryosections. The recruitment of DGC members, β-dystroglycan and nNOS (for applicable constructs), to the sarcolemma was also verified (see FIG. 2).

Figure 3A:
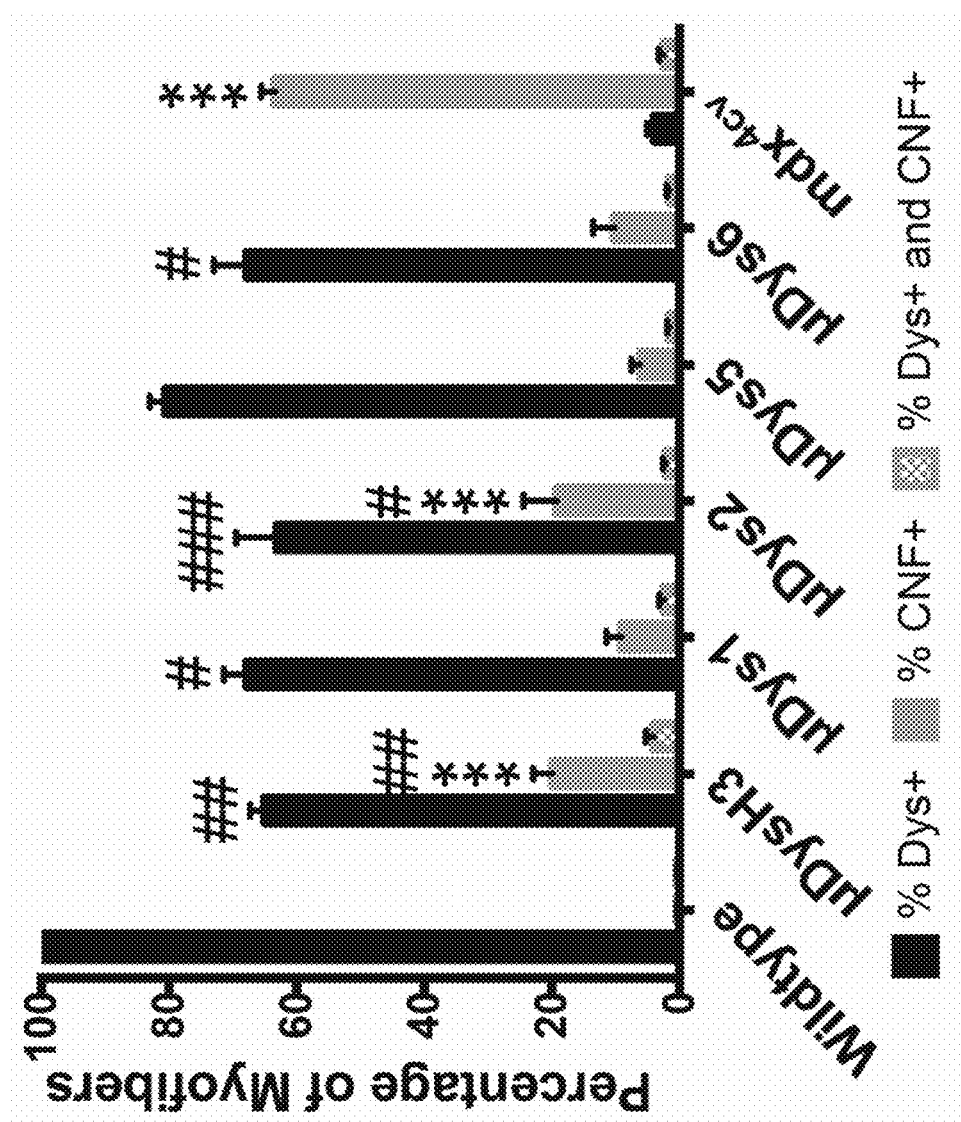
FIGS. 3A-3D are graphs depicting evaluation of systemic treatment at 3 months post-treatment. Gastrocnemius muscles (FIGS. 3A and 3B) and diaphragm muscles (FIGS. 3C and 3D) were evaluated to determine the performance of novel µDys constructs. Muscle cross sections were quantified for dystrophin expression and centrally nucleated myofibers. Levels of myofibers exhibiting dystrophin expression and/or exhibiting central nucleation are represented as percentages (FIGS. 3A and 3C). Specific force generation was measured in situ for gastrocnemius (FIG. 3B) and in vitro for diaphragm strips (FIG. 3D). The n value for each cohort is listed in columns of FIG. 3D. For non-bracketed characters, *$P<0.05$, $P<0.01$, *$P<0.001$ from wild type. ˆ$P<0.05$, ^^P<0.01, ^^^P<0.001 from µDys2-treated mice. #P<0.05, ##P<0.01, ###P<0.001 from µDys5-treated mice.
Figure 3B:
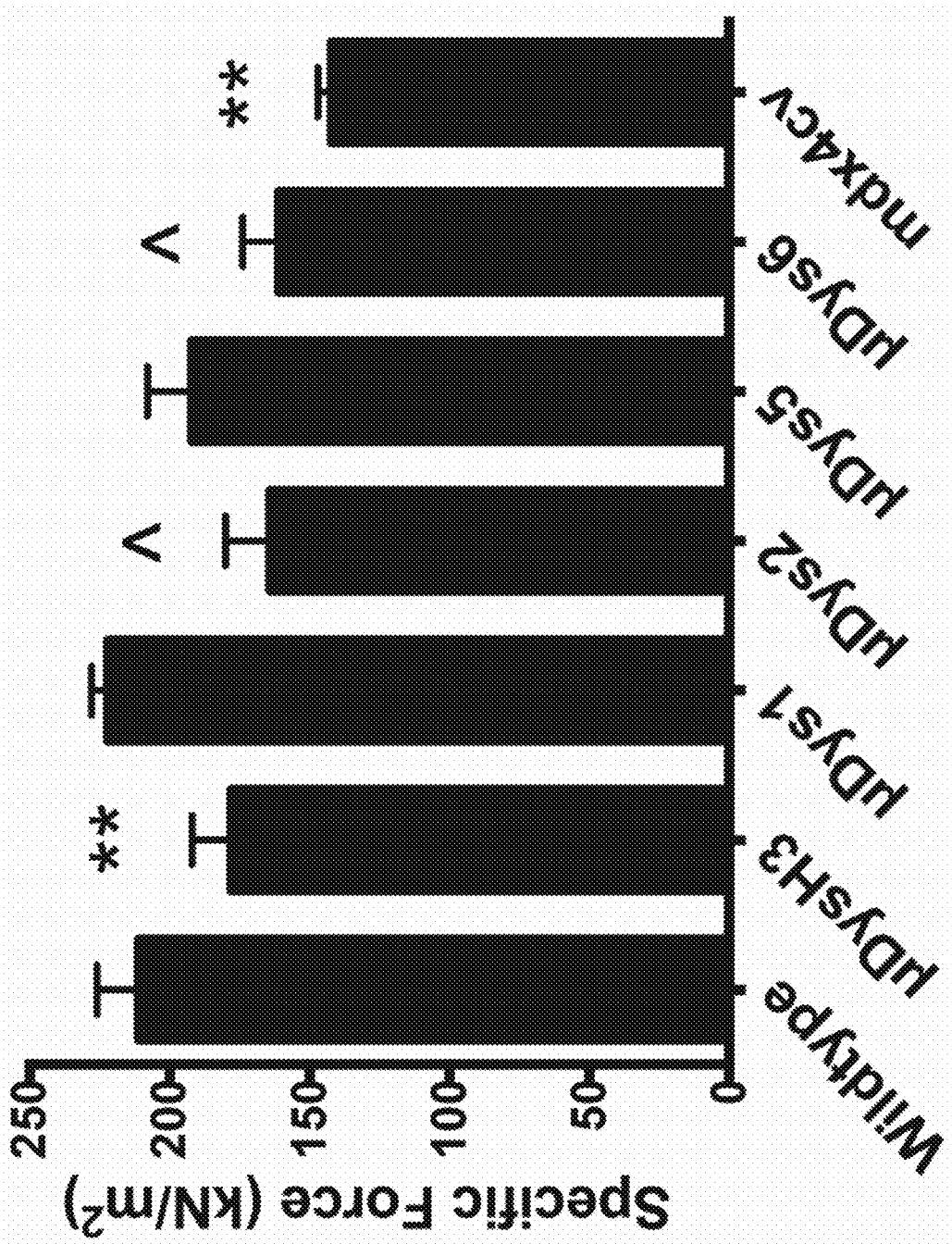
Figure 3C:
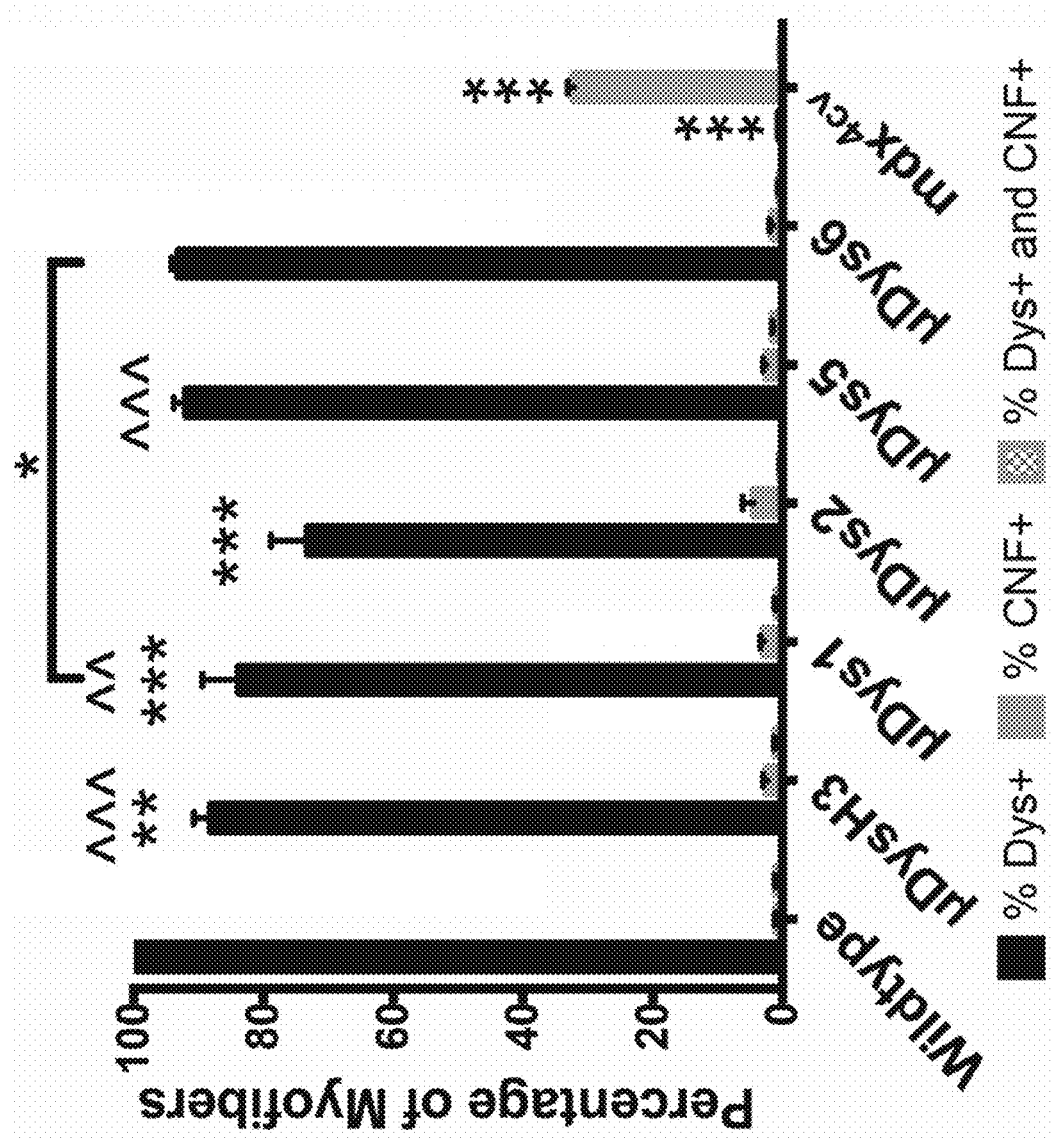

At three months post-injection, all treated groups had greater than 60% expression of dystrophin at the sarcolemma in both the gastrocnemius and diaphragm myofibers. The percentage of dystrophin-positive myofibers that were centrally nucleated was not significantly different from wild type controls (see FIGS. 3A and 3C). At this time point, μDys2 was observed to be expressed at significantly lower levels compared with μDys5 in the gastrocnemius and the diaphragm (see FIGS. 3A and 3C). The μDys2 treated mice also had significantly fewer transduced myofibers in the diaphragm compared to μDys1, μDys5, and μDysH3 injected animals (see FIG. 3C). Conversely, μDys5 injected mice displayed significantly higher numbers of transduced myofibers in the gastrocnemius compared with all other treated groups (see FIG. 3A). Morphological analysis of the same muscles demonstrated that all treated groups had significantly reduced percentages of centrally nucleated myofibers. In the diaphragm, there were no significant differences in the percentages of centrally nucleated myofibers between the wild type and treated groups. However, μDys2 and μDysH3 injected mice displayed significantly higher levels of central nucleation (19% and 20%, respectively; P<0.001) than wild type (0%) in the gastrocnemius.

Figure 3D:
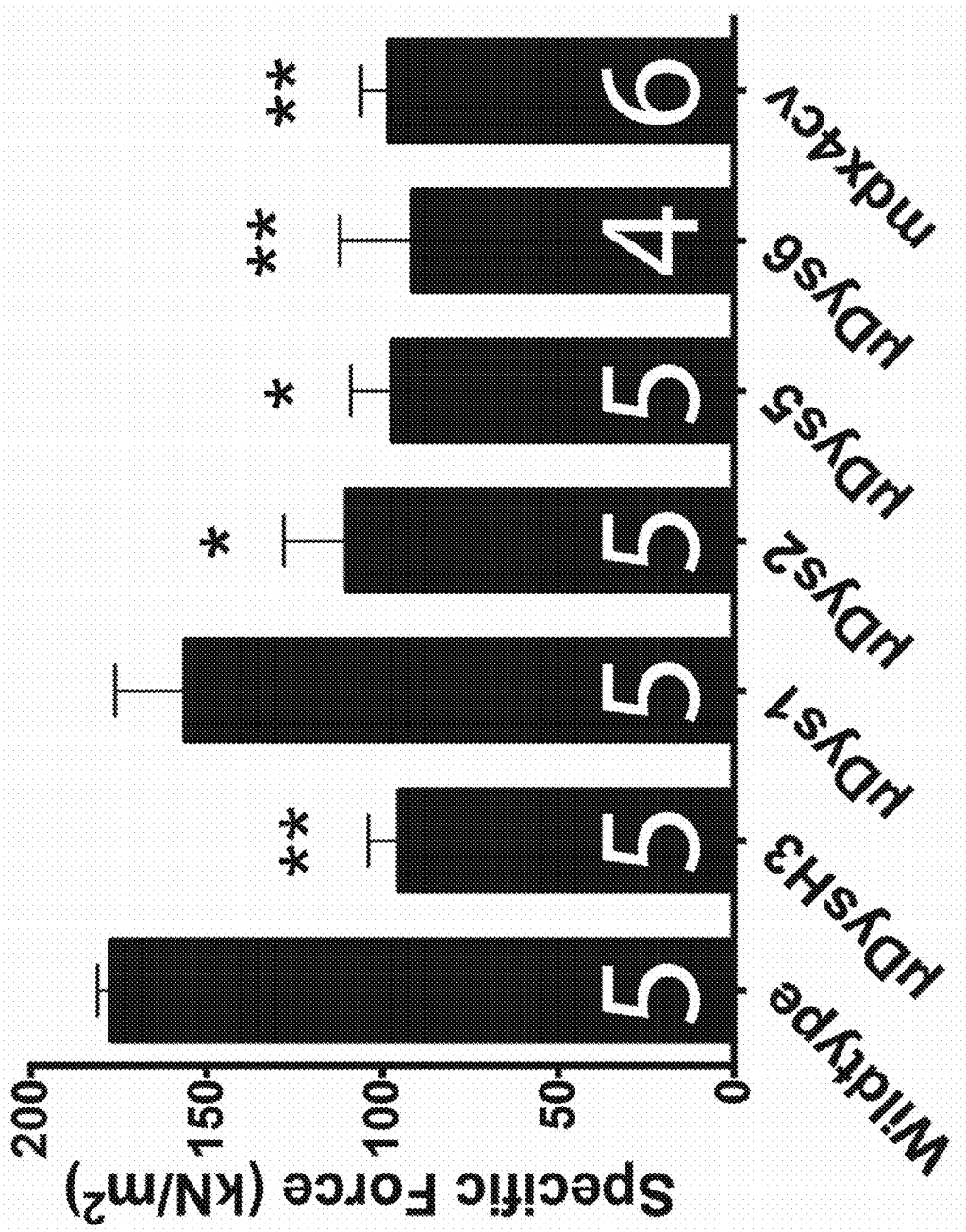

The absence of a functional dystrophin can impair assembly of the DGC. This can result in a loss of mechanical force transmission as well as increased susceptibility to contraction-induced injury (see Emery, A. E. H. and Muntoni, F., Duchenne Muscular Dystrophy, Third Edition (Oxford University Press, 2003) and Ozawa, E. in Myology (ed. Franzini-Armstrong C Engel A) 455-470 (McGraw-Hill, 2004)). Expression of some rAAV-μDys vectors has demonstrated an ability to increase specific force generation and resistance to contraction-induced injury in dystrophic animal models (see Seto, J. T., et al., Current Gene Therapy 12, 139-151 (2012)). It was assessed which novel μDys constructs could improve these metrics at three months post-injection (see FIGS. 3C and 3D).

Gastrocnemius muscles and diaphragm muscle strips were prepared for in situ and in vitro measurement of mechanical properties, respectively. The specific force generation in the gastrocnemius muscle increased in all treated groups compared to untreated dystrophic controls (see FIG. 3B). Only μDys1 and μDys2 injected mice displayed increased specific force in diaphragm muscle strips (156 KN/m$^2$ and 110 KN/m$^2$, respectively, compared to 98 KN/m$^2$ in untreated mice) (see FIG. 3D). Additionally, expression of all the novel μDys constructs increased resistance to contraction-induced injury, yet there were no significant differences in comparison to each other. The dystrophic pathology appeared halted by three months post-injection, yet the physiological performance was not significantly improved. Longer time points may be used to further assess the functionality of the μDys constructs.

Figure 4A:
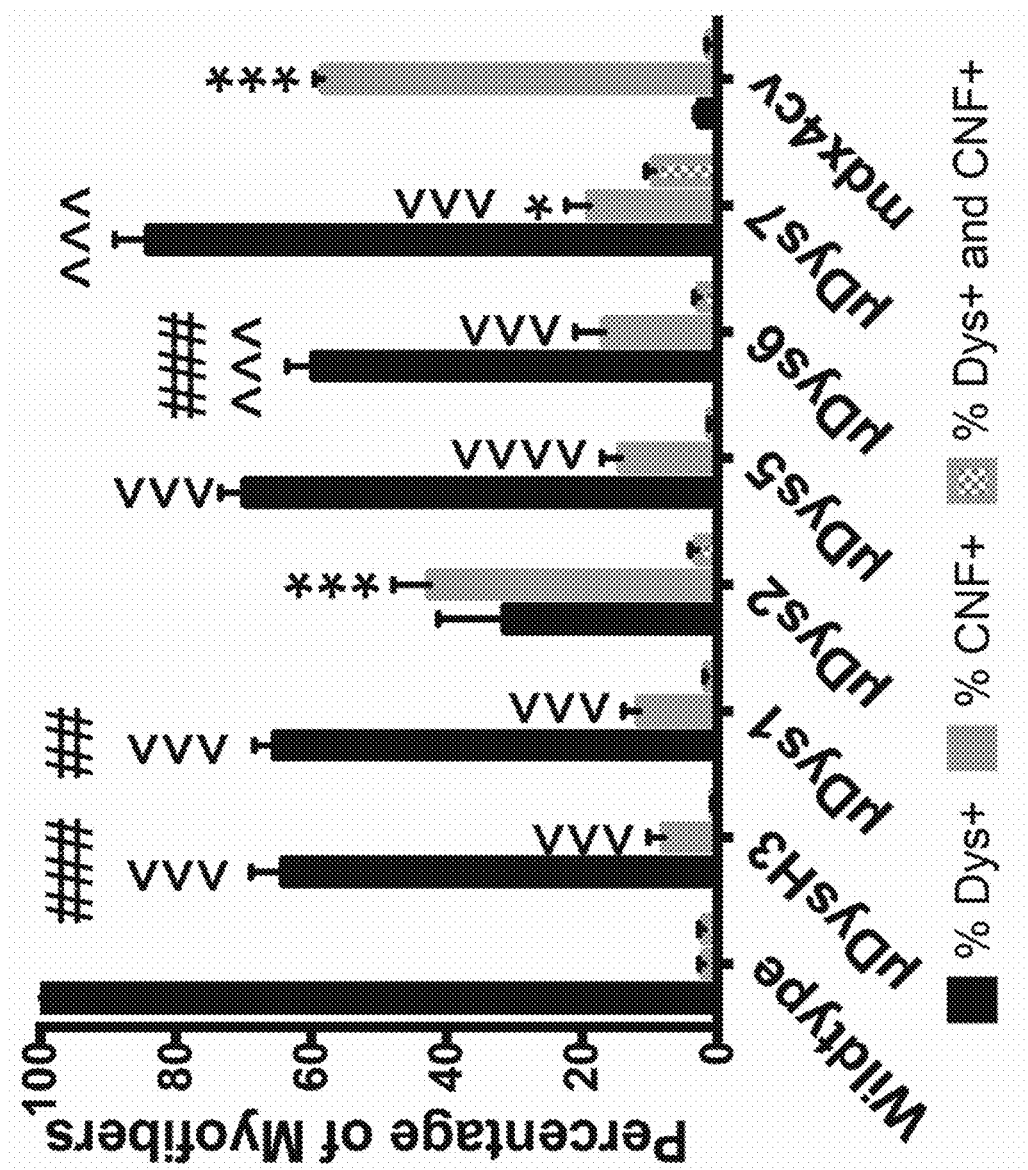
FIGS. 4A-4D are graphs depicting evaluation of systemic treatment at 6 months post-treatment. Gastrocnemius muscles (FIGS. 4A and 4B) and diaphragm muscles (FIGS. 4C and 4D) were evaluated as described in FIGS. 3A-3D. The n value for each cohort is listed in columns of FIG. 4D. *P<0.05, P<0.01, *P<0.001 from wild type. ^P<0.05, ^^P<0.01, ^^^P<0.001 from µDys2-treated mice. #P<0.05, ##P<0.01, ###P<0.001 from µDys7-treated mice.
Figure 4B:
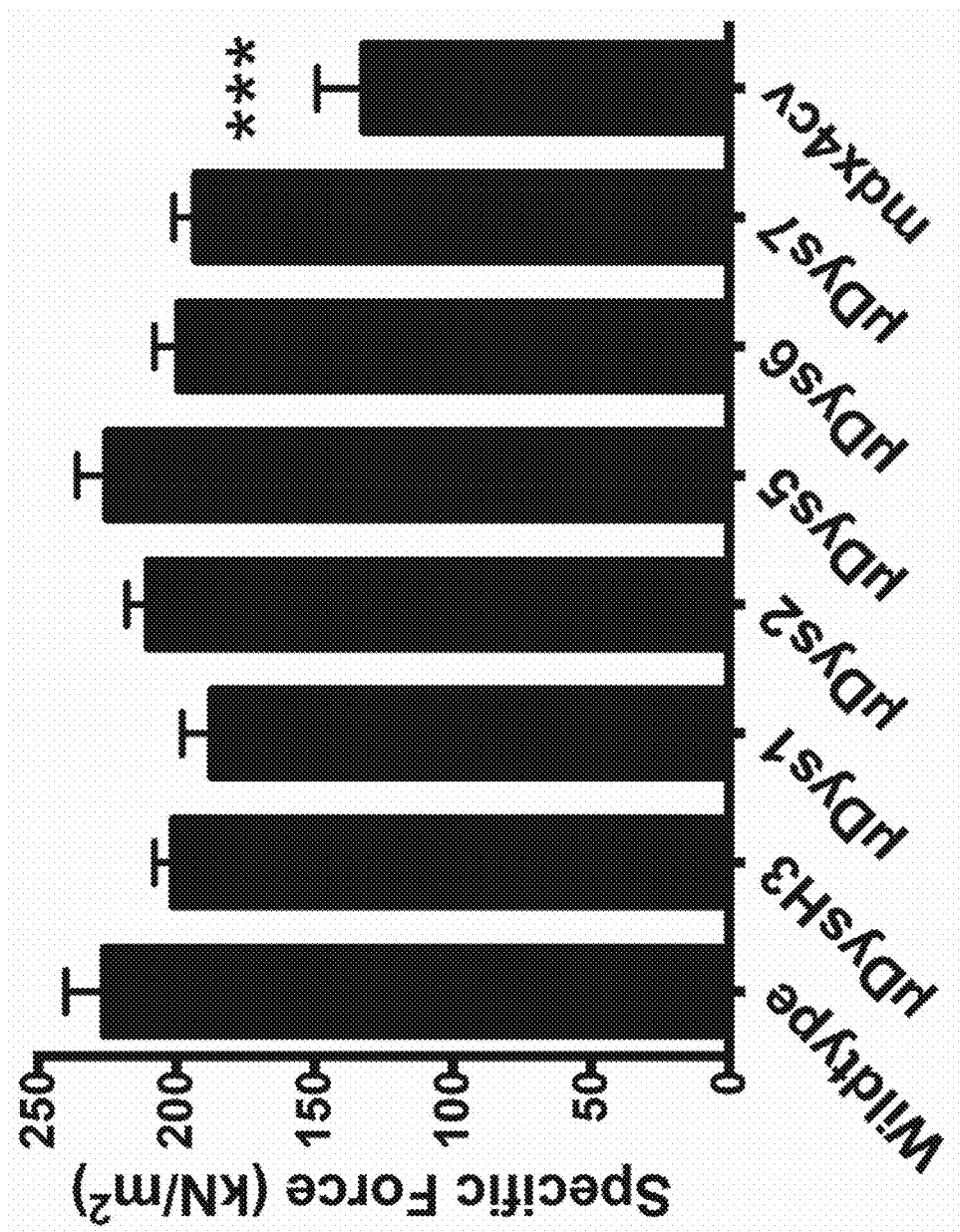
Figure 4C:
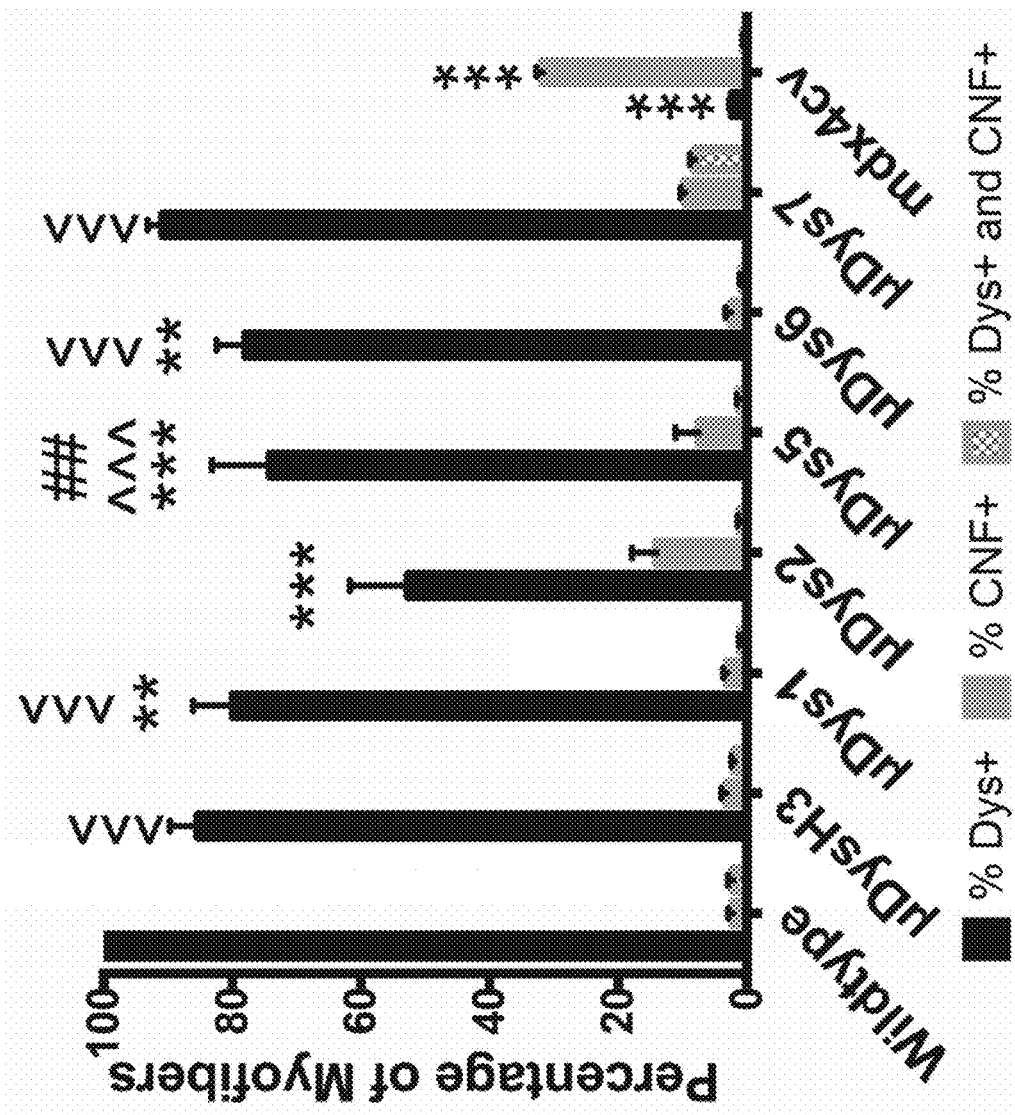

Example 5—Long-Term Expression Exposes Functional Discrepancies of μDys Constructs By six months post-treatment, most treated groups exhibited reduced expression of dystrophin and a concomitant increase in the percentage of myofibers displaying central nucleation, albeit to varying degrees, compared to analysis at three months post-treatment. However, the percentage of myofibers exhibiting both dystrophin expression and central nucleation was not significantly different from wild type controls (see FIGS. 4A and 4C). The μDys1, -5, -6, -7 and -H3 injected mice displayed ≥60% dystrophin positive myofibers in the gastrocnemius and ≥74% in the diaphragm at 6 months. Transduction levels of μDys2 decreased approximately 2-fold in the gastrocnemius over the course of three months (from 63% to 31% positive myofibers), and decreased 20% in the diaphragm, making its performance the worst of the constructs tested (P<0.001; see FIGS. 4A and 4C). The degree of degeneration/regeneration had increased in both muscles for all treated cohorts, with the exception of two tested constructs. Central nucleation for μDys1 remained at 3% in the diaphragm, and μDysH3 decreased from 20% to 8% in the gastrocnemius (see FIGS. 4A and 4C).

Figure 4D:
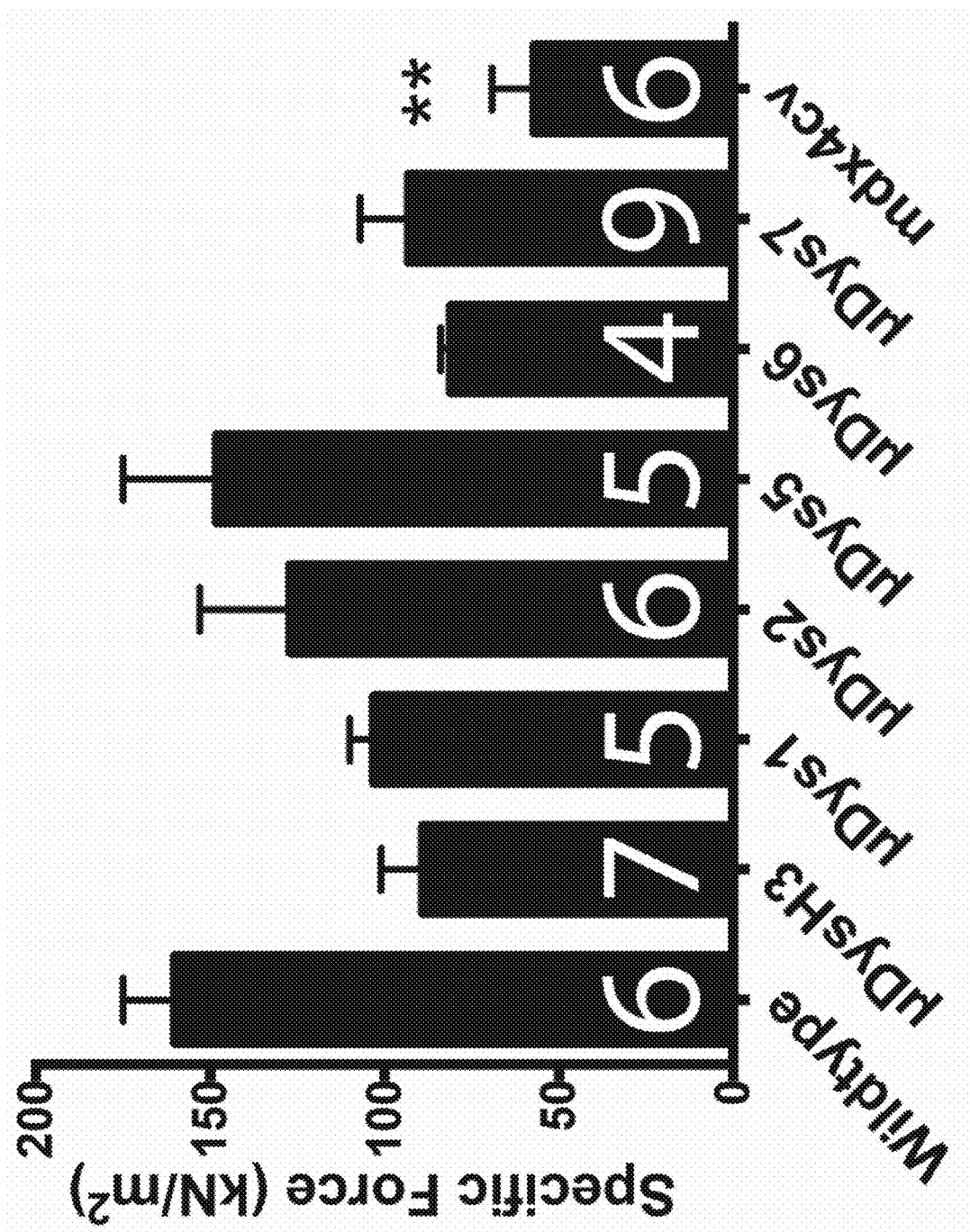
Figure 5A:
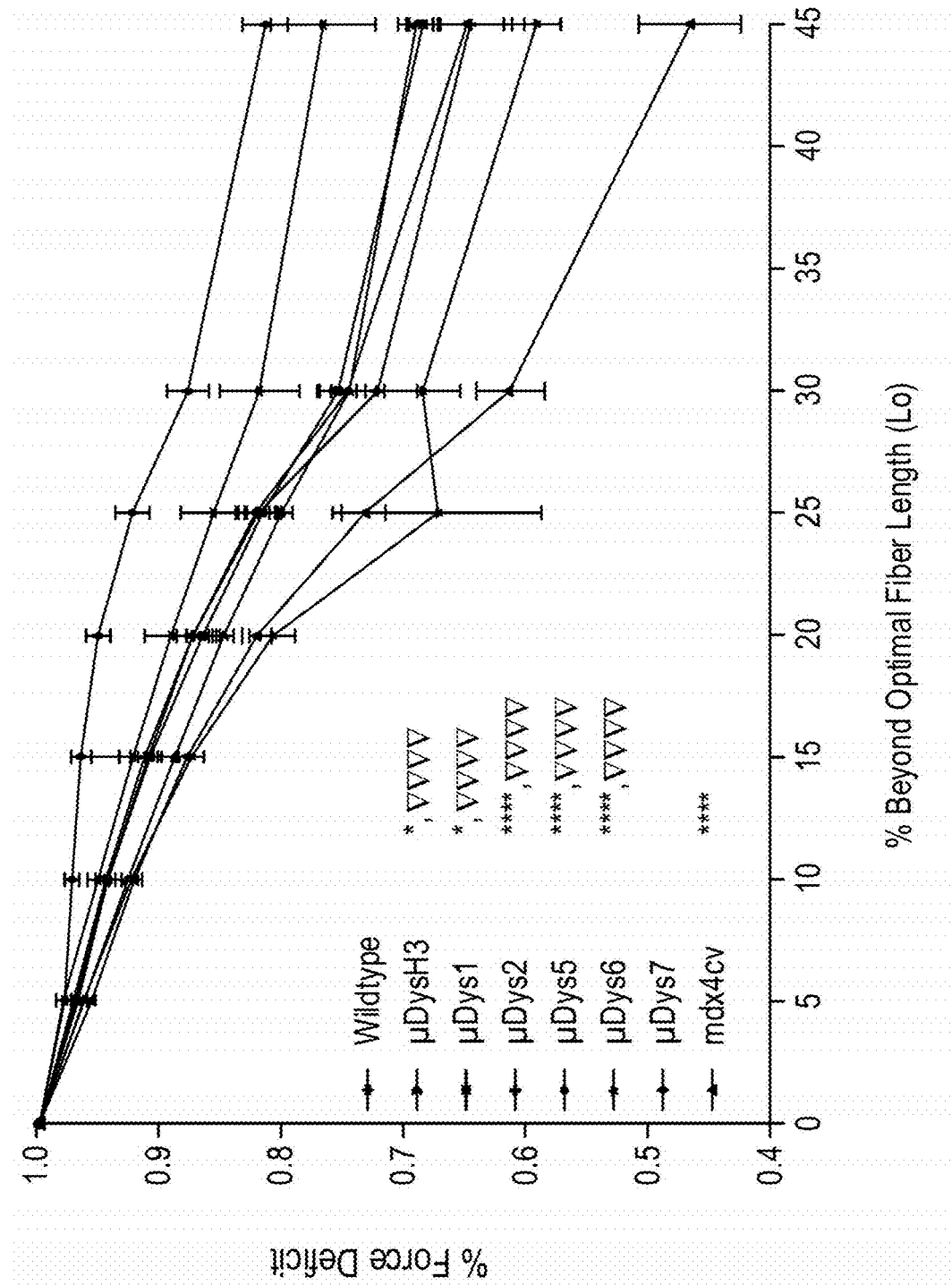
FIGS. 5A and 5B are graphs depicting the extent of sarcolemmal protection from eccentric contraction in skeletal muscles. Systemically treated mice, as described in FIGS. 2 and 4A-4D, were subjected to eccentric contractions of increasing length. Gastrocnemius (FIG. 5A) and diaphragm strips (FIG. 5B) were measured for the maximum isometric force generated prior to an eccentric contraction. During stimulating contractions, muscles were lengthened at a defined distance beyond their optimum fiber lengths. Distances are reported as percentage beyond optimal fiber length ($L_O$). *P<0.05, *P<0.001, **P<0.0001 from wild type at 45% beyond $L_O$. ^^^P<0.001, ^^^^P<0.0001 from µDys2-treated mice at 45% beyond $L_O$. ▽▽▽▽P<0.0001 from µDys7-treated mice at 45% beyond $L_O$.
Figure 5B:
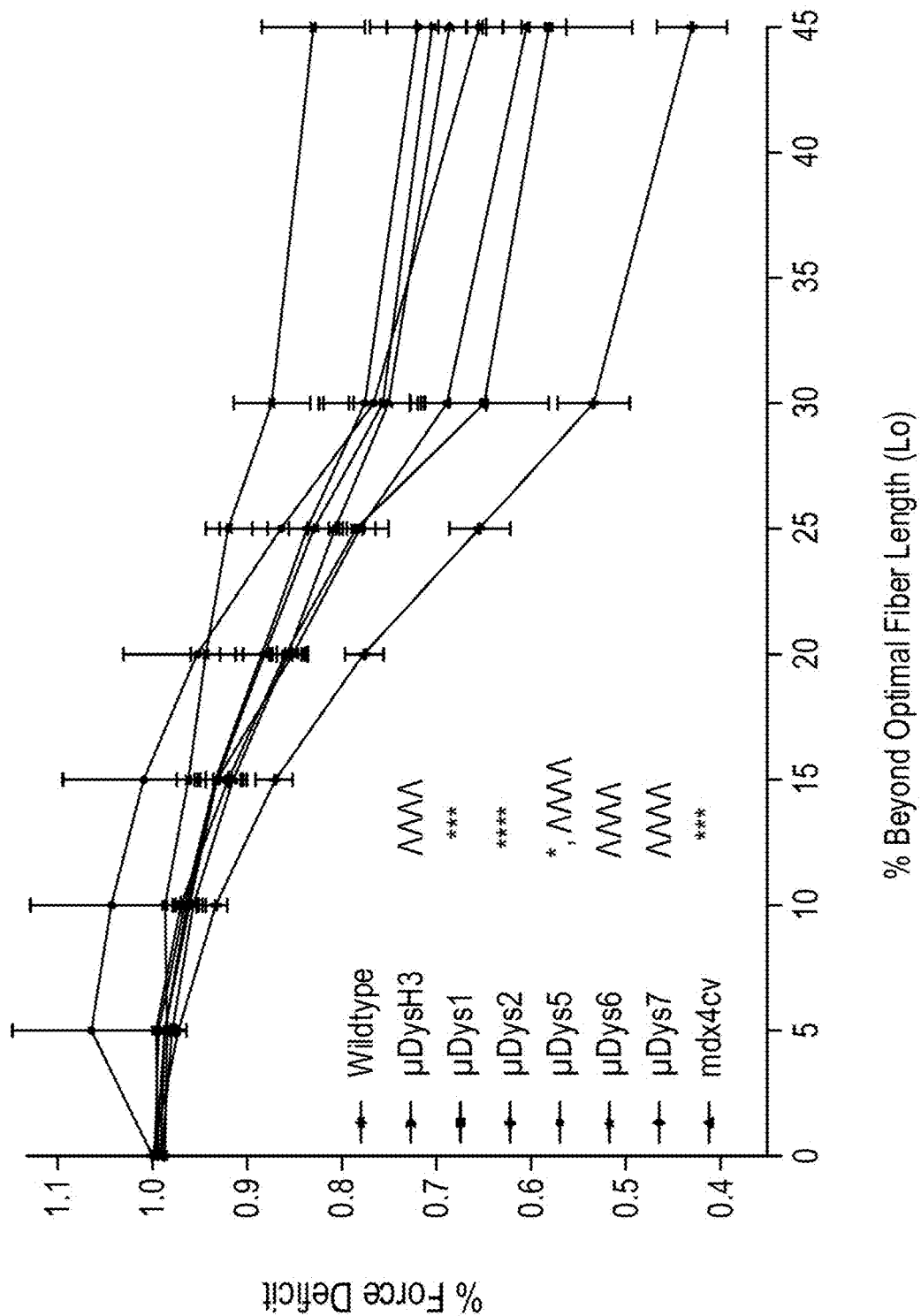
Figure 6:
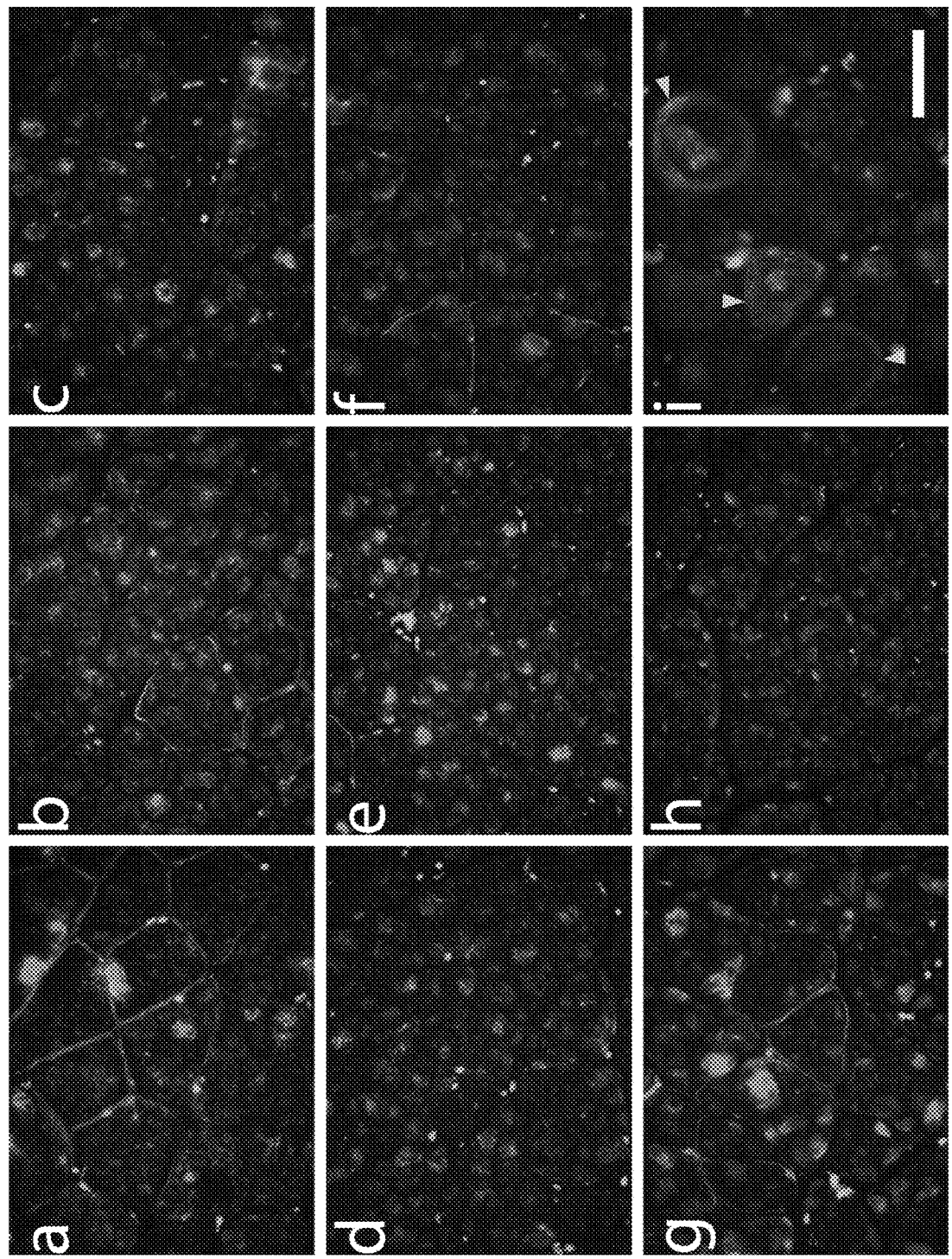
FIG. 6 is a series of micrographs illustrating that systemically tested novel µDys constructs do not induce ringbinden phenotype in skeletal muscle. Dystrophic mdx$^{4cv}$ mice were injected retro-orbitally with $1\times10^{13}$ vg at 14 days of age. Six months post-treatment, cross sections of gastrocnemius muscles were immunostained for dystrophin, DAPI, and α-sarcomeric actin. One representative section is shown from cohorts of wild type (panel "a") and mdx$^{4cv}$ treated with µDysH3 (panel "b"), µDys1 (panel "c"), µDys2 (panel "d"), µDys5 (panel "e"), µDys6 (panel "f"), µDys7 (panel "g"), or untreated mdx$^{4cv}$ mice (panel "h"). Gastrocnemius from transgenic mice expressing ΔR4-R23/ACT (see Harper, S. Q., et al., Nature Medicine 8, 253-261, (2002) on mdx$^{4cv}$ background (panel "i") was also immunostained as a positive control. Arrowheads mark examples of ringbinden formation around myofibers. Scale bar, 50 µm.

Despite the morphological trend observed with the six month post-treatment data, the specific force generation was still higher than in muscles from untreated controls. Injection of one construct, μDys5, led to force generation levels close to those in wild type mice in both the gastrocnemius (225 versus 226 kN/m$^2$; see FIG. 4B) and the diaphragm (148 versus 160 KN/m$^2$; see FIG. 4D). Based on previous studies with mini-dystrophins containing six to eight SRs, it was predicted that the μDys constructs containing six SRs would generate the most specific force as well as provide the greatest protection from contraction-induced injury (see Harper, S. Q., et al., Nature Medicine 8, 253-261, (2002)). However, specific force generation in the gastrocnemius muscles of μDys6 and μDys7 treated mice was significantly higher than untreated controls (P<0.01 and P<0.0001, respectively), but were not the highest (see FIGS. 4B and 4D). Instead, μDys5 injected mice displayed the highest levels of specific force generation. The larger constructs were also not necessarily the best at protecting from contraction-induced injury. For example, μDys6 injected mice had the largest force deficit while μDys7 provided the highest protection from contraction-induced injury in the gastrocnemius (see FIG. 5A). However, resistance to contraction-induced injury in diaphragm muscle strips was the highest in mice expressing μDys6 and μDys7 as well as μDys5 and μDysH3 (see FIG. 5B). The contrasting results among μDys6 and μDys7 between muscle groups and the significant difference in force deficits within the gastrocnemius (P<0.0001) suggest that the performance of a particular μDys construct may be influenced by the regulatory expression cassette and the muscle assessed (see Harper, S. Q., et al., Nature medicine 8, 253-261, (2002) and Salva, M. Z., et al., Molecular Therapy: The Journal of the American Society of Gene Therapy 15, 320-329, (2007)). This point was also exemplified with µDys2 treatment, where the susceptibility to contraction-induced injury was reduced in the gastrocnemius but unexpectedly exacerbated in the diaphragm, relative to untreated controls (see FIGS. 5A and 5B).

Example 6—Gene Delivery Via rAAV6+Cardiac-Specific Promoter

Vectors for WT and L48Q cTnC (rAAV6-WT cTnC and rAAV6-L48Q cTnC, respectively) were produced. Plasmids can be produced with rAAV genomes containing a cardiac specific promoter (cTnT455) and a C-terminal c-Myc tag. cTnC variant transgene expression cassettes (with an mCherry fluorescent reporter) can be co-transfected into HEK293 cells with a packaging/helper plasmid pDGM6 by $CaPO_4$ precipitation methodology. Vectors can be collected from culture, freeze-thawed, and the supernatant can be collected. Affinity purification can use a HITRAP™ heparin column (GE HEALTHCARE LIFE SCIENCES™, Piscataway, NJ). The virus can be concentrated on a sucrose gradient (40%), spun at 27,000 rpm (18 hours, 4° C.), and resolubilized in Hanks' balanced solution. Vector genomes can be determined relative to plasmid standards using a SV40 polyadenylation region oligonucleotide $^{32}P$ end-labeled probe with Southern blot hybridization and confirmed by qPCR.

Figure 8:
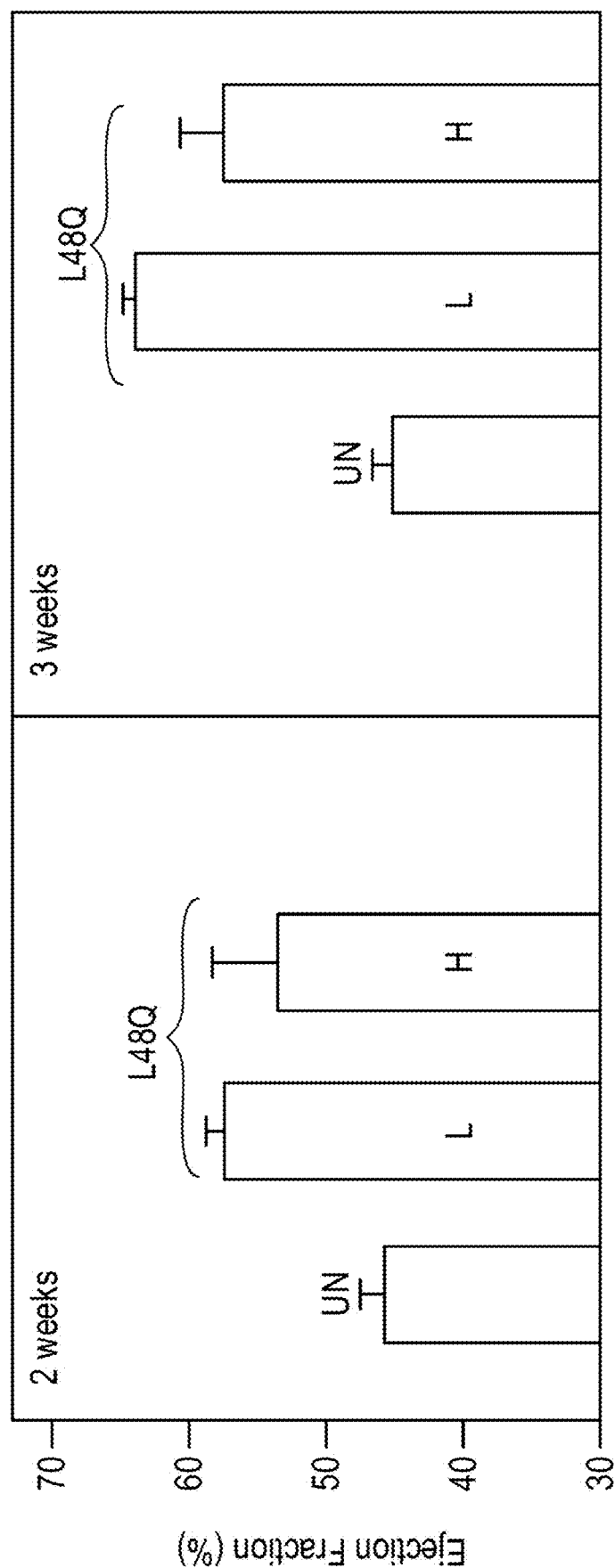
FIG. 8 is two graphs depicting left ventricle (LV) ejection fraction at 2 weeks (left) and 3 weeks (right) for untreated (UN; n=5) vs. low (L; n=3) or high (H; n=3) dose of AAV6-L48Q.
Figure 9:
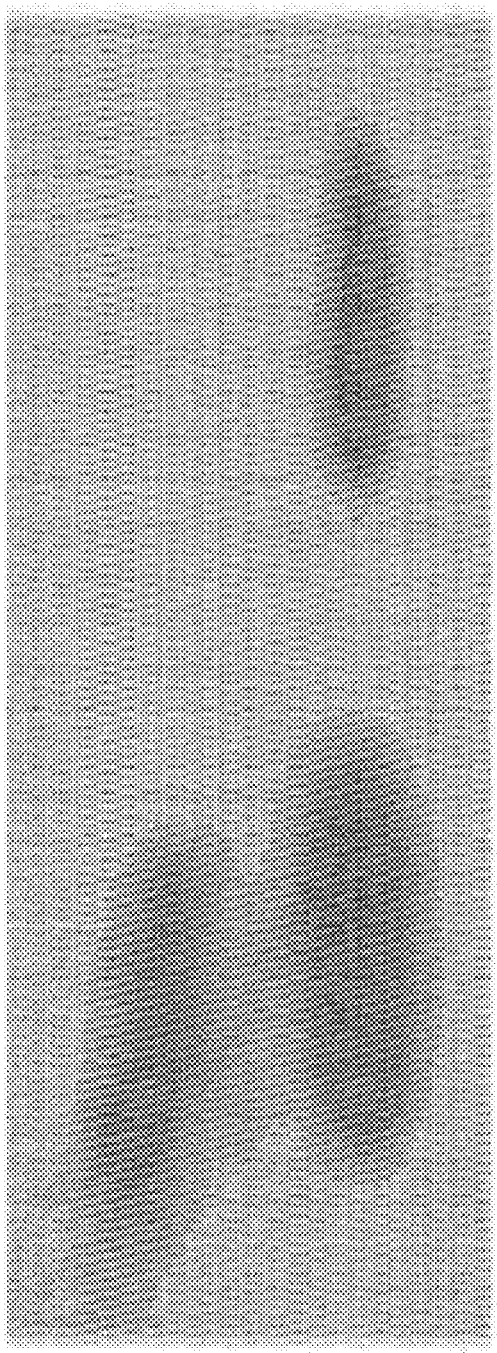
FIG. 9 is an anti-cTnC Western blot for AAV6-L48Q cTnC injected mouse cardiac tissue (left) and uninjected control (right), as indicated

FIG. 8 depicts the first use of the rAAV6-L48Q cTnC systemically injected (intraocular) into 3 mice each at low (L; $0.6 \times 10^{12}$) and high (H; $1.2 \times 10^{12}$) viral particle dose. Echocardiography indicated about a 20% increase in left ventricular (LV) ejection fraction compared with uninjected (UN) controls two weeks after injection, and a 30-40% increase at 3 weeks. Systemic injections with control adenoviral vectors have not altered LV function. Myofibrils from one rAAV6-L48Q cTnC-myc transfected mouse (and uninjected control) were separated by SDS-PAGE and Western blots were probed with anti-cTnC. The presence of myc-tag caused slower migration of cTnC (see FIG. 9), and the ratio of cTnC-myc to native cTnC was densitometrically determined to be about 40% (similar to that seen with adenovirus and transgenic animals, see below).

Example 7—Acute and Chronic Effects of cTnC Variants on Cardiac Function

Acute and chronic effects of cTnC variants on cardiac function can be assessed using rAAV6-cTnC vectors and transgenic mice. To determine the response to acute changes in myofilament function, normal adult mice can be transfected via tail vein or intraocular orbit injection of rAAV6-cTnC variants (e.g., WT, L48Q, L57Q, or 161Q) with a cardiac specific promoter (cTnT455). Parallel experiments can be performed with the L48Q cTnC and 161Q cTnC transgenic mice by repressing the MHC promoter until adulthood. Additional studies can be conducted with mice without repression of the promoter to determine the effects of these cTnC variants on normal cardiac development and function. Echocardiographic assessments at 1, 2, 3, and 6 months of age can be conducted to determine onset and progression of any changes in function. Some animals may be stressed via β-adrenergic stimulation with isoproterenol. Following echocardiography, some animals may undergo hemodynamic measurements using MILLAR™ catheter protocols, others may be euthanized and hearts dissected for working heart protocols or for intact or skinned trabeculae preparations, cultured cardiomyocytes, or myofibril preparations.

Example 8—Tissue-Specific Targeting with rAAV6 Constructs

Figure 12A:
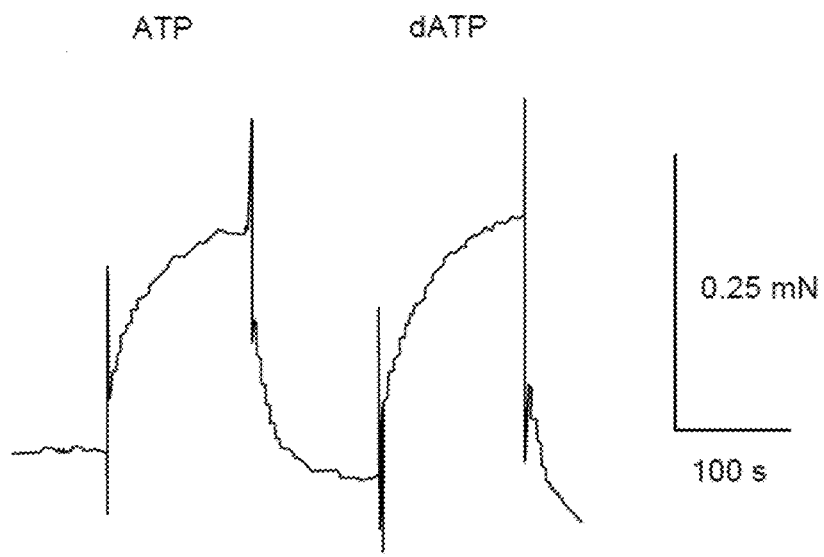
FIG. 12A depicts mouse aortic smooth muscle contraction traces with ATP and dATP.
Figure 12B:
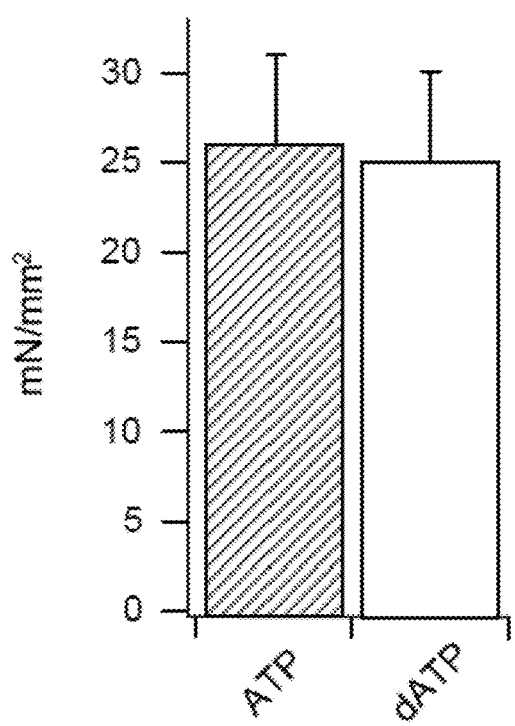
FIG. 12B is a graph depicting a summary of the data in FIG. 12A.

Tissue specificity was assessed using alkaline phosphatase driven by various gene promoters in rAAV6 constructs. Table 2 (see below) compares two cardiac specific promoters (creatine kinase 7 (CK7) and cardiac troponin T (cTnT455)) to the non-specific cytomegalovirus (CMV) promoter), with values normalized to CK7 in the TA. cTnT455 can lead to high expression in the heart but little to no expression in other tissue. This specificity may reduce potential for effects of R1R2 over-expression in non-cardiac tissues.

dATP has no significant effect on mouse aortic smooth muscle force development. To study potential systemic effects of elevated dATP it was determined if dATP affects mouse aortic smooth muscle contraction. FIG. 12A shows that back to back contractions in skinned muscle strips did not differ for dATP vs. ATP as the contractile substrate, and the data for multiple experiments is summarized in FIG. 12B. Additionally, control measurements demonstrated that dATP did not change the level of myosin light chain phosphorylation, which controls smooth muscle myosin binding to actin.

Example 9—Recombinant AAV6-R1R2 for Cardiac-Specific Targeting rAAV6 vectors were used to acutely increase cardiac levels of R1R2 (and [dATP]). Plasmids can be produced with recombinant rAAV genomes containing a cardiac specific promoter (cTnT455). R1R2 transgene expression cassettes can be co-transfected into HEK293 cells with a packaging/helper plasmid pDGM6 by $CaPO_4$ precipitation methodology. Vectors can be collected from culture, freeze-thawed, and the supernatant can be collected. Affinity purification can use a HITRAP™ heparin column (GE HEALTHCARE LIFE SCIENCES™, Piscataway, NJ). The vector can be concentrated on a sucrose gradient (40%), spun at 27,000 rpm (18 hours, 4° C.), and resolubilized in Hanks' balanced solution. Vector genomes can be determined relative to plasmid standards using a SV40 polyadenylation region oligonucleotide $^{32}P$ end-labeled probe with Southern blot hybridization and confirmed by qPCR.

TABLE 2

Comparison of CK7, CMV, and cTnT455 promoters

| | CK7 | CMV | cTnT455 |
|---|---|---|---|
| Tibialis Anterior | 1 | 3.1 | 0 |
| Heart | 1.9 | 5.1 | 1.6 |
| Lung | 0.02 | 0.09 | 0.01 |
| Liver | 0.02 | 0.09 | 0.004 |
| Aorta | 0.01 | 0.13 | 0.005 |

Figure 14:
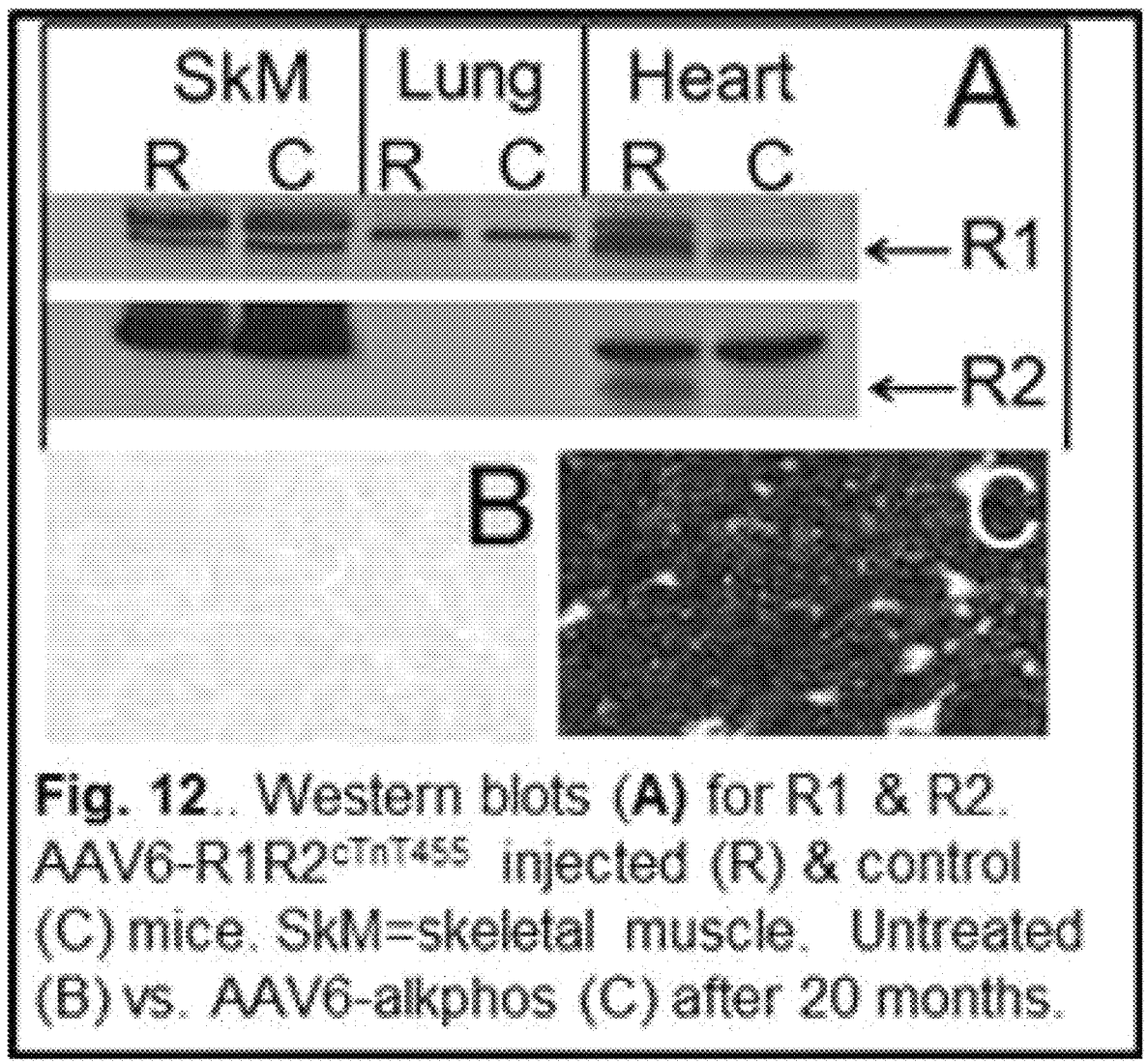
FIG. 14 shows preliminary Western blot evidence for the expression levels of R1 and R2 subunits in the skeletal muscle, lung, and heart of rAAV6-R1R2$^{cTnT455}$ injected ($4.5\times10^{13}$) mice and control mice (panel "A").

Selection of the cardiac targeting construct was assessed using alkaline phosphatase driven by various gene promoters in rAAV6 constructs. Table 2 compares two striated muscle specific promoters (creatine kinase 7 (CK7) and cardiac troponin T (cTnT455)) to the nonspecific cytomegalovirus (CMV) promoter, with values normalized to CK7 in the TA. cTnT455 can lead to high expression in the heart, but little to no expression in other tissue, thus reducing the potential for effects of R1R2 over-expression in non-cardiac tissues. FIG. 14A shows Western blot evidence for this, where heart tissue from a rAAV6-RIR2cTnT455 injected (4.5 e13) mouse expressed high R1 & R2 subunits compared to control mouse heart. Note that upper bands are nonspecific staining, with arrows pointing to R1 and R2 protein (identified by molecular weight markers). R1 & R2 expression in lung was extremely low in comparison with heart and was not changed in skeletal muscle. This is demonstrated in FIG. 14 for heart tissue from non-injected (panel "B") vs. rAAV6-alkaline phosphatase (panel "C") injected mice, suggesting rAAV6-RIR2cTnT455 may provide stable, long-term R1R2 over-expression. Stable rAAV6 transgene expression has also been shown to persist for 12 or more weeks in rat and at least 6 or more months in dogs.

Figure 15:
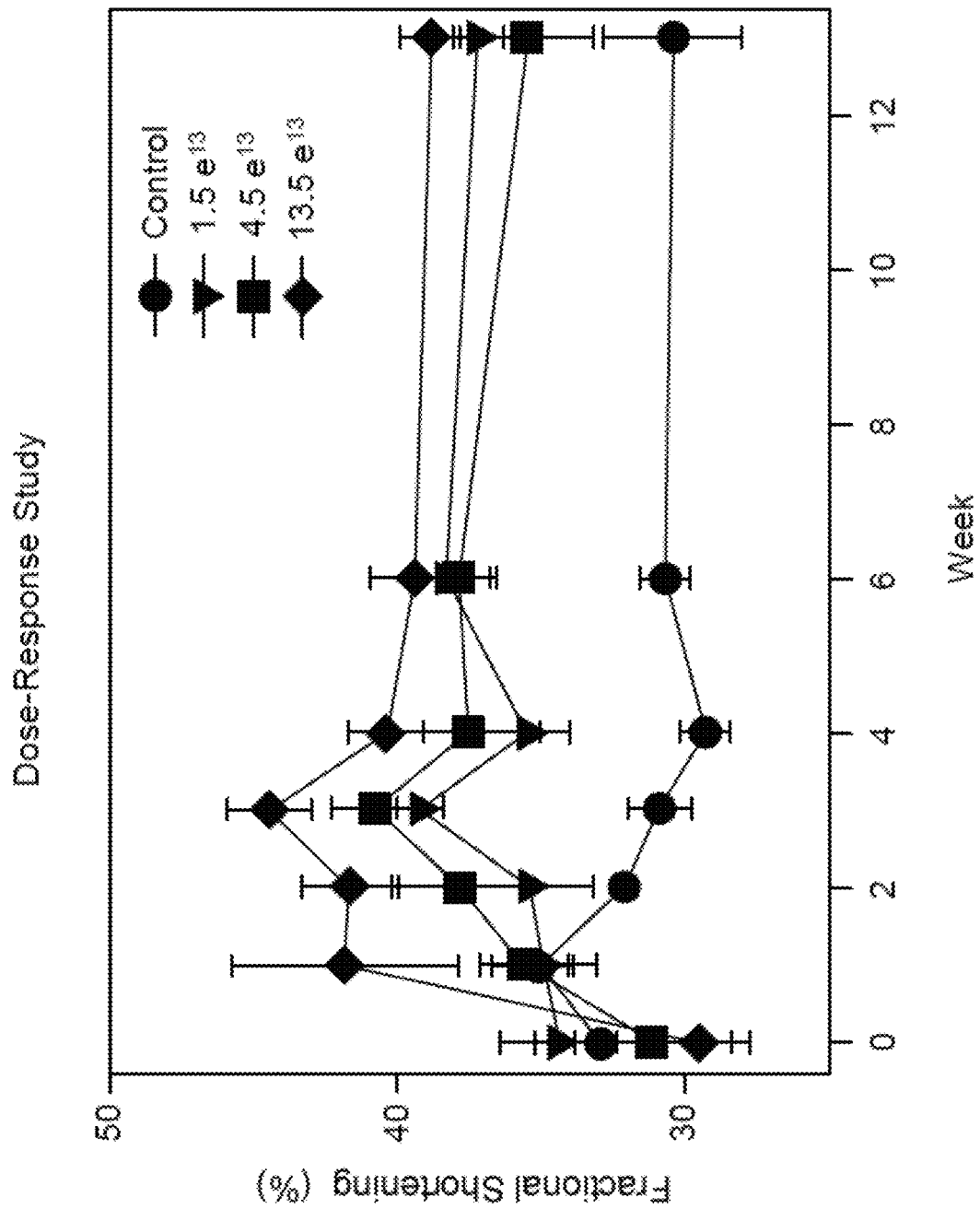
FIG. 15 is a graph showing the effect of $1.5\times10^{13}$, $4.5\times10^{13}$, and $1.35\times10^{14}$ rAAV6-RIR2$^{cTnT455}$ vector genomes or saline (control) injected systemically over an approximate 10-fold range into 3 month old mice (n=6 per group) on LV function.

Studies may determine the relationship between rAAV6-R1R2cTnT455 injection dose, time course, and stability of increased LV pump function, cardiac tissue R1R2 levels, and [dATP]. FIG. 15 shows the effect of 3 vector doses, i.e., $1.5 \times 10^{13}$, $4.5 \times 10^{13}$, and $1.35 \times 10^{14}$ rAAV6-R1R2cTnT455 vector genomes or saline (control) injected into 3 month old mice (n=6 per group) on LV function. LV fractional shortening (FS) was significantly increased at the high dose after one week and at all doses after two weeks, with equivalent effects by 6 weeks. The magnitude increase in FS is 25%-50%, indicating the effect that may be achievable with a relatively low vector dose.

Example 10—Transgenic R1R2 Over-Expression Mice (TG-R1R2)

Figure 11:
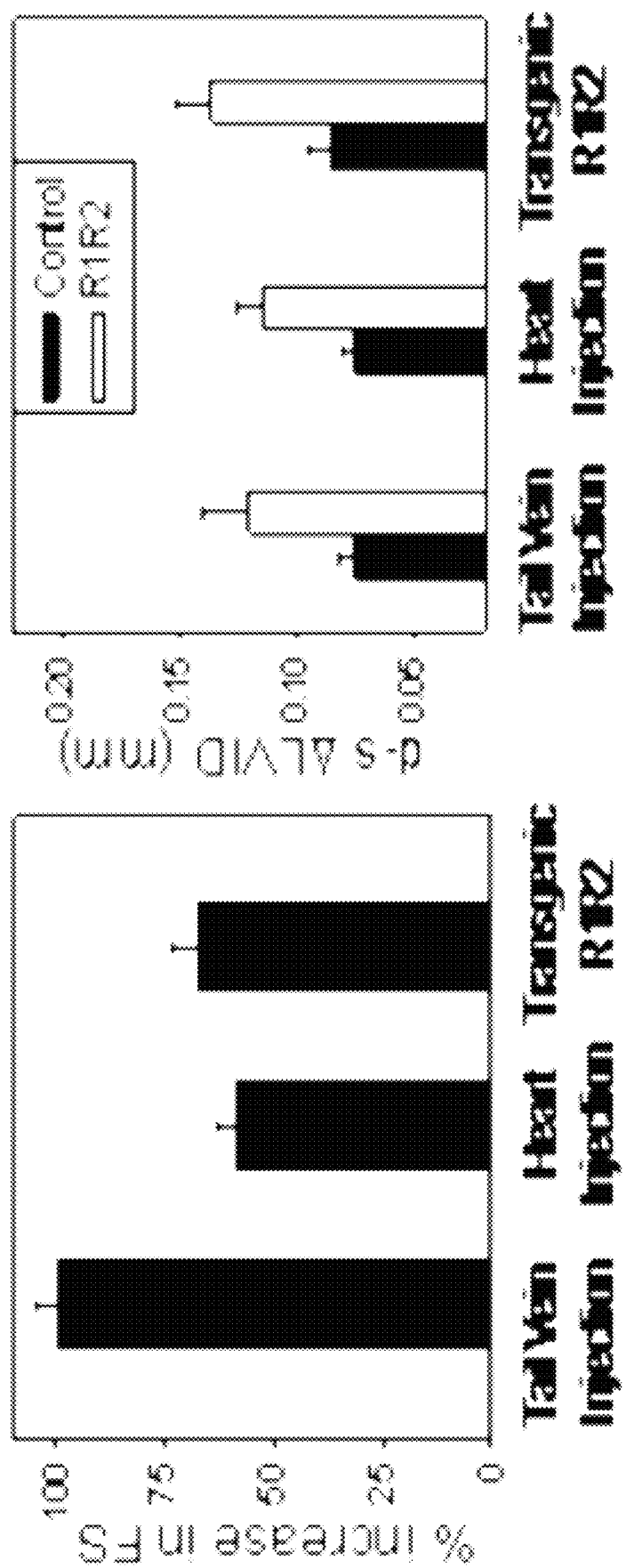
FIG. 11 is two graphs. The graph at the left depicts the percentage fractional shortening (FS) increase in R1R2 over-expressing mice vs. control littermates. The graph at the right depicts the change in left ventricular inner diameter (LVID) in R1R2 over-expressing mice vs. control littermates. d-diastole, s-systole.
Figure 13A:
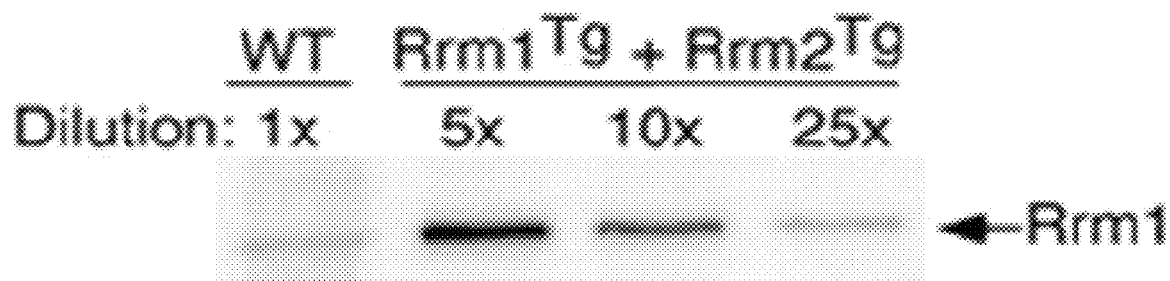
FIG. 13A depicts Western blots for R1 and R2.
Figure 13A:
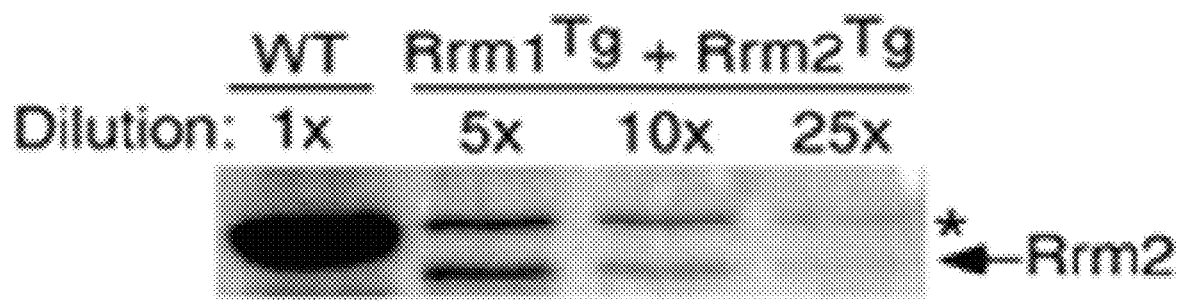
Figure 13B:
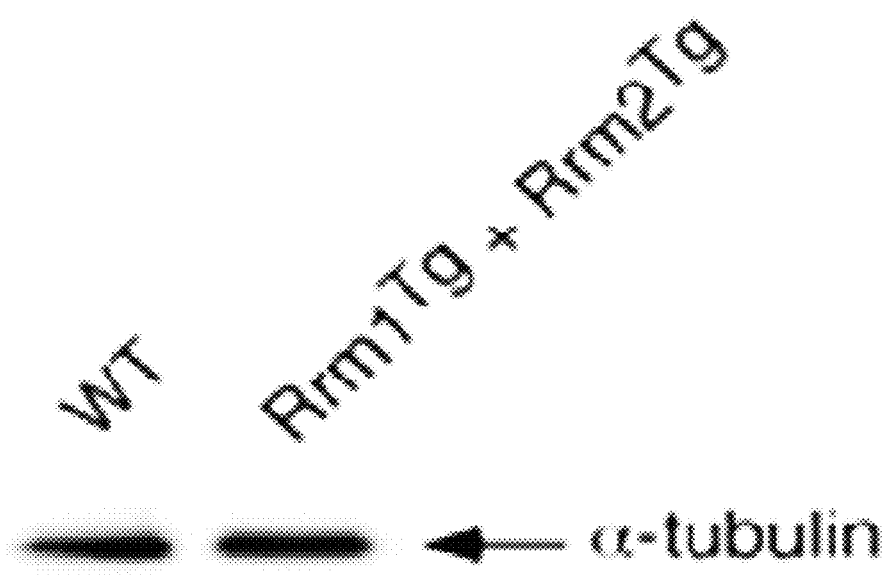
FIG. 13B depicts α-tubulin as a loading control for the Western blots of FIG. 13A.

Bi-transgenic mice that over-express both subunits (Rrm1 & Rrm2) of RR can be utilized. FIG. 13 depicts over-expression of both subunits in cardiac muscle, with densitometric calculation values for these TG-R1R2 mice that are 33.7±7.6 (Rrm1) and 23.7±3.4 (Rrm2) fold greater than corresponding values for wild type (WT) mice. Note that for Rrm2 the upper band (*) is non-specific. The endogenous Rrm2 protein is not detectable in WT tissue, but in TG-R1R2 mice it appears as the band below the background band. While dATP levels for cardiac tissue have not yet been assessed, [dATP] is increased 10-fold in skeletal muscle, which had corresponding 3.3±2.1 (Rrm1) and 35.7±11.1 (Rrm2) fold increases in the enzyme subunits. This magnitude of increase in dATP is similar to what has been determined for cardiomyocytes transfected with adenovirus-R1R2 in culture (see FIG. 10). Preliminary echocardiography of these TG-R1R2 mice at 6-8 months of age (measured on 3 successive weeks) revealed an average >50% increase in fractional shortening (FS) and a 15% reduction in diastolic LV inner diameter (LVIDd). As shown in FIG. 11, these differences (from WT controls) are similar in magnitude to values for the preliminary adenovirus-R1R2 injection experiments.

Example 11—Acute Effects of Elevated Cellular R1R2 and [dATP] on Cardiac Function Acute R1R2 over-expression (via rAAV6-R1R2 vectors) may increase [dATP] in mouse hearts, resulting in increased systolic and diastolic function. This may be reflected in: 1) increased cardiomyocyte and myofibril contraction with faster relaxation (due in part to increased crossbridge cycling kinetics); 2) an increase in basal cardiac metabolism without compromising energetic reserves; and 3) no change or a decrease in action potential duration (due to enhanced $Ca^{2+}$ sequestration).

Normal adult FVB/N mice can be transfected via tail vein or intraocular orbit injection with rAAV6-R1R2 vectors with the cardiac specific promoter cTnT455 (as described above), with sham injections and with rAAV6 containing only cTnT455 as controls. Following injection, echocardiography can be performed weekly (out to 6 weeks) to determine the optimal (maximal effect) time point for further assessments. Initial studies may characterize cardiac function in vivo with echocardiography, followed by in situ hemodynamic measures, or ex vivo using Langendorff perfused hearts for energetic studies and a working heart apparatus to assess pump performance. At selected time-points, other mice can be euthanized and hearts dissected for intact or skinned trabeculae preparations, isolated cardiomyocytes, myofibril preparations, protein analysis, and (immuno) histology. These measurements may provide molecular mechanisms for alterations in cardiac function with acute R1R2 over-expression.

Example 12—Myofilament and SR Protein Profiling

Changes in contractile function, $Ca^{2+}$ transients, SR spark activity, and/or $Ca^{2+}$ load under all conditions may be correlated with isoform, abundance, and phosphorylation of myofilament proteins (cTn1, cTnT, MLC-2, cMyBP-C, and Tm), SR proteins (PLB, RyR), and sarcolemmal proteins (NCX, PMCA, and L-type $Ca^{2+}$ channel). Changes in mRNA and protein expression may be determined using RT-PCR and Western blot analysis. SR protein fractions can be prepared. If electrophysiological measurements indicate changes, ion channels can be assessed with specific antibodies. Analysis of R1R2 expression can be made via Western blots (see FIG. 10) or immunohistochemistry, and correlated with experimental endpoints. Specificity of the cTnT455 promoter can be assessed by determining R1R2 expression in non-cardiac tissues such as skeletal muscle and lung. Phosphorylation can be profiled using PRO-Q® Diamond phosphoprotein gel stain (with SYPRO® Ruby Protein Gel Stain) and Western blot analysis. For site specific serine and threonine residue phosphorylation, mass spectrometry can be performed.

Figure 16:
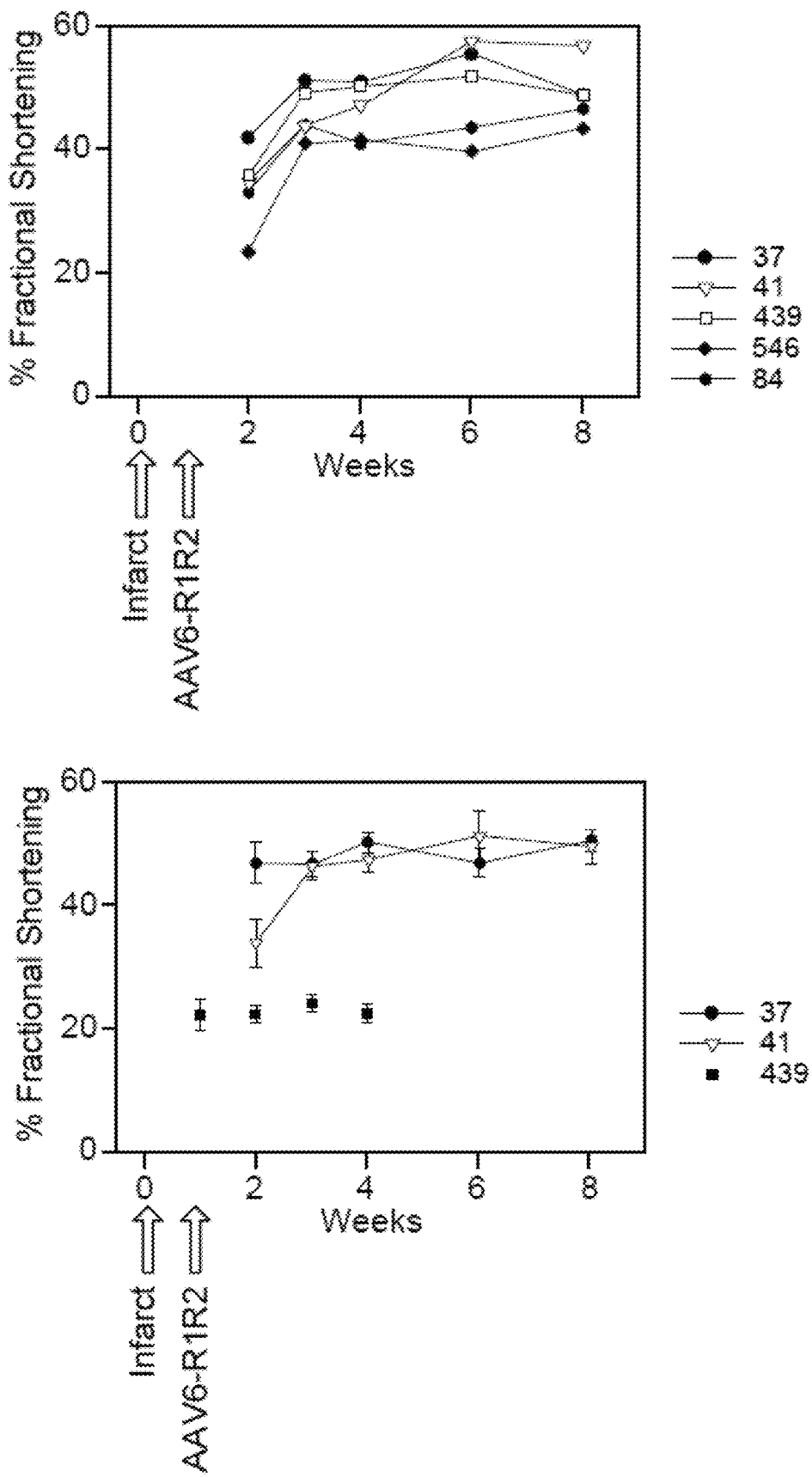
FIG. 16 is two graphs showing the change in fractional shortening in rats given direct cardiac injections of rAAV6-R1R2 on the fifth day post-infarct as measured by echocardiography in comparison with untreated infarct rats and untreated sham-operated rats.
Figure 17:
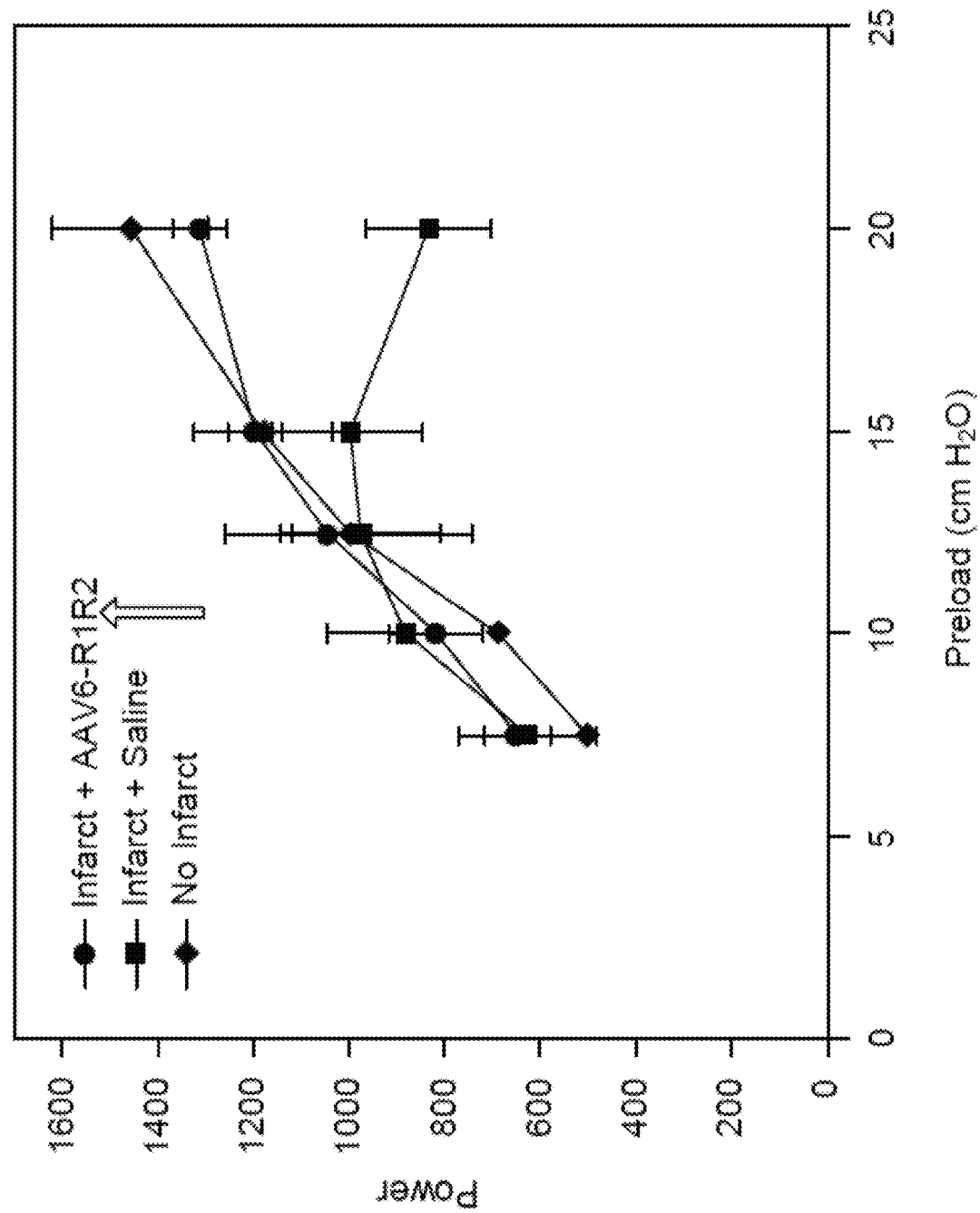
FIG. 17 is a graph showing the in vitro Neely working heart measurements of the rat hearts assessed in FIG. 16. Power on the y-axis is given in units of g·cm/min. A loss of pre-load responsiveness of hearts (heart failure) that have been infarcted (no treatment) and a recovery of pre-load responsiveness of the infarcted hearts receiving the vectors to the level of control, uninfarcted hearts were observed, thereby demonstrating a restoration of cardiac function.

R1R2 over-expression and increased [dATP] may improve cardiac performance of infarcted hearts at the selected time point for analysis. Response to high $Ca^{2+}$ challenge, β-adrenergic stimulation, and increasing pre-loads may be improved. In vitro Neely working heart measurements of the hearts assessed in FIG. 16 showed a loss of pre-load responsiveness of hearts (heart failure) that have been infarcted (no treatment), but showed a recovery of pre-load responsiveness of the infarcted hearts receiving the vectors to the level of control, uninfarcted hearts, thereby demonstrating a restoration of cardiac function. With reference to FIG. 17, where power is given in units of g·cm/min, the effect may have occurred by lessening chronic β-adrenergic stimulation (which can be assessed by monitoring plasma hormones). This may be reflected in the multi-scale analysis as improved: 1) $Ca^{2+}$ transients; 2) myofilament contraction and relaxation magnitude and kinetics; and 3) energetic profile. A difference between treated and untreated hearts in α- and β-adrenergic mediated cardiomyocyte protein phosphorylation may also be seen.

Example 13—AAV9 Vector Carrying CK8-µDys5

Figure 22:
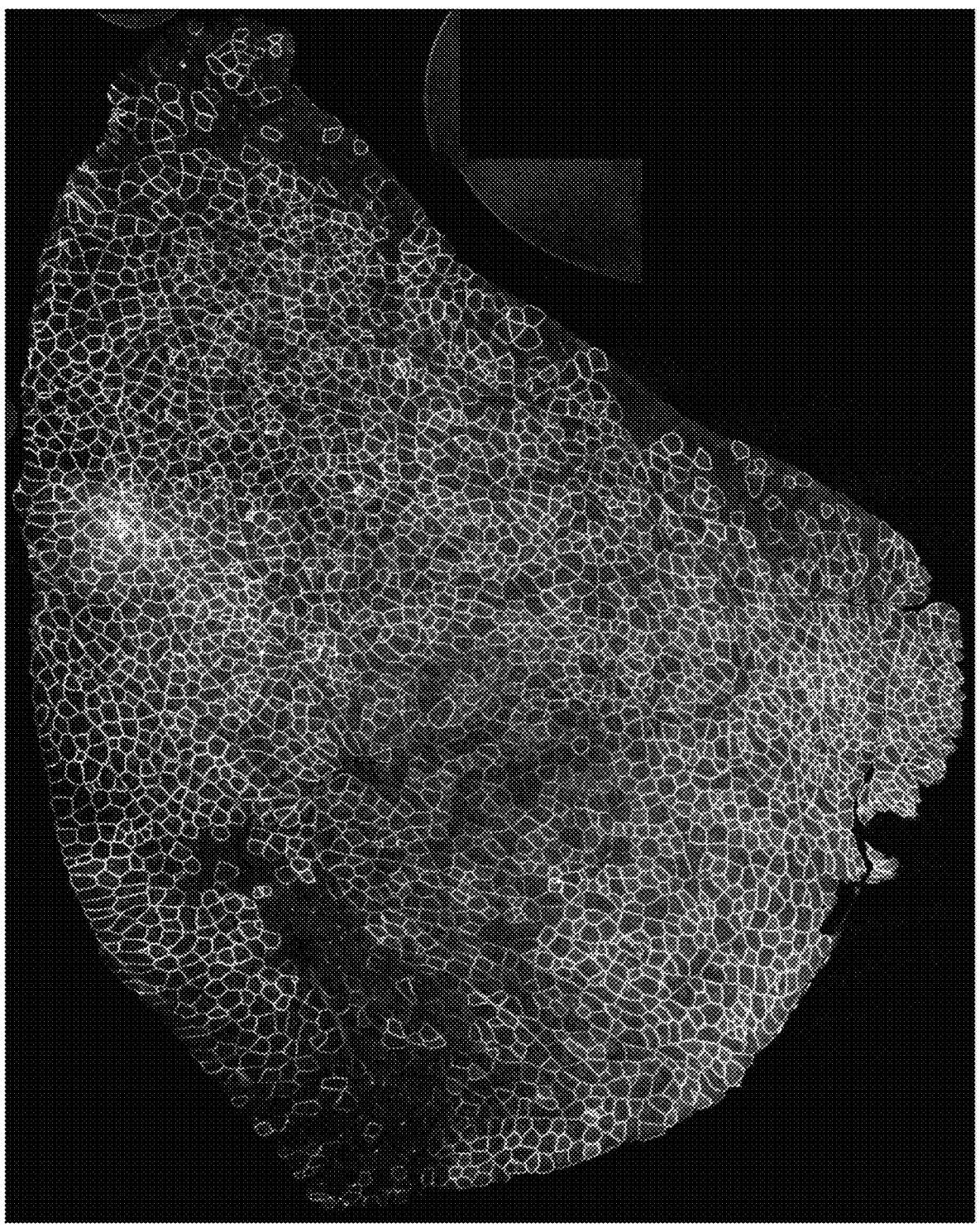
FIG. 22 is an image of an mdx$^{4cv}$ mouse muscle cryosection that was stained for dystrophin expression using an anti-dystrophin antibody.

An 8 week old $mdx^{4cv}$ mouse was injected (intramuscularly) into the TA muscle with $2.5 \times 10^{11}$ vector genomes of an AAV9 vector carrying a CK8-µDys5 expression cassette. Two weeks later, the mouse was sacrificed and muscle cryosections were stained for dystrophin expression using an anti-dystrophin antibody. As shown in FIG. 22, widespread and robust expression of the µDys5 protein was observed in the injected muscle.

An AAV9 vector can comprise an expression cassette (e.g., a promoter, a cDNA, and a Poly (A) site) linked to an AAV inverted terminal repeat (ITR). The ITRs may be from AAV2. The AAV9 vector can include the genomic DNA comprising the expression cassette and the ITR packaged into a vector using the capsid proteins from AAV9. SEQ ID NO:22 is an exemplary nucleic acid sequence of a CK8-µDys5 cassette with an inverted terminal repeat (ITR) attached. Such a sequence may be used to generate AAV6, AAV9, etc. Different introns, poly(A) sites, spacers, etc. may also be added to the sequence.

Example 14—Animal Experiments

Male wild type and dystrophic mdx$^{4cv}$ mice bred on a C57BL/6 inbred strain were used in this study. Animal experiments were performed in accordance with the Institutional Animal Care and Use Committee of the University of Washington. For initial screening, 5-6 week-old dystrophic mdx$^{4cv}$ mice were administered $5 \times 10^{10}$ vg of rAAV6 vector into the TA muscle. Control mice were injected with Hanks' balanced saline solution as a sham manipulation. In systemic analysis, 14-day old mdx$^{4cv}$ males were administered $10^{13}$ vg of rAAV6 vector intravenously via retro-orbital injection. Mice were sacrificed at either three or six months post-treatment for further evaluation.

Example 15—Vector Cloning and Virus Production

All micro-dystrophin transgenes were engineered using standard cloning techniques (see Chamberlain, J., PCR-mediated Mutagenesis, doi: 10.1038/npg.els.0003766 (2004)). Modified regions were subcloned into µDysHinge3 (ΔH2-R23/ΔCT, +H3) within the AAV vector genome backbone plasmid, pARAP4, using MfeI/XhoI or NheI/XhoI restriction sites flanking the majority of the central rod domain (see Banks, G. B., et al., PLOS Genetics 6, e1000958, (2010)). The polyadenylation signal from the rabbit beta-globin gene was subcloned immediately after the µDys cDNA carboxy terminus. The CMV promoter composed of the cytomegalovirus immediate early promoter and enhancer drove expression of micro-dystrophin cDNA. The CK8 regulatory cassette (see Goncalves, M. A., et al., Molecular Therapy: The Journal of the American Society of Gene Therapy 19, 1331-1341, (2011)) was subcloned in SphI/SacII sites to replace the CMV promoter and drive expression of micro-dystrophin cDNA in myogenic cells. Recombinant AAV6 vectors were made as previously described (see Gregorevic, P., et al., Nature Medicine 12, 787-789, (2006)). Briefly, expression constructs were co-transfected into HEK293 cells with pDGM6 packaging plasmid and later harvested and purified by a combination of filtration, heparin affinity chromatography, and ultracentrifugation. Viral preparations were quantified by Southern blot and quantitative PCR analysis and always in comparison to other preparations used in this study to ensure equal dosing in treating dystrophic mice.

Example 16—Histological Analysis

After physiological analysis, mice were sacrificed for necropsy. Muscles were embedded in TISSUE-TEK® O.C.T. Compound, an optimum cutting temperature formulation of water-soluble glycols and resins (SAKURA FINETEK USA™, Torrance, CA) and frozen in liquid nitrogen-cooled isopentane. Transverse sections approximately 10 µm thick were used for immunofluorescence studies. Sections were blocked in 2% gelatin and 1% Tween-20 in potassium phosphate buffered saline (KPBS). Sections were washed with 0.2% gelatin in potassium phosphate buffered saline (KPBS-G) and followed an incubation of primary antibodies diluted in 2% normal goat serum in KPBS-G. Sections were then rinsed in KPBS-G three times before incubation with secondary antibodies and DAPI, 4',6-Diamidine-2'-phenylindole dihydrochlorid (SIGMA-ALDRICH®, St. Louis, MO). After washing three more times in KPBS-G, slides were mounted in PROLONG® GOLD ANTIFADE MOUNTANT, a liquid mountant (LIFE TECHNOLOGIES™, Grand Island, NY). Primary antibodies included rabbit polyclonal N-terminal anti-dystrophin antibody (see Harper, S. Q., et al., Nature Medicine 8, 253-261, (2002)), mouse monoclonal anti-dystrophin (MANEX1011B clone 1C7, Developmental Studies Hybridoma Bank (DSHB) at the University of Iowa, Iowa City, IA) conjugated to ALEXA FLUOR® 488 DYE, a green-fluorescent dye (LIFE TECHNOLOGIES™), mouse anti-β-dystroglycan (MANDAG2 clone 7D11, DSHB) conjugated to DYLIGHT™ 594, an amine-reactive dye (THERMO FISHER SCIENTIFIC™, Rockford, IL), rat anti-α2-laminin (clone 4H8-2, SIGMA-ALDRICH®, St. Louis, MO), and rabbit anti-nNOS (Z-RNN3, LIFE TECHNOLOGIES™). Secondary antibodies were goat anti-rabbit or anti-rat conjugated to ALEXA FLUOR® 660 far-red dye or ALEXA FLUOR® 594 red-fluorescent dye, respectively (LIFE TECHNOLOGIES™). Images were captured on an OLYMPUS™ SZX16™ dissection fluorescent microscope with DP™ software (OLYMPUS™, Center Valley, PA).

Example 17—Immunoblotting

TA muscles of mice from an initial screen were snap frozen in liquid nitrogen and then ground by dry ice-chilled mortar and pestle. Muscles were homogenized in kinase assay lysis buffer (1% Triton X-100, 50 mM Tris-HCl, pH 7.5, 150 mM NaCl, 1 mM EDTA supplemented with COMPLETE™ MINI protease inhibitor cocktail tablet (ROCHE™, Indianapolis, IN). Protein concentration of lysate was determined using the PIERCE™ Coomassie Plus (Bradford) Assay (PIERCE™, Rockford, IL). 40 µg of protein was suspended in NUPAGE® LDS sample buffer (LIFE TECHNOLOGIES™) supplemented with 100 mM dithiothreitol and loaded onto a NuPAGE® 4-12% Bis-Tris polyacrylamide gel (LIFE TECHNOLOGIES™). After running the gels and transferring samples onto AMERSHAM™ HYBOND™ P polyvinylidene fluoride membrane (GE HEALTHCARE LIFE SCIENCES™ Piscataway, NJ), blots were blocked with 10% nonfat dry milk in PBS. Blots were then incubated with primary antibodies in 5% nonfat dry milk, 0.1% Tween-20 in PBS (PBST). After washing three times in PBST, secondary antibodies were incubated in 5% nonfat milk in PBST and followed by four washes in PBST. Primary antibodies included mouse anti-dystrophin (MANEX1011B clone 1C7, DSHB) and rabbit anti-glyceraldehyde 3-phosphate dehydrogenase (G9545, SIGMA-ALDRICH®) as a loading control. Secondary antibodies included donkey anti-rabbit or mouse (JACKSON IMMUNORESEARCH LABORATORIES™, West Grove, PA). Blots were developed with PIERCE™ ECL Plus Western blotting substrate (THERMO FISHER SCIENTIFIC™) and scanned using a STORM™ 860 imaging system (GE HEALTHCARE LIFE SCIENCES™).

Example 18—Functional Analyses of Skeletal Muscles

Muscles were assayed in situ (gastrocnemius) and in vitro (diaphragm) for force generation and susceptibility to contraction-induced injury as previously described with the noted modifications (see Banks, G. B., et al., Human Molecular Genetics 17, 3975-3986, (2008) and Gregorevic, P., et al., The American Journal of Pathology 161, 2263-2272, (2002)). The maximum isometric force was determined at optimal muscle fiber length and then the muscle was subjected to a series of progressively increasing length changes under stimulation (model 701C™, high-power, bi-phase stimulator, AURORA SCIENTIFIC™). Maximum isometric tetanic force was measured by stimulating at 150 Hz and 180 Hz for the gastrocnemius and diaphragm, respectively. Eccentric contractions were performed at thirty-second intervals, each comprising stimulation at a fixed length to allow peak isometric force of either 150 ms (gastrocnemius) or 100 ms (diaphragm), followed by a continued 200 ms (gastrocnemius) or 300 ms (diaphragm) of stimulation during physical lengthening of the muscle. A series of length changes, or strains, of 0-45% of the optimum length was applied to potentiate overloading of the contractile properties and damage to the muscle architecture. The result from an eccentric contraction was measured in the peak isometric force generated just prior to the subsequent eccentric contraction.

Mice were anesthetized with 2,2,2-tribromethanol (SIGMA-ALDRICH®) to be unresponsive to tactile stimuli and then prepped for in situ analysis of the gastrocnemius. The Achilles' tendon was exposed by incision at the ankle, sutured with 3-0 braided silk (ETHICON™, Cincinnati, OH), severed, and secured to the lever arm of a dual-mode force transducer-servomotor (model 305B-LR™, AURORA SCIENTIFIC™, Ontario, CA). Mice were immobilized and secured to the apparatus by a stainless steel pin inserted through the knee, and by taping the hind paw to a customized PLEXIGLAS®, poly(methyl methacrylate), platform. Gastrocnemius muscle was stimulated via two needle electrodes that were inserted through the skin on either side of the peroneal nerve in the region between the knee and hip. The servomotor's position was manipulated on three axes to help determine the optimal muscle fiber length. The servomotor was controlled by LABVIEW™ software that also allowed data acquisition (NATIONAL INSTRUMENTS®, Austin, TX).

For in vitro preparation of diaphragm, the anesthetized mouse was sacrificed after gastrocnemius analysis and the entire diaphragm muscle and surrounding ribcage was quickly excised to a dish containing oxygenated Tyrode's solution (see Lannergren, J., Bruton, et al., The Journal of Physiology 526 Pt 3, 597-611 (2000)) containing (mM): NaCl 121, KCl 5, CaCl$_2$ 1.8, MgCl$_2$ 0.5, NaH$_2$PO$_4$ 0.4, NaHCO$_3$ 24, glucose 5.5 solution as bubbled by 5% CO$_2$-95% O$_2$ mixture (pH 7.3). A diaphragm strip composed of longitudinally arranged full-length muscle fibers, a portion of the central tendon, and a portion of rib bones and intercostal muscle on the distal end of the strip was isolated under a microscope. The muscle strip was tied with needle-lead braided surgical silk (6-0, P1; ETHICON™) at the central tendon, sutured through the rib bone portion (5-0; ETHICON™) and then secured to an in situ mouse apparatus with a temperature controlled, horizontal bath (model 809A™, AURORA SCIENTIFIC™). Apparatus bath was filled with the bubbled Tryode's solution described above and maintained at 25° C. Optimal fiber length was determined and isometric and eccentric contractile properties were assessed in a manner similar to gastrocnemius muscle analysis, with the conditions specified above for the diaphragm muscle. Specific force of both muscle groups was determined by normalizing maximum isometric force to the mass of the gastrocnemius muscle or diaphragm strip, respectively. The following equation was used: specific force=maximum force×pennation×muscle length×1.04 density/muscle weight (see Burkholder, T. J., et al., Journal of Morphology 221, 177-190, (1994)). Pennation is the angle at which bundles of skeletal muscle fibers orient themselves between the tendons of the muscle. For the gastrocnemius muscle, this angle was determined by a previous study (see Banks, G. B., et al., PLOS Genetics 6, e1000958, (2010)). Diaphragm muscle strips were isolated in such a way that the myofibers would contract in a direct line between the semitendinosus junction to the myotendinous junction at the rib (see Gregorevic, P., et al., The American Journal of Pathology 161, 2263-2272, (2002)). Pennation for the gastrocnemius and diaphragm equals 0.45 and 1, respectively.

Example 19—Construction of the cTnT455 Regulatory Cassette

The cTnT455 regulatory cassette (SEQ ID NO:1; 455 indicates the number of base pairs in the RC) was constructed as described herein. DNA was prepared from human cells. PCR primers were used to amplify the cTnT enhancer/promoter region based on sequence similarity to rat and chicken cTnT sequences. The wildtype cTnT enhancer/promoter was ligated to a human placental alkaline phosphatase (AP) cDNA, and plasmid DNA was produced. cTnT-AP plasmids were transfected into newborn rat cardiomyocytes and into differentiating mouse skeletal muscle cells.

The wild type human cTnT RC (SEQ ID NO:2) had high activity in both cardiac and skeletal muscle cell cultures. cTnT's expression in skeletal muscle was initially unanticipated. Without being bound by any one particular theory, however, cTnT expression in skeletal muscle may be due to the normal activation of cardiac gene expression during early skeletal muscle development and during muscle regeneration. This property may be potentially beneficial for some gene therapy applications, for example, such as in the transient expression of a therapeutic protein only during muscle regeneration.

Figure 18:
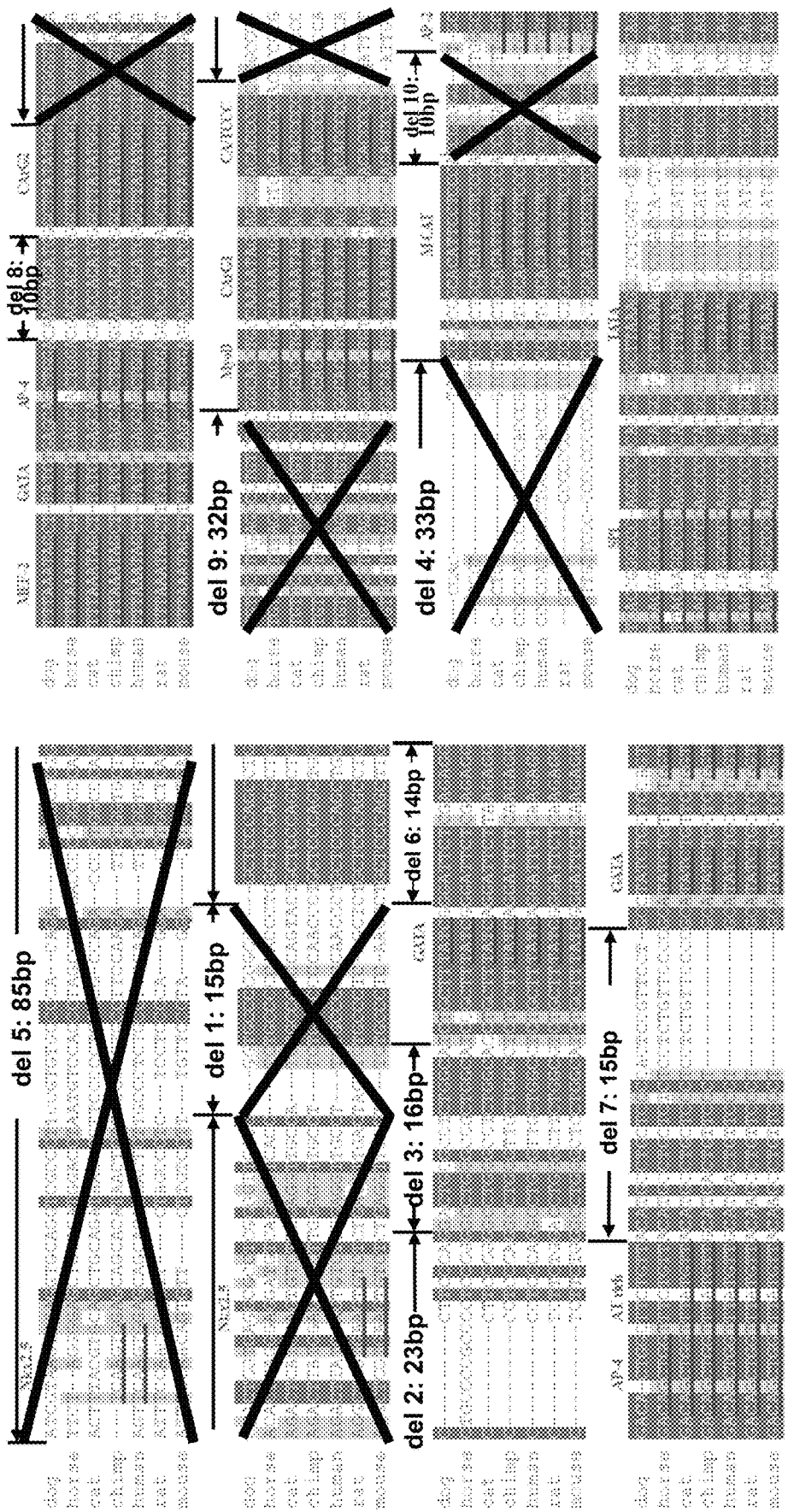
FIG. 18 illustrates miniaturization of human-cTnT (Enh+ Promoter) regulatory cassettes based on deleting sequences hypothesized to have relatively low activities.
Figure 19:
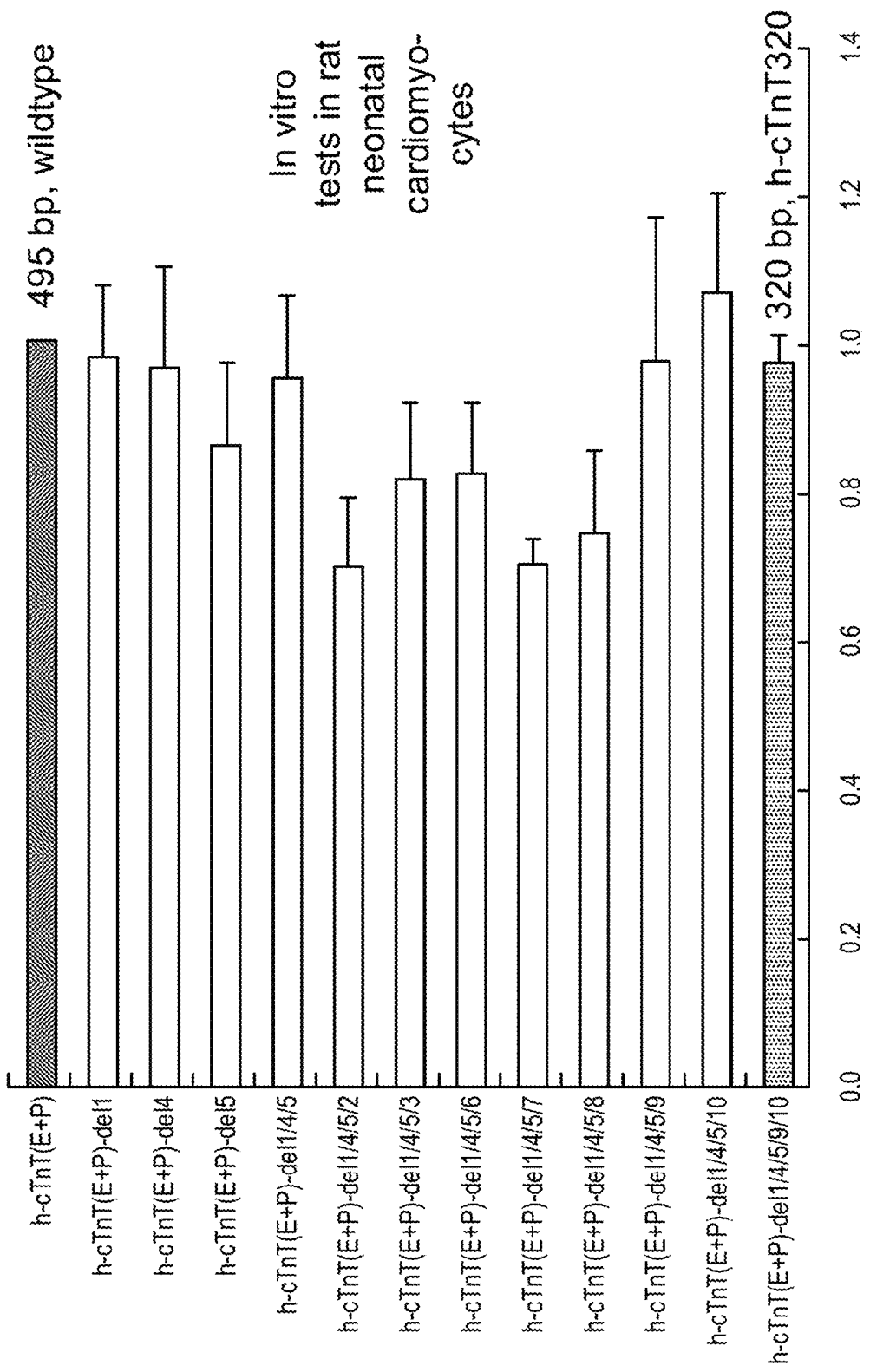
FIG. 19 illustrates transcription tests of the FIG. 18 deletions relative to a native human-cTnT enhancer/promoter; the 320 bp version retains ~95% of the activity.

The wild type cTnT enhancer was then miniaturized by removing non-conserved base sequences (based on comparisons between human, rat, dog, and chicken) as well as some conserved sequence motifs, followed by transfection tests, as discussed above, to verify that the deletions did not decrease transcriptional activity (see FIGS. 18 and 19)

Figure 20:
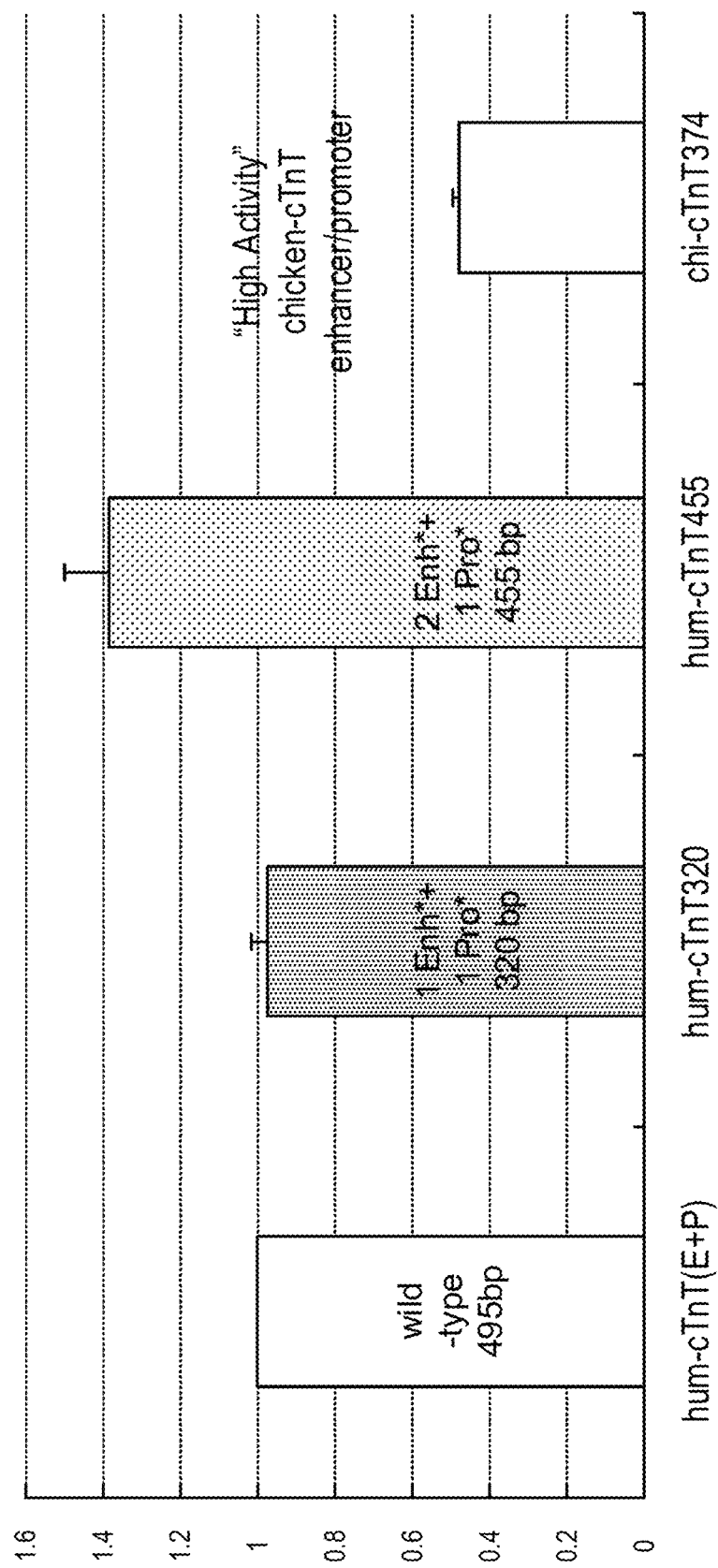
FIG. 20 illustrates increased activity of human-cTnT455 via adding a second miniaturized enhancer compared to the native enhancer/promoter, the 320 bp version, and to a Chicken cTnT promoter/enhancer (see American Journal of Physiology—Cell Physiology 280, C556-C564 (2004)).

To obtain higher activity, it was tested whether the addition of multiple miniaturized cTnT enhancers to the cTnT promoter would increase activity. These tests were carried out in cardiac and skeletal muscle cultures and cTnT455 (containing one extra enhancer) was found to be the most active (see FIG. 20).

To determine whether cTnT455 was active in vivo, the cTnT455-AP construct was packaged in rAAV6, and the vectors were administered via retro-orbital systemic delivery to mice. Four weeks later, the mice were euthanized and assays were carried out for RC expression levels in cardiac as well as skeletal muscles and non-muscle tissues. The data showed that cTnT455 had high transcriptional activity in cardiac muscle and was transcriptionally silent in both skeletal muscles and all non-muscle tissues (see Table 2; see also, PCT Application No. PCT/US2012/039897 entitled "Cell and Gene Based Methods to Improve Cardiac Function", the entirety of which is incorporated by reference herein).

Example 20—Statistical Analysis

All results are reported as mean±standard error mean. Differences between cohorts were determined using one-way and two-way ANOVA with Tukey's post hoc multiple comparison test. All data analyses were performed with GRAPHPAD™ PRISM™ 6 software (San Diego, CA).

As will be understood by one of ordinary skill in the art, each embodiment disclosed herein can comprise, consist essentially of, or consist of its particular stated element, step, ingredient, or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components, and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The applicants expect skilled artisans to employ such variations as appropriate, and the applicants intend for the various embodiments of the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above-cited references and printed publications are individually incorporated herein by reference in their entirety.

It is to be understood that the embodiments of the present disclosure are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure.

Definitions and explanations used in the present disclosure are meant and intended to be controlling in any future construction unless clearly and unambiguously modified in the examples or when application of the meaning renders any construction meaningless or essentially meaningless in cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

It will be apparent to those having skill in the art that many changes may be made to the details of the above-described embodiments without departing from the underlying principles of the invention. The scope of the present invention should, therefore, be determined only by the following claims.

The invention claimed is:

1. A method for treating a subject having muscular dystrophy or prophylactically treating a subject at risk of developing muscular dystrophy, comprising:
   administering to the subject a therapeutically effective amount of a pharmaceutical composition comprising a micro-dystrophin gene operably coupled to a regulatory cassette;
   wherein the micro-dystrophin gene encodes a protein having at least 91% sequence identity to the amino acid sequence of SEQ ID NO: 4.

2. The method of claim 1, wherein the regulatory cassette is selected from the group consisting of a CK8 promoter and a cardiac troponin T (cTnT) promoter.

3. The method of claim 1, wherein the regulatory cassette is a CK8 promoter, and wherein the CK8 promoter has at least 80% sequence identity to the nucleic acid sequence of SEQ ID NO: 19.

4. The method of claim 1, wherein the regulatory cassette is a cTnT promoter, and wherein the cTnT promoter has at least 80% sequence identity to the nucleic acid sequence of SEQ ID NO:1.

5. The method of claim 1, wherein the regulatory cassette is configured to express the micro-dystrophin gene such that a level of expression of the micro-dystrophin gene is at least 100-fold higher in striated muscle cells than the level of expression of the micro-dystrophin gene in non-muscle cells.

6. The method of claim 1, wherein the micro-dystrophin gene encodes a protein having the amino acid sequence of SEQ ID NO: 4.

* * * * *

SEQUENCE LISTING

```
<160> NUMBER OF SEQ ID NOS: 22

<210> SEQ ID NO 1
<211> LENGTH: 455
<212> TYPE: DNA
<213> ORGANISM: Artificial Sequence
<220> FEATURE:
<223> OTHER INFORMATION: hum-cTnT455

<400> SEQUENCE: 1
ctgctcccag ctggccctcc caggcctggg ttgctggcct ctgctttatc aggattctca      60
agagggacag ctggtttatg ttgcatgact gttccctgca tatctgctct ggttttaaat     120
agcttatctg ctagcctgct cccagctggc cctcccaggc ctgggttgct ggcctctgct     180
ttatcaggat tctcaagagg gacagctggt ttatgttgca tgactgttcc ctgcatatct     240
gctctggttt taaatagctt atctgagcag ctggaggacc acatgggctt atatggggca     300
cctgccaaaa tagcagccaa cacccccccc tgtcgcacat tcctccctgg ctcaccaggc     360
cccagcccac atgcctgctt aaagccctct ccatcctctg cctcacccag tccccgctga     420
gactgagcag acgcctccag gatctgtcgg cagct                                 455

<210> SEQ ID NO 2
<211> LENGTH: 495
<212> TYPE: DNA
<213> ORGANISM: Homo sapiens

<400> SEQUENCE: 2
agttcaagtg gagcagcaca taactcttgc cctctgcctt ccaagattct ggtgctgaga      60
cttatggagt gtcttggagg ttgccttctg cccccaacc ctgctcccag ctggccctcc      120
caggcctggg ttgctggcct ctgctttatc aggattctca agagggacag ctggtttatg     180
ttgcatgact gttccctgca tatctgctct ggttttaaat agcttatctg agcagctgga     240
ggaccacatg ggcttatatg gcgtggggta catgttcctg tagccttgtc cctggcacct     300
gccaaaatag cagccaacac ccccacccc caccgccatc ccctgcccc acccgtcccc       360 tgtcgcacat tcctccctcc gcagggctgg ctcaccaggc cccagcccac atgcctgctt     420
aaagccctct ccatcctctg cctcacccag tccccgctga gactgagcag acgcctccag     480
gatctgtcgg cagct                                                        495

<210> SEQ ID NO 3
<211> LENGTH: 1188
<212> TYPE: PRT
<213> ORGANISM: Artificial Sequence
<220> FEATURE:
<223> OTHER INFORMATION: micro-DysH3

<400> SEQUENCE: 3

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30
```

-continued

```
Gly Lys Gln His Ile Glu Asn Leu Phe Ser Asp Leu Gln Asp Gly Arg
         35                  40                  45
Arg Leu Leu Asp Leu Leu Glu Gly Leu Thr Gly Gln Lys Leu Pro Lys
 50                  55                  60
Glu Lys Gly Ser Thr Arg Val His Ala Leu Asn Asn Val Asn Lys Ala
 65                  70                  75                  80
Leu Arg Val Leu Gln Asn Asn Val Asp Leu Val Asn Ile Gly Ser
                 85                  90                  95
Thr Asp Ile Val Asp Gly Asn His Lys Leu Thr Leu Gly Leu Ile Trp
            100                 105                 110
Asn Ile Ile Leu His Trp Gln Val Lys Asn Val Met Lys Asn Ile Met
            115                 120                 125
Ala Gly Leu Gln Gln Thr Asn Ser Glu Lys Ile Leu Leu Ser Trp Val
130                 135                 140
Arg Gln Ser Thr Arg Asn Tyr Pro Gln Val Asn Val Ile Asn Phe Thr
145                 150                 155                 160
Thr Ser Trp Ser Asp Gly Leu Ala Leu Asn Ala Leu Ile His Ser His
                165                 170                 175
Arg Pro Asp Leu Phe Asp Trp Asn Ser Val Val Cys Gln Gln Ser Ala
            180                 185                 190
Thr Gln Arg Leu Glu His Ala Phe Asn Ile Ala Arg Tyr Gln Leu Gly
            195                 200                 205
Ile Glu Lys Leu Leu Asp Pro Glu Asp Val Asp Thr Thr Tyr Pro Asp
        210                 215                 220
Lys Lys Ser Ile Leu Met Tyr Ile Thr Ser Leu Phe Gln Val Leu Pro
225                 230                 235                 240
Gln Gln Val Ser Ile Glu Ala Ile Gln Glu Val Glu Met Leu Pro Arg
                245                 250                 255
Pro Pro Lys Val Thr Lys Glu Glu His Phe Gln Leu His His Gln Met
            260                 265                 270
His Tyr Ser Gln Gln Ile Thr Val Ser Leu Ala Gln Gly Tyr Glu Arg
            275                 280                 285
Thr Ser Ser Pro Lys Pro Arg Phe Lys Ser Tyr Ala Tyr Thr Gln Ala
290                 295                 300
Ala Tyr Val Thr Thr Ser Asp Pro Thr Arg Ser Pro Phe Pro Ser Gln
305                 310                 315                 320
His Leu Glu Ala Pro Glu Asp Lys Ser Phe Gly Ser Ser Leu Met Glu
                325                 330                 335
Ser Glu Val Asn Leu Asp Arg Tyr Gln Thr Ala Leu Glu Glu Val Leu
            340                 345                 350
Ser Trp Leu Leu Ser Ala Glu Asp Thr Leu Gln Ala Gln Gly Glu Ile
            355                 360                 365
Ser Asn Asp Val Glu Val Val Lys Asp Gln Phe His Thr His Glu Gly
        370                 375                 380
Tyr Met Met Asp Leu Thr Ala His Gln Gly Arg Val Gly Asn Ile Leu
385                 390                 395                 400
Gln Leu Gly Ser Lys Leu Ile Gly Thr Gly Lys Leu Ser Glu Asp Glu
                405                 410                 415
Glu Thr Glu Val Gln Glu Gln Met Asn Leu Leu Asn Ser Arg Trp Glu
            420                 425                 430
Cys Leu Arg Val Ala Ser Met Glu Lys Gln Ser Asn Leu His Arg Val
            435                 440                 445
Leu Met Asp Leu Gln Asn Gln Lys Leu Lys Glu Leu Asn Asp Trp Leu
```

```
                450             455             460
Thr Lys Thr Glu Glu Arg Thr Arg Lys Met Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Gln Val Arg Val Asn Ser Leu Thr His
                500                 505                 510

Met Val Val Val Asp Glu Ser Ser Gly Asp His Ala Thr Ala Ala
                515                 520                 525

Leu Glu Glu Gln Leu Lys Val Leu Gly Asp Arg Trp Ala Asn Ile Cys
530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
                580                 585                 590

Gln Asn Glu Met Leu Ser Ser Leu Gln Lys Leu Ala Val Leu Lys Ala
                595                 600                 605

Asp Leu Glu Lys Lys Lys Gln Ser Met Gly Lys Leu Tyr Ser Leu Lys
                610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Ala Pro Gly Leu
                660                 665                 670

Thr Thr Ile Gly Ala Ser Pro Thr Gln Thr Val Thr Leu Val Thr Gln
                675                 680                 685

Pro Val Val Thr Lys Glu Thr Ala Ile Ser Lys Leu Glu Met Pro Ser
690                 695                 700

Ser Leu Met Leu Glu Leu Glu Arg Leu Gln Glu Leu Gln Glu Ala Thr
705                 710                 715                 720

Asp Glu Leu Asp Leu Lys Leu Arg Gln Ala Glu Val Ile Lys Gly Ser
                725                 730                 735

Trp Gln Pro Val Gly Asp Leu Leu Ile Asp Ser Leu Gln Asp His Leu
                740                 745                 750

Glu Lys Val Lys Ala Leu Arg Gly Glu Ile Ala Pro Leu Lys Glu Asn
                755                 760                 765

Val Ser His Val Asn Asp Leu Ala Arg Gln Leu Thr Thr Leu Gly Ile
770                 775                 780

Gln Leu Ser Pro Tyr Asn Leu Ser Thr Leu Glu Asp Leu Asn Thr Arg
785                 790                 795                 800

Trp Lys Leu Leu Gln Val Ala Val Glu Asp Arg Val Arg Gln Leu His
                805                 810                 815

Glu Ala His Arg Asp Phe Gly Pro Ala Ser Gln His Phe Leu Ser Thr
                820                 825                 830

Ser Val Gln Gly Pro Trp Glu Arg Ala Ile Ser Pro Asn Lys Val Pro
                835                 840                 845

Tyr Tyr Ile Asn His Glu Thr Gln Thr Thr Cys Trp Asp His Pro Lys
                850                 855                 860

Met Thr Glu Leu Tyr Gln Ser Leu Ala Asp Leu Asn Asn Val Arg Phe
865                 870                 875                 880
```

```
Ser Ala Tyr Arg Thr Ala Met Lys Leu Arg Arg Leu Gln Lys Ala Leu
            885                 890                 895

Cys Leu Asp Leu Leu Ser Leu Ser Ala Ala Cys Asp Ala Leu Asp Gln
        900                 905                 910

His Asn Leu Lys Gln Asn Asp Gln Pro Met Asp Ile Leu Gln Ile Ile
        915                 920                 925

Asn Cys Leu Thr Thr Ile Tyr Asp Arg Leu Glu Gln Glu His Asn Asn
        930                 935                 940

Leu Val Asn Val Pro Leu Cys Val Asp Met Cys Leu Asn Trp Leu Leu
945                 950                 955                 960

Asn Val Tyr Asp Thr Gly Arg Thr Gly Arg Ile Arg Val Leu Ser Phe
            965                 970                 975

Lys Thr Gly Ile Ile Ser Leu Cys Lys Ala His Leu Glu Asp Lys Tyr
            980                 985                 990

Arg Tyr Leu Phe Lys Gln Val Ala Ser Ser Thr Gly Phe Cys Asp Gln
            995                 1000                1005

Arg Arg Leu Gly Leu Leu Leu His Asp Ser Ile Gln Ile Pro Arg
        1010                1015                1020

Gln Leu Gly Glu Val Ala Ser Phe Gly Gly Ser Asn Ile Glu Pro
        1025                1030                1035

Ser Val Arg Ser Cys Phe Gln Phe Ala Asn Asn Lys Pro Glu Ile
        1040                1045                1050

Glu Ala Ala Leu Phe Leu Asp Trp Met Arg Leu Glu Pro Gln Ser
        1055                1060                1065

Met Val Trp Leu Pro Val Leu His Arg Val Ala Ala Ala Glu Thr
        1070                1075                1080

Ala Lys His Gln Ala Lys Cys Asn Ile Cys Lys Glu Cys Pro Ile
        1085                1090                1095

Ile Gly Phe Arg Tyr Arg Ser Leu Lys His Phe Asn Tyr Asp Ile
        1100                1105                1110

Cys Gln Ser Cys Phe Phe Ser Gly Arg Val Ala Lys Gly His Lys
        1115                1120                1125

Met His Tyr Pro Met Val Glu Tyr Cys Thr Pro Thr Thr Ser Gly
        1130                1135                1140

Glu Asp Val Arg Asp Phe Ala Lys Val Leu Lys Asn Lys Phe Arg
        1145                1150                1155

Thr Lys Arg Tyr Phe Ala Lys His Pro Arg Met Gly Tyr Leu Pro
        1160                1165                1170

Val Gln Thr Val Leu Glu Gly Asp Asn Met Glu Thr Asp Thr Met
        1175                1180                1185

<210> SEQ ID NO 4
<211> LENGTH: 1270
<212> TYPE: PRT
<213> ORGANISM: Artificial Sequence
<220> FEATURE:
<223> OTHER INFORMATION: micro-Dys5

<400> SEQUENCE: 4

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45
```

```
Arg Leu Leu Asp Leu Leu Glu Gly Leu Thr Gly Gln Lys Leu Pro Lys
 50                  55                  60

Glu Lys Gly Ser Thr Arg Val His Ala Leu Asn Asn Val Asn Lys Ala
 65                  70                  75                  80

Leu Arg Val Leu Gln Asn Asn Asn Val Asp Leu Val Asn Ile Gly Ser
                     85                  90                  95

Thr Asp Ile Val Asp Gly Asn His Lys Leu Thr Leu Gly Leu Ile Trp
                100                 105                 110

Asn Ile Ile Leu His Trp Gln Val Lys Asn Val Met Lys Asn Ile Met
            115                 120                 125

Ala Gly Leu Gln Gln Thr Asn Ser Glu Lys Ile Leu Leu Ser Trp Val
130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
                180                 185                 190

Thr Gln Arg Leu Glu His Ala Phe Asn Ile Ala Arg Tyr Gln Leu Gly
                195                 200                 205

Ile Glu Lys Leu Leu Asp Pro Glu Asp Val Asp Thr Thr Tyr Pro Asp
210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
                340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
                420                 425                 430

Cys Leu Arg Val Ala Ser Met Glu Lys Gln Ser Asn Leu His Ser Tyr
                435                 440                 445

Val Pro Ser Thr Tyr Leu Thr Glu Ile Thr His Val Ser Gln Ala Leu
450                 455                 460
```

```
Leu Glu Val Glu Gln Leu Asn Ala Pro Asp Leu Cys Ala Lys Asp
465                 470                 475                 480

Phe Glu Asp Leu Phe Lys Gln Glu Glu Ser Leu Lys Asn Ile Lys Asp
                485                 490                 495

Ser Leu Gln Gln Ser Ser Gly Arg Ile Asp Ile Ile His Ser Lys Lys
                500                 505                 510

Thr Ala Ala Leu Gln Ser Ala Thr Pro Val Glu Arg Val Lys Leu Gln
                515                 520                 525

Glu Ala Leu Ser Gln Leu Asp Phe Gln Trp Glu Lys Val Asn Lys Met
530                 535                 540

Tyr Lys Asp Arg Gln Gly Arg Phe Asp Arg Ser Val Glu Lys Trp Arg
545                 550                 555                 560

Arg Phe His Tyr Asp Ile Lys Ile Phe Asn Gln Trp Leu Thr Glu Ala
                565                 570                 575

Glu Gln Phe Leu Arg Lys Thr Gln Ile Pro Glu Asn Trp Glu His Ala
                580                 585                 590

Lys Tyr Lys Trp Tyr Leu Lys Glu Leu Gln Asp Gly Ile Gly Gln Arg
                595                 600                 605

Gln Thr Val Val Arg Thr Leu Asn Ala Thr Gly Glu Glu Ile Ile Gln
610                 615                 620

Gln Ser Ser Lys Thr Asp Ala Ser Ile Leu Gln Glu Lys Leu Gly Ser
625                 630                 635                 640

Leu Asn Leu Arg Trp Gln Glu Val Cys Lys Gln Leu Ser Asp Arg Lys
                645                 650                 655

Lys Arg Leu Glu Glu Gln Ser Asp Gln Trp Lys Arg Leu His Leu Ser
                660                 665                 670

Leu Gln Glu Leu Leu Val Trp Leu Gln Leu Lys Asp Asp Glu Leu Ser
                675                 680                 685

Arg Gln Ala Pro Ile Gly Gly Asp Phe Pro Ala Val Gln Lys Gln Asn
690                 695                 700

Asp Val His Arg Ala Phe Lys Arg Glu Leu Lys Thr Lys Glu Pro Val
705                 710                 715                 720

Ile Met Ser Thr Leu Glu Thr Val Arg Ile Phe Leu Thr Glu Gln Pro
                725                 730                 735

Leu Glu Gly Leu Glu Lys Leu Tyr Gln Glu Pro Arg Glu Leu Pro Pro
                740                 745                 750

Glu Glu Arg Ala Gln Asn Val Thr Arg Leu Leu Arg Lys Gln Ala Glu
                755                 760                 765

Glu Val Asn Thr Glu Trp Glu Lys Leu Asn Leu His Ser Ala Asp Trp
770                 775                 780

Gln Arg Lys Ile Asp Glu Thr Leu Glu Arg Leu Gln Glu Leu Gln Glu
785                 790                 795                 800

Ala Thr Asp Glu Leu Asp Leu Lys Leu Arg Gln Ala Glu Val Ile Lys
                805                 810                 815

Gly Ser Trp Gln Pro Val Gly Asp Leu Leu Ile Asp Ser Leu Gln Asp
                820                 825                 830

His Leu Glu Lys Val Lys Ala Leu Arg Gly Glu Ile Ala Pro Leu Lys
                835                 840                 845

Glu Asn Val Ser His Val Asn Asp Leu Ala Arg Gln Leu Thr Thr Leu
                850                 855                 860

Gly Ile Gln Leu Ser Pro Tyr Asn Leu Ser Thr Leu Glu Asp Leu Asn
865                 870                 875                 880

Thr Arg Trp Lys Leu Leu Gln Val Ala Val Glu Asp Arg Val Arg Gln
```

885                 890                 895
Leu His Glu Ala His Arg Asp Phe Gly Pro Ala Ser Gln His Phe Leu
                900                 905                 910

Ser Thr Ser Val Gln Gly Pro Trp Glu Arg Ala Ile Ser Pro Asn Lys
        915                 920                 925

Val Pro Tyr Tyr Ile Asn His Glu Thr Gln Thr Thr Cys Trp Asp His
    930                 935                 940

Pro Lys Met Thr Glu Leu Tyr Gln Ser Leu Ala Asp Leu Asn Asn Val
945                 950                 955                 960

Arg Phe Ser Ala Tyr Arg Thr Ala Met Lys Leu Arg Arg Leu Gln Lys
            965                 970                 975

Ala Leu Cys Leu Asp Leu Leu Ser Leu Ser Ala Ala Cys Asp Ala Leu
                980                 985                 990

Asp Gln His Asn Leu Lys Gln Asn Asp Gln Pro Met Asp Ile Leu Gln
            995                 1000                1005

Ile Ile Asn Cys Leu Thr Thr Ile Tyr Asp Arg Leu Glu Gln Glu
    1010                1015                1020

His Asn Asn Leu Val Asn Val Pro Leu Cys Val Asp Met Cys Leu
    1025                1030                1035

Asn Trp Leu Leu Asn Val Tyr Asp Thr Gly Arg Thr Gly Arg Ile
    1040                1045                1050

Arg Val Leu Ser Phe Lys Thr Gly Ile Ile Ser Leu Cys Lys Ala
    1055                1060                1065

His Leu Glu Asp Lys Tyr Arg Tyr Leu Phe Lys Gln Val Ala Ser
    1070                1075                1080

Ser Thr Gly Phe Cys Asp Gln Arg Arg Leu Gly Leu Leu Leu His
    1085                1090                1095

Asp Ser Ile Gln Ile Pro Arg Gln Leu Gly Glu Val Ala Ser Phe
    1100                1105                1110

Gly Gly Ser Asn Ile Glu Pro Ser Val Arg Ser Cys Phe Gln Phe
    1115                1120                1125

Ala Asn Asn Lys Pro Glu Ile Glu Ala Ala Leu Phe Leu Asp Trp
    1130                1135                1140

Met Arg Leu Glu Pro Gln Ser Met Val Trp Leu Pro Val Leu His
    1145                1150                1155

Arg Val Ala Ala Ala Glu Thr Ala Lys His Gln Ala Lys Cys Asn
    1160                1165                1170

Ile Cys Lys Glu Cys Pro Ile Ile Gly Phe Arg Tyr Arg Ser Leu
    1175                1180                1185

Lys His Phe Asn Tyr Asp Ile Cys Gln Ser Cys Phe Phe Ser Gly
    1190                1195                1200

Arg Val Ala Lys Gly His Lys Met His Tyr Pro Met Val Glu Tyr
    1205                1210                1215

Cys Thr Pro Thr Thr Ser Gly Glu Asp Val Arg Asp Phe Ala Lys
    1220                1225                1230

Val Leu Lys Asn Lys Phe Arg Thr Lys Arg Tyr Phe Ala Lys His
    1235                1240                1245

Pro Arg Met Gly Tyr Leu Pro Val Gln Thr Val Leu Glu Gly Asp
    1250                1255                1260

Asn Met Glu Thr Asp Thr Met
    1265                1270

<210> SEQ ID NO 5

```
<211> LENGTH: 1404
<212> TYPE: PRT
<213> ORGANISM: Artificial Sequence
<220> FEATURE:
<223> OTHER INFORMATION: micro-Dys7

<400> SEQUENCE: 5
```

| | | | | | | | | | | | | | | |
|---|---|---|---|---|---|---|---|---|---|---|---|---|---|---|
| Met | Leu | Trp | Trp | Glu | Glu | Val | Glu | Asp | Cys | Tyr | Glu | Arg | Glu | Asp | Val |
| 1 | | | | 5 | | | | | 10 | | | | | 15 | |

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
370                 375                 380

```
Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
            405                 410                 415

Glu Thr Glu Val Gln Glu Gln Met Asn Leu Leu Asn Ser Arg Trp Glu
        420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
450                 455                 460

Thr Lys Thr Glu Glu Arg Thr Arg Lys Met Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
            565                 570                 575

Glu Lys Glu Asp Ala Val Asn Lys Ile His Thr Thr Gly Phe Lys Asp
        580                 585                 590

Gln Asn Glu Met Leu Ser Ser Leu Gln Lys Leu Ala Val Leu Lys Ala
    595                 600                 605

Asp Leu Glu Lys Lys Lys Gln Ser Met Gly Lys Leu Tyr Ser Leu Lys
610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
            645                 650                 655

Lys Leu Glu Lys Ser Thr Ala Gln Ile Ser Gln Ala Ala Pro Gly Leu
        660                 665                 670

Thr Thr Ile Gly Ala Ser Pro Thr Gln Thr Val Thr Leu Val Thr Gln
            675                 680                 685

Pro Val Val Thr Lys Glu Thr Ala Ile Ser Lys Leu Glu Met Pro Ser
        690                 695                 700

Ser Leu Met Leu Glu Ser Tyr Val Pro Ser Thr Tyr Leu Thr Glu Ile
705                 710                 715                 720

Thr His Val Ser Gln Ala Leu Leu Glu Val Glu Gln Leu Leu Asn Ala
            725                 730                 735

Pro Asp Leu Cys Ala Lys Asp Phe Glu Asp Leu Phe Lys Gln Glu Glu
            740                 745                 750

Ser Leu Lys Asn Ile Lys Asp Ser Leu Gln Gln Ser Ser Gly Arg Ile
        755                 760                 765

Asp Ile Ile His Ser Lys Lys Thr Ala Ala Leu Gln Ser Ala Thr Pro
770                 775                 780

Val Glu Arg Val Lys Leu Gln Glu Ala Leu Ser Gln Leu Asp Phe Gln
785                 790                 795                 800
```

-continued

```
Trp Glu Lys Val Asn Lys Met Tyr Lys Asp Arg Gln Gly Arg Phe Asp
            805                 810                 815
Arg Ser Val Glu Lys Trp Arg Arg Phe His Tyr Asp Ile Lys Ile Phe
            820                 825                 830
Asn Gln Trp Leu Thr Glu Ala Glu Gln Phe Leu Arg Lys Thr Gln Ile
            835                 840                 845
Pro Glu Asn Trp Glu His Ala Lys Tyr Lys Trp Tyr Leu Lys Glu Leu
850                 855                 860
Gln Asp Gly Ile Gly Gln Arg Gln Thr Val Val Arg Thr Leu Asn Ala
865                 870                 875                 880
Thr Gly Glu Glu Ile Ile Gln Gln Ser Ser Lys Thr Asp Ala Ser Ile
            885                 890                 895
Leu Gln Glu Lys Leu Gly Ser Leu Asn Leu Arg Trp Gln Glu Val Cys
            900                 905                 910
Lys Gln Leu Ser Asp Arg Lys Lys Arg Leu Glu Glu Gln Leu Glu Arg
            915                 920                 925
Leu Gln Glu Leu Gln Glu Ala Thr Asp Glu Leu Asp Leu Lys Leu Arg
            930                 935                 940
Gln Ala Glu Val Ile Lys Gly Ser Trp Gln Pro Val Gly Asp Leu Leu
945                 950                 955                 960
Ile Asp Ser Leu Gln Asp His Leu Glu Lys Val Lys Ala Leu Arg Gly
            965                 970                 975
Glu Ile Ala Pro Leu Lys Glu Asn Val Ser His Val Asn Asp Leu Ala
            980                 985                 990
Arg Gln Leu Thr Thr Leu Gly Ile Gln Leu Ser Pro Tyr Asn Leu Ser
            995                 1000                1005
Thr Leu Glu Asp Leu Asn Thr Arg Trp Lys Leu Leu Gln Val Ala
            1010                1015                1020
Val Glu Asp Arg Val Arg Gln Leu His Glu Ala His Arg Asp Phe
            1025                1030                1035
Gly Pro Ala Ser Gln His Phe Leu Ser Thr Ser Val Gln Gly Pro
            1040                1045                1050
Trp Glu Arg Ala Ile Ser Pro Asn Lys Val Pro Tyr Tyr Ile Asn
            1055                1060                1065
His Glu Thr Gln Thr Thr Cys Trp Asp His Pro Lys Met Thr Glu
            1070                1075                1080
Leu Tyr Gln Ser Leu Ala Asp Leu Asn Asn Val Arg Phe Ser Ala
            1085                1090                1095
Tyr Arg Thr Ala Met Lys Leu Arg Arg Leu Gln Lys Ala Leu Cys
            1100                1105                1110
Leu Asp Leu Leu Ser Leu Ser Ala Ala Cys Asp Ala Leu Asp Gln
            1115                1120                1125
His Asn Leu Lys Gln Asn Asp Gln Pro Met Asp Ile Leu Gln Ile
            1130                1135                1140
Ile Asn Cys Leu Thr Thr Ile Tyr Asp Arg Leu Glu Gln Glu His
            1145                1150                1155
Asn Asn Leu Val Asn Val Pro Leu Cys Val Asp Met Cys Leu Asn
            1160                1165                1170
Trp Leu Leu Asn Val Tyr Asp Thr Gly Arg Thr Gly Arg Ile Arg
            1175                1180                1185
Val Leu Ser Phe Lys Thr Gly Ile Ile Ser Leu Cys Lys Ala His
            1190                1195                1200
Leu Glu Asp Lys Tyr Arg Tyr Leu Phe Lys Gln Val Ala Ser Ser
```

-continued

```
            1205                1210                1215

Thr Gly Phe Cys Asp Gln Arg Arg Leu Gly Leu Leu Leu His Asp
        1220                1225                1230

Ser Ile Gln Ile Pro Arg Gln Leu Gly Glu Val Ala Ser Phe Gly
        1235                1240                1245

Gly Ser Asn Ile Glu Pro Ser Val Arg Ser Cys Phe Gln Phe Ala
        1250                1255                1260

Asn Asn Lys Pro Glu Ile Glu Ala Ala Leu Phe Leu Asp Trp Met
        1265                1270                1275

Arg Leu Glu Pro Gln Ser Met Val Trp Leu Pro Val Leu His Arg
        1280                1285                1290

Val Ala Ala Ala Glu Thr Ala Lys His Gln Ala Lys Cys Asn Ile
        1295                1300                1305

Cys Lys Glu Cys Pro Ile Ile Gly Phe Arg Tyr Arg Ser Leu Lys
        1310                1315                1320

His Phe Asn Tyr Asp Ile Cys Gln Ser Cys Phe Phe Ser Gly Arg
        1325                1330                1335

Val Ala Lys Gly His Lys Met His Tyr Pro Met Val Glu Tyr Cys
        1340                1345                1350

Thr Pro Thr Thr Ser Gly Glu Asp Val Arg Asp Phe Ala Lys Val
        1355                1360                1365

Leu Lys Asn Lys Phe Arg Thr Lys Arg Tyr Phe Ala Lys His Pro
        1370                1375                1380

Arg Met Gly Tyr Leu Pro Val Gln Thr Val Leu Glu Gly Asp Asn
        1385                1390                1395

Met Glu Thr Asp Thr Met
        1400

<210> SEQ ID NO 6
<211> LENGTH: 1190
<212> TYPE: PRT
<213> ORGANISM: Artificial Sequence
<220> FEATURE:
<223> OTHER INFORMATION: micro-Dys1

<400> SEQUENCE: 6

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
```

```
                145                 150                 155                 160
Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
                180                 185                 190

Thr Gln Arg Leu Glu His Ala Phe Asn Ile Ala Arg Tyr Gln Leu Gly
                195                 200                 205

Ile Glu Lys Leu Leu Asp Pro Glu Asp Val Asp Thr Thr Tyr Pro Asp
                210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
                260                 265                 270

His Tyr Ser Gln Gln Ile Thr Val Ser Leu Ala Gln Gly Tyr Glu Arg
                275                 280                 285

Thr Ser Ser Pro Lys Pro Arg Phe Lys Ser Tyr Ala Tyr Thr Gln Ala
                290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
                340                 345                 350

Ser Trp Leu Leu Ser Ala Glu Asp Thr Leu Gln Ala Gln Gly Glu Ile
                355                 360                 365

Ser Asn Asp Val Glu Val Val Lys Asp Gln Phe His Thr His Glu Gly
                370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
                420                 425                 430

Cys Leu Arg Val Ala Ser Met Glu Lys Gln Ser Asn Leu His Arg Val
                435                 440                 445

Leu Met Asp Leu Gln Asn Gln Lys Leu Lys Glu Leu Asn Asp Trp Leu
450                 455                 460

Thr Lys Thr Glu Glu Arg Thr Arg Lys Met Glu Glu Pro Leu Gly
465                 470                 475                 480

Pro Asp Leu Glu Asp Leu Lys Arg Gln Val Gln His Lys Val Leu
                485                 490                 495

Gln Glu Asp Leu Glu Gln Glu Gln Val Arg Val Asn Ser Leu Thr His
                500                 505                 510

Met Val Val Val Asp Glu Ser Ser Gly Asp His Ala Thr Ala Ala
                515                 520                 525

Leu Glu Glu Gln Leu Lys Val Leu Gly Asp Arg Trp Ala Asn Ile Cys
                530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575
```

-continued

Glu Lys Glu Asp Ala Val Asn Lys Ile His Thr Thr Gly Phe Lys Asp
              580                 585                 590

Gln Asn Glu Met Leu Ser Ser Leu Gln Lys Leu Ala Val Leu Lys Ala
              595                 600                 605

Asp Leu Glu Lys Lys Gln Ser Met Gly Lys Leu Tyr Ser Leu Lys
              610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
              645                 650                 655

Lys Leu Glu Lys Ser Thr Ala Gln Ile Ser Gln Ala Glu Leu Pro Pro
              660                 665                 670

Glu Glu Arg Ala Gln Asn Val Thr Arg Leu Leu Arg Lys Gln Ala Glu
              675                 680                 685

Glu Val Asn Thr Glu Trp Glu Lys Leu Asn Leu His Ser Ala Asp Trp
              690                 695                 700

Gln Arg Lys Ile Asp Glu Thr Leu Glu Arg Leu Gln Glu Leu Gln Glu
705                 710                 715                 720

Ala Thr Asp Glu Leu Asp Leu Lys Leu Arg Gln Ala Glu Val Ile Lys
              725                 730                 735

Gly Ser Trp Gln Pro Val Gly Asp Leu Leu Ile Asp Ser Leu Gln Asp
              740                 745                 750

His Leu Glu Lys Val Lys Ala Leu Arg Gly Glu Ile Ala Pro Leu Lys
              755                 760                 765

Glu Asn Val Ser His Val Asn Asp Leu Ala Arg Gln Leu Thr Thr Leu
              770                 775                 780

Gly Ile Gln Leu Ser Pro Tyr Asn Leu Ser Thr Leu Glu Asp Leu Asn
785                 790                 795                 800

Thr Arg Trp Lys Leu Leu Gln Val Ala Val Glu Asp Arg Val Arg Gln
              805                 810                 815

Leu His Glu Ala His Arg Asp Phe Gly Pro Ala Ser Gln His Phe Leu
              820                 825                 830

Ser Thr Ser Val Gln Gly Pro Trp Glu Arg Ala Ile Ser Pro Asn Lys
              835                 840                 845

Val Pro Tyr Tyr Ile Asn His Glu Thr Gln Thr Thr Cys Trp Asp His
850                 855                 860

Pro Lys Met Thr Glu Leu Tyr Gln Ser Leu Ala Asp Leu Asn Asn Val
865                 870                 875                 880

Arg Phe Ser Ala Tyr Arg Thr Ala Met Lys Leu Arg Arg Leu Gln Lys
              885                 890                 895

Ala Leu Cys Leu Asp Leu Leu Ser Leu Ser Ala Ala Cys Asp Ala Leu
              900                 905                 910

Asp Gln His Asn Leu Lys Gln Asn Asp Gln Pro Met Asp Ile Leu Gln
              915                 920                 925

Ile Ile Asn Cys Leu Thr Thr Ile Tyr Asp Arg Leu Glu Gln Glu His
              930                 935                 940

Asn Asn Leu Val Asn Val Pro Leu Cys Val Asp Met Cys Leu Asn Trp
945                 950                 955                 960

Leu Leu Asn Val Tyr Asp Thr Gly Arg Thr Gly Arg Ile Arg Val Leu
              965                 970                 975

Ser Phe Lys Thr Gly Ile Ile Ser Leu Cys Lys Ala His Leu Glu Asp
              980                 985                 990

```
Lys Tyr Arg Tyr Leu Phe Lys Gln Val Ala Ser Ser Thr Gly Phe Cys
            995                 1000                1005

Asp Gln Arg Arg Leu Gly Leu Leu Leu His Asp Ser Ile Gln Ile
    1010                1015                1020

Pro Arg Gln Leu Gly Glu Val Ala Ser Phe Gly Gly Ser Asn Ile
    1025                1030                1035

Glu Pro Ser Val Arg Ser Cys Phe Gln Phe Ala Asn Asn Lys Pro
    1040                1045                1050

Glu Ile Glu Ala Ala Leu Phe Leu Asp Trp Met Arg Leu Glu Pro
    1055                1060                1065

Gln Ser Met Val Trp Leu Pro Val Leu His Arg Val Ala Ala Ala
    1070                1075                1080

Glu Thr Ala Lys His Gln Ala Lys Cys Asn Ile Cys Lys Glu Cys
    1085                1090                1095

Pro Ile Ile Gly Phe Arg Tyr Arg Ser Leu Lys His Phe Asn Tyr
    1100                1105                1110

Asp Ile Cys Gln Ser Cys Phe Phe Ser Gly Arg Val Ala Lys Gly
    1115                1120                1125

His Lys Met His Tyr Pro Met Val Glu Tyr Cys Thr Pro Thr Thr
    1130                1135                1140

Ser Gly Glu Asp Val Arg Asp Phe Ala Lys Val Leu Lys Asn Lys
    1145                1150                1155

Phe Arg Thr Lys Arg Tyr Phe Ala Lys His Pro Arg Met Gly Tyr
    1160                1165                1170

Leu Pro Val Gln Thr Val Leu Glu Gly Asp Asn Met Glu Thr Asp
    1175                1180                1185

Thr Met
    1190

<210> SEQ ID NO 7
<211> LENGTH: 1184
<212> TYPE: PRT
<213> ORGANISM: Artificial Sequence
<220> FEATURE:
<223> OTHER INFORMATION: micro-Dys2

<400> SEQUENCE: 7

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140
```

-continued

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
            165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
            195                 200                 205

Ile Glu Lys Leu Leu Asp Pro Glu Asp Val Asp Thr Thr Tyr Pro Asp
210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Ser Tyr
        435                 440                 445

Val Pro Ser Thr Tyr Leu Thr Glu Ile Thr His Val Ser Gln Ala Leu
    450                 455                 460

Leu Glu Val Glu Gln Leu Leu Asn Ala Pro Asp Leu Cys Ala Lys Asp
465                 470                 475                 480

Phe Glu Asp Leu Phe Lys Gln Glu Glu Ser Leu Lys Asn Ile Lys Asp
                485                 490                 495

Ser Leu Gln Gln Ser Ser Gly Arg Ile Asp Ile Ile His Ser Lys Lys
            500                 505                 510

Thr Ala Ala Leu Gln Ser Ala Thr Pro Val Glu Arg Val Lys Leu Gln
        515                 520                 525

Glu Ala Leu Ser Gln Leu Asp Phe Gln Trp Glu Lys Val Asn Lys Met
    530                 535                 540

Tyr Lys Asp Arg Gln Gly Arg Phe Asp Arg Ser Val Glu Lys Trp Arg
545                 550                 555                 560

Arg Phe His Tyr Asp Ile Lys Ile Phe Asn Gln Trp Leu Thr Glu Ala

```
                  565                 570                 575
Glu Gln Phe Leu Arg Lys Thr Gln Ile Pro Glu Asn Trp Glu His Ala
                580                 585                 590
Lys Tyr Lys Trp Tyr Leu Lys Glu Leu Gln Asp Gly Ile Gly Gln Arg
                595                 600                 605
Gln Thr Val Val Arg Thr Leu Asn Ala Thr Gly Glu Glu Ile Ile Gln
                610                 615                 620
Gln Ser Ser Lys Thr Asp Ala Ser Ile Leu Gln Glu Lys Leu Gly Ser
625                 630                 635                 640
Leu Asn Leu Arg Trp Gln Glu Val Cys Lys Gln Leu Ser Asp Arg Lys
                645                 650                 655
Lys Arg Leu Glu Glu Gln Glu Leu Pro Pro Glu Glu Arg Ala Gln Asn
                660                 665                 670
Val Thr Arg Leu Leu Arg Lys Gln Ala Glu Glu Val Asn Thr Glu Trp
                675                 680                 685
Glu Lys Leu Asn Leu His Ser Ala Asp Trp Gln Arg Lys Ile Asp Glu
                690                 695                 700
Thr Leu Glu Arg Leu Gln Glu Leu Gln Glu Ala Thr Asp Glu Leu Asp
705                 710                 715                 720
Leu Lys Leu Arg Gln Ala Glu Val Ile Lys Gly Ser Trp Gln Pro Val
                725                 730                 735
Gly Asp Leu Leu Ile Asp Ser Leu Gln Asp His Leu Glu Lys Val Lys
                740                 745                 750
Ala Leu Arg Gly Glu Ile Ala Pro Leu Lys Glu Asn Val Ser His Val
                755                 760                 765
Asn Asp Leu Ala Arg Gln Leu Thr Thr Leu Gly Ile Gln Leu Ser Pro
                770                 775                 780
Tyr Asn Leu Ser Thr Leu Glu Asp Leu Asn Thr Arg Trp Lys Leu Leu
785                 790                 795                 800
Gln Val Ala Val Glu Asp Arg Val Arg Gln Leu His Glu Ala His Arg
                805                 810                 815
Asp Phe Gly Pro Ala Ser Gln His Phe Leu Ser Thr Ser Val Gln Gly
                820                 825                 830
Pro Trp Glu Arg Ala Ile Ser Pro Asn Lys Val Pro Tyr Tyr Ile Asn
                835                 840                 845
His Glu Thr Gln Thr Thr Cys Trp Asp His Pro Lys Met Thr Glu Leu
                850                 855                 860
Tyr Gln Ser Leu Ala Asp Leu Asn Asn Val Arg Phe Ser Ala Tyr Arg
865                 870                 875                 880
Thr Ala Met Lys Leu Arg Arg Leu Gln Lys Ala Leu Cys Leu Asp Leu
                885                 890                 895
Leu Ser Leu Ser Ala Ala Cys Asp Ala Leu Asp Gln His Asn Leu Lys
                900                 905                 910
Gln Asn Asp Gln Pro Met Asp Ile Leu Gln Ile Ile Asn Cys Leu Thr
                915                 920                 925
Thr Ile Tyr Asp Arg Leu Glu Gln Glu His Asn Asn Leu Val Asn Val
                930                 935                 940
Pro Leu Cys Val Asp Met Cys Leu Asn Trp Leu Leu Asn Val Tyr Asp
945                 950                 955                 960
Thr Gly Arg Thr Gly Arg Ile Arg Val Leu Ser Phe Lys Thr Gly Ile
                965                 970                 975
Ile Ser Leu Cys Lys Ala His Leu Glu Asp Lys Tyr Arg Tyr Leu Phe
                980                 985                 990
```

-continued

Lys Gln Val Ala Ser Ser Thr Gly Phe Cys Asp Gln Arg Arg Leu Gly
        995                 1000                1005

Leu Leu Leu His Asp Ser Ile Gln Ile Pro Arg Gln Leu Gly Glu
    1010                1015                1020

Val Ala Ser Phe Gly Gly Ser Asn Ile Glu Pro Ser Val Arg Ser
    1025                1030                1035

Cys Phe Gln Phe Ala Asn Asn Lys Pro Glu Ile Glu Ala Ala Leu
    1040                1045                1050

Phe Leu Asp Trp Met Arg Leu Glu Pro Gln Ser Met Val Trp Leu
    1055                1060                1065

Pro Val Leu His Arg Val Ala Ala Glu Thr Ala Lys His Gln
    1070                1075                1080

Ala Lys Cys Asn Ile Cys Lys Glu Cys Pro Ile Ile Gly Phe Arg
    1085                1090                1095

Tyr Arg Ser Leu Lys His Phe Asn Tyr Asp Ile Cys Gln Ser Cys
    1100                1105                1110

Phe Phe Ser Gly Arg Val Ala Lys Gly His Lys Met His Tyr Pro
    1115                1120                1125

Met Val Glu Tyr Cys Thr Pro Thr Thr Ser Gly Glu Asp Val Arg
    1130                1135                1140

Asp Phe Ala Lys Val Leu Lys Asn Lys Phe Arg Thr Lys Arg Tyr
    1145                1150                1155

Phe Ala Lys His Pro Arg Met Gly Tyr Leu Pro Val Gln Thr Val
    1160                1165                1170

Leu Glu Gly Asp Asn Met Glu Thr Asp Thr Met
    1175                1180

<210> SEQ ID NO 8
<211> LENGTH: 1188
<212> TYPE: PRT
<213> ORGANISM: Artificial Sequence
<220> FEATURE:
<223> OTHER INFORMATION: micro-Dys3

<400> SEQUENCE: 8

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

```
Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575
```

-continued

```
Glu Lys Glu Asp Ala Val Asn Lys Ile His Thr Thr Gly Phe Lys Asp
            580                 585                 590
Gln Asn Glu Met Leu Ser Ser Leu Gln Lys Leu Ala Val Leu Lys Ala
        595                 600                 605
Asp Leu Glu Lys Lys Lys Gln Ser Met Gly Lys Leu Tyr Ser Leu Lys
    610                 615                 620
Gln Asp Leu Leu Ser Thr Leu Lys Asn Lys Ser Val Thr Gln Lys Thr
625                 630                 635                 640
Glu Ala Trp Leu Asp Asn Phe Ala Arg Cys Trp Asp Asn Leu Val Gln
                645                 650                 655
Lys Leu Glu Lys Ser Thr Ala Gln Ile Ser Gln Ala Ala Pro Gly Leu
            660                 665                 670
Thr Thr Ile Gly Ala Ser Pro Thr Gln Thr Val Thr Leu Val Thr Gln
        675                 680                 685
Pro Val Val Thr Lys Glu Thr Ala Ile Ser Lys Leu Glu Met Pro Ser
    690                 695                 700
Ser Leu Met Leu Glu Val Pro Ala Leu Ala Asp Phe Asn Arg Ala Trp
705                 710                 715                 720
Thr Glu Leu Thr Asp Trp Leu Ser Leu Leu Asp Gln Val Ile Lys Ser
                725                 730                 735
Trp Gln Pro Val Gly Asp Leu Leu Ile Asp Ser Leu Gln Asp His Leu
            740                 745                 750
Glu Lys Val Lys Ala Leu Arg Gly Glu Ile Ala Pro Leu Lys Glu Asn
        755                 760                 765
Val Ser His Val Asn Asp Leu Ala Arg Gln Leu Thr Thr Leu Gly Ile
    770                 775                 780
Gln Leu Ser Pro Tyr Asn Leu Ser Thr Leu Glu Asp Leu Asn Thr Arg
785                 790                 795                 800
Trp Lys Leu Leu Gln Val Ala Val Glu Asp Arg Val Arg Gln Leu His
                805                 810                 815
Glu Ala His Arg Asp Phe Gly Pro Ala Ser Gln His Phe Leu Ser Thr
            820                 825                 830
Ser Val Gln Gly Pro Trp Glu Arg Ala Ile Ser Pro Asn Lys Val Pro
        835                 840                 845
Tyr Tyr Ile Asn His Glu Thr Gln Thr Thr Cys Trp Asp His Pro Lys
    850                 855                 860
Met Thr Glu Leu Tyr Gln Ser Leu Ala Asp Leu Asn Asn Val Arg Phe
865                 870                 875                 880
Ser Ala Tyr Arg Thr Ala Met Lys Leu Arg Arg Leu Gln Lys Ala Leu
                885                 890                 895
Cys Leu Asp Leu Leu Ser Leu Ser Ala Ala Cys Asp Ala Leu Asp Gln
            900                 905                 910
His Asn Leu Lys Gln Asn Asp Gln Pro Met Asp Ile Leu Gln Ile Ile
        915                 920                 925
Asn Cys Leu Thr Thr Ile Tyr Asp Arg Leu Glu Gln Glu His Asn Asn
    930                 935                 940
Leu Val Asn Val Pro Leu Cys Val Asp Met Cys Leu Asn Trp Leu Leu
945                 950                 955                 960
Asn Val Tyr Asp Thr Gly Arg Thr Gly Arg Ile Arg Val Leu Ser Phe
                965                 970                 975
Lys Thr Gly Ile Ile Ser Leu Cys Lys Ala His Leu Glu Asp Lys Tyr
            980                 985                 990
Arg Tyr Leu Phe Lys Gln Val Ala  Ser Ser Thr Gly Phe  Cys Asp Gln
```

|  | 995 |  |  |  | 1000 |  |  |  | 1005 |  |
|---|---|---|---|---|---|---|---|---|---|---|
| Arg | Arg | Leu | Gly | Leu | Leu | Leu | His | Asp | Ser | Ile | Gln | Ile | Pro | Arg |
|  | 1010 |  |  |  | 1015 |  |  |  | 1020 |  |

Gln Leu Gly Glu Val Ala Ser Phe Gly Gly Ser Asn Ile Glu Pro
    1025                1030                1035

Ser Val Arg Ser Cys Phe Gln Phe Ala Asn Asn Lys Pro Glu Ile
    1040                1045                1050

Glu Ala Ala Leu Phe Leu Asp Trp Met Arg Leu Glu Pro Gln Ser
    1055                1060                1065

Met Val Trp Leu Pro Val Leu His Arg Val Ala Ala Glu Thr
    1070                1075                1080

Ala Lys His Gln Ala Lys Cys Asn Ile Cys Lys Glu Cys Pro Ile
    1085                1090                1095

Ile Gly Phe Arg Tyr Arg Ser Leu Lys His Phe Asn Tyr Asp Ile
    1100                1105                1110

Cys Gln Ser Cys Phe Phe Ser Gly Arg Val Ala Lys Gly His Lys
    1115                1120                1125

Met His Tyr Pro Met Val Glu Tyr Cys Thr Pro Thr Thr Ser Gly
    1130                1135                1140

Glu Asp Val Arg Asp Phe Ala Lys Val Leu Lys Asn Lys Phe Arg
    1145                1150                1155

Thr Lys Arg Tyr Phe Ala Lys His Pro Arg Met Gly Tyr Leu Pro
    1160                1165                1170

Val Gln Thr Val Leu Glu Gly Asp Asn Met Glu Thr Asp Thr Met
    1175                1180                1185

<210> SEQ ID NO 9
<211> LENGTH: 1231
<212> TYPE: PRT
<213> ORGANISM: Artificial Sequence
<220> FEATURE:
<223> OTHER INFORMATION: micro-Dys4

<400> SEQUENCE: 9

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
                20                  25                  30

Gly Lys Gln His Ile Glu Asn Leu Phe Ser Asp Leu Gln Asp Gly Arg
            35                  40                  45

Arg Leu Leu Asp Leu Leu Glu Gly Leu Thr Gly Gln Lys Leu Pro Lys
        50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His

```
            165                 170                 175
Arg Pro Asp Leu Phe Asp Trp Asn Ser Val Cys Gln Gln Ser Ala
            180                 185                 190

Thr Gln Arg Leu Glu His Ala Phe Asn Ile Ala Arg Tyr Gln Leu Gly
            195                 200                 205

Ile Glu Lys Leu Leu Asp Pro Glu Asp Val Asp Thr Thr Tyr Pro Asp
210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
            245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
            275                 280                 285

Thr Ser Ser Pro Lys Pro Arg Phe Lys Ser Tyr Ala Tyr Thr Gln Ala
            290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
            325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
            355                 360                 365

Ser Asn Asp Val Glu Val Val Lys Asp Gln Phe His Thr His Glu Gly
            370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
            405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
            435                 440                 445

Leu Met Asp Leu Gln Asn Gln Lys Leu Lys Glu Leu Asn Asp Trp Leu
450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
            485                 490                 495

Gln Glu Asp Leu Glu Gln Glu Gln Val Arg Val Asn Ser Leu Thr His
            500                 505                 510

Met Val Val Val Asp Glu Ser Ser Gly Asp His Ala Thr Ala Ala
            515                 520                 525

Leu Glu Glu Gln Leu Lys Val Leu Gly Asp Arg Trp Ala Asn Ile Cys
            530                 535                 540

Arg Trp Thr Glu Asp Arg Trp Val Leu Gln Asp Ile Leu Leu Lys
545                 550                 555                 560

Trp Gln Arg Leu Thr Glu Glu Gln Cys Leu Phe Ser Ala Trp Leu Ser
            565                 570                 575

Glu Lys Glu Asp Ala Val Asn Lys Ile His Thr Thr Gly Phe Lys Asp
            580                 585                 590
```

```
Gln Asn Glu Met Leu Ser Ser Leu Gln Lys Leu Ala Val Leu Lys Ala
            595                 600                 605

Asp Leu Glu Lys Lys Gln Ser Met Gly Lys Leu Tyr Ser Leu Lys
            610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Ala Pro Gly Leu
            660                 665                 670

Thr Thr Ile Gly Ala Ser Pro Thr Gln Thr Val Thr Leu Val Thr Gln
            675                 680                 685

Pro Val Val Thr Lys Glu Thr Ala Ile Ser Lys Leu Glu Met Pro Ser
            690                 695                 700

Ser Leu Met Leu Glu Glu Leu Pro Pro Glu Glu Arg Ala Gln Asn Val
705                 710                 715                 720

Thr Arg Leu Leu Arg Lys Gln Ala Glu Val Asn Thr Glu Trp Glu
                725                 730                 735

Lys Leu Asn Leu His Ser Ala Asp Trp Gln Arg Lys Ile Asp Glu Thr
            740                 745                 750

Leu Glu Arg Leu Gln Glu Leu Gln Glu Ala Thr Asp Glu Leu Asp Leu
            755                 760                 765

Lys Leu Arg Gln Ala Glu Val Ile Lys Gly Ser Trp Gln Pro Val Gly
            770                 775                 780

Asp Leu Leu Ile Asp Ser Leu Gln Asp His Leu Glu Lys Val Lys Ala
785                 790                 795                 800

Leu Arg Gly Glu Ile Ala Pro Leu Lys Glu Asn Val Ser His Val Asn
                805                 810                 815

Asp Leu Ala Arg Gln Leu Thr Thr Leu Gly Ile Gln Leu Ser Pro Tyr
            820                 825                 830

Asn Leu Ser Thr Leu Glu Asp Leu Asn Thr Arg Trp Lys Leu Leu Gln
            835                 840                 845

Val Ala Val Glu Asp Arg Val Arg Gln Leu His Glu Ala His Arg Asp
            850                 855                 860

Phe Gly Pro Ala Ser Gln His Phe Leu Ser Thr Ser Val Gln Gly Pro
865                 870                 875                 880

Trp Glu Arg Ala Ile Ser Pro Asn Lys Val Pro Tyr Tyr Ile Asn His
                885                 890                 895

Glu Thr Gln Thr Thr Cys Trp Asp His Pro Lys Met Thr Glu Leu Tyr
            900                 905                 910

Gln Ser Leu Ala Asp Leu Asn Asn Val Arg Phe Ser Ala Tyr Arg Thr
            915                 920                 925

Ala Met Lys Leu Arg Arg Leu Gln Lys Ala Leu Cys Leu Asp Leu Leu
            930                 935                 940

Ser Leu Ser Ala Ala Cys Asp Ala Leu Asp Gln His Asn Leu Lys Gln
945                 950                 955                 960

Asn Asp Gln Pro Met Asp Ile Leu Gln Ile Ile Asn Cys Leu Thr Thr
                965                 970                 975

Ile Tyr Asp Arg Leu Glu Gln Glu His Asn Asn Leu Val Asn Val Pro
            980                 985                 990

Leu Cys Val Asp Met Cys Leu Asn  Trp Leu Leu Asn Val  Tyr Asp Thr
            995                 1000                1005
```

```
Gly Arg Thr Gly Arg Ile Arg Val Leu Ser Phe Lys Thr Gly Ile
    1010                1015                1020

Ile Ser Leu Cys Lys Ala His Leu Glu Asp Lys Tyr Arg Tyr Leu
    1025                1030                1035

Phe Lys Gln Val Ala Ser Ser Thr Gly Phe Cys Asp Gln Arg Arg
    1040                1045                1050

Leu Gly Leu Leu Leu His Asp Ser Ile Gln Ile Pro Arg Gln Leu
    1055                1060                1065

Gly Glu Val Ala Ser Phe Gly Gly Ser Asn Ile Glu Pro Ser Val
    1070                1075                1080

Arg Ser Cys Phe Gln Phe Ala Asn Asn Lys Pro Glu Ile Glu Ala
    1085                1090                1095

Ala Leu Phe Leu Asp Trp Met Arg Leu Glu Pro Gln Ser Met Val
    1100                1105                1110

Trp Leu Pro Val Leu His Arg Val Ala Ala Glu Thr Ala Lys
    1115                1120                1125

His Gln Ala Lys Cys Asn Ile Cys Lys Glu Cys Pro Ile Ile Gly
    1130                1135                1140

Phe Arg Tyr Arg Ser Leu Lys His Phe Asn Tyr Asp Ile Cys Gln
    1145                1150                1155

Ser Cys Phe Phe Ser Gly Arg Val Ala Lys Gly His Lys Met His
    1160                1165                1170

Tyr Pro Met Val Glu Tyr Cys Thr Pro Thr Thr Ser Gly Glu Asp
    1175                1180                1185

Val Arg Asp Phe Ala Lys Val Leu Lys Asn Lys Phe Arg Thr Lys
    1190                1195                1200

Arg Tyr Phe Ala Lys His Pro Arg Met Gly Tyr Leu Pro Val Gln
    1205                1210                1215

Thr Val Leu Glu Gly Asp Asn Met Glu Thr Asp Thr Met
    1220                1225                1230

<210> SEQ ID NO 10
<211> LENGTH: 1383
<212> TYPE: PRT
<213> ORGANISM: Artificial Sequence
<220> FEATURE:
<223> OTHER INFORMATION: micro-Dys6

<400> SEQUENCE: 10

Met Leu Trp Trp Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
                20                  25                  30

Gly Lys Gln His Ile Glu Asn Leu Phe Ser Asp Leu Gln Asp Gly Arg
            35                  40                  45

Arg Leu Leu Asp Leu Leu Glu Gly Leu Thr Gly Gln Lys Leu Pro Lys
    50                  55                      60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125
```

```
Ala Gly Leu Gln Gln Thr Asn Ser Glu Lys Ile Leu Leu Ser Trp Val
    130                 135                 140
Arg Gln Ser Thr Arg Asn Tyr Pro Gln Val Asn Val Ile Asn Phe Thr
145                 150                 155                 160
Thr Ser Trp Ser Asp Gly Leu Ala Leu Asn Ala Leu Ile His Ser His
                165                 170                 175
Arg Pro Asp Leu Phe Asp Trp Asn Ser Val Val Cys Gln Gln Ser Ala
            180                 185                 190
Thr Gln Arg Leu Glu His Ala Phe Asn Ile Ala Arg Tyr Gln Leu Gly
        195                 200                 205
Ile Glu Lys Leu Leu Asp Pro Glu Asp Val Asp Thr Thr Tyr Pro Asp
210                 215                 220
Lys Lys Ser Ile Leu Met Tyr Ile Thr Ser Leu Phe Gln Val Leu Pro
225                 230                 235                 240
Gln Gln Val Ser Ile Glu Ala Ile Gln Glu Val Met Leu Pro Arg
                245                 250                 255
Pro Pro Lys Val Thr Lys Glu Glu His Phe Gln Leu His His Gln Met
            260                 265                 270
His Tyr Ser Gln Gln Ile Thr Val Ser Leu Ala Gln Gly Tyr Glu Arg
        275                 280                 285
Thr Ser Ser Pro Lys Pro Arg Phe Lys Ser Tyr Ala Tyr Thr Gln Ala
    290                 295                 300
Ala Tyr Val Thr Thr Ser Asp Pro Thr Arg Ser Pro Phe Pro Ser Gln
305                 310                 315                 320
His Leu Glu Ala Pro Glu Asp Lys Ser Phe Gly Ser Ser Leu Met Glu
                325                 330                 335
Ser Glu Val Asn Leu Asp Arg Tyr Gln Thr Ala Leu Glu Glu Val Leu
            340                 345                 350
Ser Trp Leu Leu Ser Ala Glu Asp Thr Leu Gln Ala Gln Gly Glu Ile
        355                 360                 365
Ser Asn Asp Val Glu Val Val Lys Asp Gln Phe His Thr His Glu Gly
    370                 375                 380
Tyr Met Met Asp Leu Thr Ala His Gln Gly Arg Val Gly Asn Ile Leu
385                 390                 395                 400
Gln Leu Gly Ser Lys Leu Ile Gly Thr Gly Lys Leu Ser Glu Asp Glu
                405                 410                 415
Glu Thr Glu Val Gln Glu Gln Met Asn Leu Leu Asn Ser Arg Trp Glu
            420                 425                 430
Cys Leu Arg Val Ala Ser Met Glu Lys Gln Ser Asn Leu His Arg Val
        435                 440                 445
Leu Met Asp Leu Gln Asn Gln Lys Leu Lys Glu Leu Asn Asp Trp Leu
    450                 455                 460
Thr Lys Thr Glu Glu Arg Thr Arg Lys Met Glu Glu Glu Pro Leu Gly
465                 470                 475                 480
Pro Asp Leu Glu Asp Leu Lys Arg Gln Val Gln Gln His Lys Val Leu
                485                 490                 495
Gln Glu Asp Leu Glu Gln Glu Gln Val Arg Val Asn Ser Leu Thr His
            500                 505                 510
Met Val Val Val Asp Glu Ser Ser Gly Asp His Ala Thr Ala Ala
        515                 520                 525
Leu Glu Glu Gln Leu Lys Val Leu Gly Asp Arg Trp Ala Asn Ile Cys
    530                 535                 540
Arg Trp Thr Glu Asp Arg Trp Val Leu Leu Gln Asp Ile Leu Leu Lys
```

-continued

```
545                 550                 555                 560
Trp Gln Arg Leu Thr Glu Glu Gln Cys Leu Phe Ser Ala Trp Leu Ser
                565                 570                 575
Glu Lys Glu Asp Ala Val Asn Lys Ile His Thr Thr Gly Phe Lys Asp
                580                 585                 590
Gln Asn Glu Met Leu Ser Ser Leu Gln Lys Leu Ala Val Leu Lys Ala
                595                 600                 605
Asp Leu Glu Lys Lys Gln Ser Met Gly Lys Leu Tyr Ser Leu Lys
610                 615                 620
Gln Asp Leu Leu Ser Thr Leu Lys Asn Lys Ser Val Thr Gln Lys Thr
625                 630                 635                 640
Glu Ala Trp Leu Asp Asn Phe Ala Arg Cys Trp Asp Asn Leu Val Gln
                645                 650                 655
Lys Leu Glu Lys Ser Thr Ala Gln Ile Ser Gln Ala Ile His Thr Val
                660                 665                 670
Arg Glu Glu Thr Met Met Val Met Thr Glu Asp Met Pro Leu Glu Ile
                675                 680                 685
Ser Tyr Val Pro Ser Thr Tyr Leu Thr Glu Ile Thr His Val Ser Gln
                690                 695                 700
Ala Leu Leu Glu Val Glu Gln Leu Leu Asn Ala Pro Asp Leu Cys Ala
705                 710                 715                 720
Lys Asp Phe Glu Asp Leu Phe Lys Gln Glu Ser Leu Lys Asn Ile
                725                 730                 735
Lys Asp Ser Leu Gln Gln Ser Ser Gly Arg Ile Asp Ile Ile His Ser
                740                 745                 750
Lys Lys Thr Ala Ala Leu Gln Ser Ala Thr Pro Val Glu Arg Val Lys
                755                 760                 765
Leu Gln Glu Ala Leu Ser Gln Leu Asp Phe Gln Trp Glu Lys Val Asn
                770                 775                 780
Lys Met Tyr Lys Asp Arg Gln Gly Arg Phe Asp Arg Ser Val Glu Lys
785                 790                 795                 800
Trp Arg Arg Phe His Tyr Asp Ile Lys Ile Phe Asn Gln Trp Leu Thr
                805                 810                 815
Glu Ala Glu Gln Phe Leu Arg Lys Thr Gln Ile Pro Glu Asn Trp Glu
                820                 825                 830
His Ala Lys Tyr Lys Trp Tyr Leu Lys Glu Leu Gln Asp Gly Ile Gly
                835                 840                 845
Gln Arg Gln Thr Val Val Arg Thr Leu Asn Ala Thr Gly Glu Glu Ile
850                 855                 860
Ile Gln Gln Ser Ser Lys Thr Asp Ala Ser Ile Leu Gln Glu Lys Leu
865                 870                 875                 880
Gly Ser Leu Asn Leu Arg Trp Gln Glu Val Cys Lys Gln Leu Ser Asp
                885                 890                 895
Arg Lys Lys Arg Leu Glu Glu Gln Leu Glu Arg Leu Gln Glu Leu Gln
                900                 905                 910
Glu Ala Thr Asp Glu Leu Asp Leu Lys Leu Arg Gln Ala Glu Val Ile
                915                 920                 925
Lys Gly Ser Trp Gln Pro Val Gly Asp Leu Leu Ile Asp Ser Leu Gln
                930                 935                 940
Asp His Leu Glu Lys Val Lys Ala Leu Arg Gly Glu Ile Ala Pro Leu
945                 950                 955                 960
Lys Glu Asn Val Ser His Val Asn Asp Leu Ala Arg Gln Leu Thr Thr
                965                 970                 975
```

```
Leu Gly Ile Gln Leu Ser Pro Tyr Asn Leu Ser Thr Leu Glu Asp Leu
            980             985             990

Asn Thr Arg Trp Lys Leu Leu Gln Val Ala Val Glu Asp Arg Val Arg
        995             1000            1005

Gln Leu His Glu Ala His Arg Asp Phe Gly Pro Ala Ser Gln His
    1010            1015            1020

Phe Leu Ser Thr Ser Val Gln Gly Pro Trp Glu Arg Ala Ile Ser
    1025            1030            1035

Pro Asn Lys Val Pro Tyr Tyr Ile Asn His Glu Thr Gln Thr Thr
    1040            1045            1050

Cys Trp Asp His Pro Lys Met Thr Glu Leu Tyr Gln Ser Leu Ala
    1055            1060            1065

Asp Leu Asn Asn Val Arg Phe Ser Ala Tyr Arg Thr Ala Met Lys
    1070            1075            1080

Leu Arg Arg Leu Gln Lys Ala Leu Cys Leu Asp Leu Leu Ser Leu
    1085            1090            1095

Ser Ala Ala Cys Asp Ala Leu Asp Gln His Asn Leu Lys Gln Asn
    1100            1105            1110

Asp Gln Pro Met Asp Ile Leu Gln Ile Ile Asn Cys Leu Thr Thr
    1115            1120            1125

Ile Tyr Asp Arg Leu Glu Gln Glu His Asn Asn Leu Val Asn Val
    1130            1135            1140

Pro Leu Cys Val Asp Met Cys Leu Asn Trp Leu Leu Asn Val Tyr
    1145            1150            1155

Asp Thr Gly Arg Thr Gly Arg Ile Arg Val Leu Ser Phe Lys Thr
    1160            1165            1170

Gly Ile Ile Ser Leu Cys Lys Ala His Leu Glu Asp Lys Tyr Arg
    1175            1180            1185

Tyr Leu Phe Lys Gln Val Ala Ser Ser Thr Gly Phe Cys Asp Gln
    1190            1195            1200

Arg Arg Leu Gly Leu Leu Leu His Asp Ser Ile Gln Ile Pro Arg
    1205            1210            1215

Gln Leu Gly Glu Val Ala Ser Phe Gly Gly Ser Asn Ile Glu Pro
    1220            1225            1230

Ser Val Arg Ser Cys Phe Gln Phe Ala Asn Asn Lys Pro Glu Ile
    1235            1240            1245

Glu Ala Ala Leu Phe Leu Asp Trp Met Arg Leu Glu Pro Gln Ser
    1250            1255            1260

Met Val Trp Leu Pro Val Leu His Arg Val Ala Ala Glu Thr
    1265            1270            1275

Ala Lys His Gln Ala Lys Cys Asn Ile Cys Lys Glu Cys Pro Ile
    1280            1285            1290

Ile Gly Phe Arg Tyr Arg Ser Leu Lys His Phe Asn Tyr Asp Ile
    1295            1300            1305

Cys Gln Ser Cys Phe Phe Ser Gly Arg Val Ala Lys Gly His Lys
    1310            1315            1320

Met His Tyr Pro Met Val Glu Tyr Cys Thr Pro Thr Thr Ser Gly
    1325            1330            1335

Glu Asp Val Arg Asp Phe Ala Lys Val Leu Lys Asn Lys Phe Arg
    1340            1345            1350

Thr Lys Arg Tyr Phe Ala Lys His Pro Arg Met Gly Tyr Leu Pro
    1355            1360            1365
```

```
            Val Gln  Thr Val Leu Glu Gly  Asp Asn Met Glu Thr  Asp Thr Met
                1370             1375              1380
```

<210> SEQ ID NO 11
<211> LENGTH: 3564
<212> TYPE: DNA
<213> ORGANISM: Artificial Sequence
<220> FEATURE:
<223> OTHER INFORMATION: micro-DysH3

<400> SEQUENCE: 11

| | | | | | | |
|---|---|---|---|---|---|---|
| atgctttggt | gggaagaagt | agaggactgt | tatgaaagag | aagatgttca | aaagaaaaca | 60 |
| ttcacaaaat | gggtaaatgc | acaatttttct | aagtttggga | agcagcatat | tgagaacctc | 120 |
| ttcagtgacc | tacaggatgg | gaggcgcctc | ctagacctcc | tcgaaggcct | gacagggcaa | 180 |
| aaactgccaa | agaaaaagg | atccacaaga | gttcatgccc | tgaacaatgt | caacaaggca | 240 |
| ctgcgggttt | tgcagaacaa | taatgttgat | ttagtgaata | ttggaagtac | tgacatcgta | 300 |
| gatggaaatc | ataaactgac | tcttggtttg | atttggaata | taatcctcca | ctggcaggtc | 360 |
| aaaaatgtaa | tgaaaatat | catggctgga | ttgcaacaaa | ccaacagtga | aaagattctc | 420 |
| ctgagctggg | tccgacaatc | aactcgtaat | tatccacagg | ttaatgtaat | caacttcacc | 480 |
| accagctggt | ctgatggcct | ggctttgaat | gctctcatcc | atagtcatag | gccagaccta | 540 |
| tttgactgga | atagtgtggt | ttgccagcag | tcagccacac | aacgactgga | acatgcattc | 600 |
| aacatcgcca | gatatcaatt | aggcatagag | aaactactcg | atcctgaaga | tgttgatacc | 660 |
| acctatccag | ataagaagtc | catcttaatg | tacatcacat | cactcttcca | agttttgcct | 720 |
| caacaagtga | gcattgaagc | catccaggaa | gtggaaatgt | tgccaaggcc | acctaaagtg | 780 |
| actaagaag | aacatttca | gttacatcat | caaatgcact | attctcaaca | gatcacggtc | 840 |
| agtctagcac | agggatatga | gagaacttct | tcccctaagc | ctcgattcaa | gagctatgcc | 900 |
| tacacacagg | ctgcttatgt | caccacctct | gaccctacac | ggagcccatt | tccttcacag | 960 |
| catttggaag | ctcctgaaga | caagtcattt | ggcagttcat | tgatggagag | tgaagtaaac | 1020 |
| ctggaccgtt | atcaaacagc | tttagaagaa | gtattatcgt | ggcttctttc | tgctgaggac | 1080 |
| acattgcaag | cacaaggaga | gatttctaat | gatgtggaag | tggtgaaaga | ccagtttcat | 1140 |
| actcatgagg | ggtacatgat | ggatttgaca | gcccatcagg | gccgggttgg | taatattcta | 1200 |
| caattgggaa | gtaagctgat | tggaacagga | aaattatcag | aagatgaaga | aactgaagta | 1260 |
| caagagcaga | tgaatctcct | aaattcaaga | tgggaatgcc | tcagggtagc | tagcatggaa | 1320 |
| aaacaaagca | atttacatag | agttttaatg | gatctccaga | atcagaaact | gaaagagttg | 1380 |
| aatgactggc | taacaaaaac | agaagaaaga | acaaggaaaa | tggaggaaga | gcctcttgga | 1440 |
| cctgatcttg | aagacctaaa | acgccaagta | caacaacata | aggtgcttca | agaagatcta | 1500 |
| gaacaagaac | aagtcagggt | caattctctc | actcacatgg | tggtggtagt | tgatgaatct | 1560 |
| agtggagatc | acgcaactgc | tgctttggaa | gaacaactta | aggtattggg | agatcgatgg | 1620 |
| gcaaacatct | gtagatggac | agaagaccgc | tgggttcttt | tacaagacat | ccttctcaaa | 1680 |
| tggcaacgtc | ttactgaaga | acagtgcctt | tttagtgcat | ggcttcaga | aaaagaagat | 1740 |
| gcagtgaaca | agattcacac | aactggcttt | aaagatcaaa | atgaaatgtt | atcaagtctt | 1800 |
| caaaaactgg | ccgttttaaa | agcggatcta | gaaaagaaaa | agcaatccat | gggcaaactg | 1860 |
| tattcactca | aacaagatct | tctttcaaca | ctgaagaata | agtcagtgac | ccagaagacg | 1920 |
| gaagcatggc | tggataactt | tgcccggtgt | tgggataatt | tagtccaaaa | acttgaaaag | 1980 |

| | |
|---|---|
| agtacagcac agatttcaca ggctgctcct ggactgacca ctattggagc ctctcctact | 2040 |
| cagactgtta ctctggtgac acaacctgtg gttactaagg aaactgccat ctccaaacta | 2100 |
| gaaatgccat cttccttgat gttggagctt gaaagactcc aggaacttca agaggccacg | 2160 |
| gatgagctgg acctcaagct cgcgccaagct gaggtgatca agggatcctg gcagcccgtg | 2220 |
| ggcgatctcc tcattgactc tctccaagat cacctcgaga aagtcaaggc acttcgagga | 2280 |
| gaaattgcgc ctctgaaaga gaacgtgagc cacgtcaatg accttgctcg ccagcttacc | 2340 |
| actttgggca ttcagctctc accgtataac ctcagcactc tggaagacct gaacaccaga | 2400 |
| tggaagcttc tgcaggtggc cgtcgaggac cgagtcaggc agctgcatga agcccacagg | 2460 |
| gactttggtc cagcatctca gcactttctt tccacgtctg tccagggtcc ctgggagaga | 2520 |
| gccatctcgc caaacaaagt gccctactat atcaaccacg agactcaaac aacttgctgg | 2580 |
| gaccatccca aaatgacaga gctctaccag tctttagctg acctgaataa tgtcagattc | 2640 |
| tcagcttata ggactgccat gaaactccga agactgcaga aggcccttg cttggatctc | 2700 |
| ttgagcctgt cagctgcatg tgatgccttg accagcaca acctcaagca aaatgaccag | 2760 |
| cccatggata tcctgcagat tattaattgt ttgaccacta tttatgaccg cctggagcaa | 2820 |
| gagcacaaca atttggtcaa cgtccctctc tgcgtggata tgtgtctgaa ctggctgctg | 2880 |
| aatgtttatg atacgggacg aacagggagg atccgtgtcc tgtcttttaa aactggcatc | 2940 |
| atttccctgt gtaaagcaca tttggaagac aagtacagat accttttcaa gcaagtggca | 3000 |
| agttcaacag gattttgtga ccagcgcagg ctgggcctcc ttctgcatga ttctatccaa | 3060 |
| attccaagac agttgggtga agttgcatcc tttgggggca gtaacattga gccaagtgtc | 3120 |
| cggagctgct tccaatttgc taataataag ccagagatcg aagcggccct cttcctagac | 3180 |
| tggatgagac tggaaccca gtccatggtg tggctgcccg tcctgcacag agtggctgct | 3240 |
| gcagaaactg ccaagcatca ggccaaatgt aacatctgca aagagtgtcc aatcattgga | 3300 |
| ttcaggtaca ggagtctaaa gcactttaat tatgacatct gccaaagctg cttttttct | 3360 |
| ggtcgagttg caaaaggcca taaaatgcac tatcccatgg tggaatattg cactccgact | 3420 |
| acatcaggag aagatgttcg agactttgcc aaggtactaa aaaacaaatt tcgaaccaaa | 3480 |
| aggtattttg cgaagcatcc ccgaatgggc tacctgccag tgcagactgt cttagagggg | 3540 |
| gacaacatgg aaactgacac aatg | 3564 |

<210> SEQ ID NO 12
<211> LENGTH: 3570
<212> TYPE: DNA
<213> ORGANISM: Artificial Sequence
<220> FEATURE:
<223> OTHER INFORMATION: micro-Dys1

<400> SEQUENCE: 12

| | |
|---|---|
| atgctttggt gggaagaagt agaggactgt tatgaaagag aagatgttca aaagaaaaca | 60 |
| ttcacaaaat gggtaaatgc acaatttcct aagtttggga agcagcatat tgagaacctc | 120 |
| ttcagtgacc tacaggatgg gaggcgcctc ctagacctcc tcgaaggcct gacagggcaa | 180 |
| aaactgccaa agaaaaagg atccacaaga gttcatgccc tgaacaatgt caacaaggca | 240 |
| ctgcgggttt tgcagaacaa taatgttgat ttagtgaata ttggaagtac tgacatcgta | 300 |
| gatggaaatc ataaactgac tcttggtttg atttggaata taatcctcca ctggcaggtc | 360 |
| aaaaatgtaa tgaaaatat catggctgga ttgcaacaaa ccaacagtga aaagattctc | 420 |
| ctgagctggg tccgacaatc aactcgtaat tatccacagg ttaatgtaat caacttcacc | 480 |

```
accagctggt ctgatggcct ggctttgaat gctctcatcc atagtcatag gccagaccta    540
tttgactgga atagtgtggt ttgccagcag tcagccacac aacgactgga acatgcattc    600
aacatcgcca gatatcaatt aggcatagaa aaactactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaaggcc acctaaagtg    780 actaagaag aacattttca gttacatcat caaatgcact attctcaaca gatcacggtc     840
agtctagcac agggatatga gagaacttct tcccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
aaacaaagca atttacatag agttttaatg gatctccaga atcagaaact gaaagagttg   1380
aatgactggc taacaaaaac agaagaaaga acaaggaaaa tggaggaaga gcctcttgga   1440
cctgatcttg aagacctaaa acgccaagta caacaacata aggtgcttca agaagatcta   1500
gaacaagaac aagtcagggt caattctctc actcacatgg tggtggtagt tgatgaatct   1560
agtggagatc acgcaactgc tgctttggaa gaacaactta aggtattggg agatcgatgg   1620
gcaaacatct gtagatggac agaagaccgc tgggttcttt tacaagacat ccttctcaaa   1680
tggcaacgtc ttactgaaga acagtgcctt tttagtgcat ggctttcaga aaagaagat    1740 gcagtgaaca agattcacac aactggcttt aaggatcaaa atgaaatgtt atcaagtctt   1800
caaaaactgg ccgtttttaaa agcggatcta gaaaagaaaa agcaatccat gggcaaactg   1860
tattcactca aacaagatct tctttcaaca ctgaagaata agtcagtgac ccagaagacg   1920
gaagcatggc tggataactt tgcccggtgt tgggataatt tagtccaaaa acttgaaaag   1980
agtacagcac agatttcaca ggctgagctg cctcctgagg agagagccca gaatgtcact   2040
cggcttctac gaaagcaggc tgaggaggtc aatactgagt gggaaaaatt gaacctgcac   2100
tccgctgact ggcagagaaa aatagatgag acccttgaaa gactccagga acttcaagag   2160
gccacggatg agctggacct caagctgcgc caagctgagg tgatcaaggg atcctggcag   2220
cccgtgggcg atctcctcat tgactctctc caagatcacc tcgagaaagt caaggcactt   2280
cgaggagaaa ttgcgcctct gaaagagaac gtgagccacg tcaatgacct tgctcgccag   2340
cttaccactt tgggcattca gctctcaccg tataacctca gcactctgga agacctgaac   2400
accagatgga gcttctgca ggtggccgtc gaggaccgag tcaggcagct gcatgaagcc   2460
cacagggact ttggtccagc atctcagcac tttctttcca cgtctgtcca gggtccctgg   2520
gagagagcca tctcgccaaa caaagtgccc tactatatca accacgagac tcaaacaact   2580
tgctgggacc atcccaaaat gacagagctc taccagtctt tagctgacct gaataatgtc   2640
agattctcag cttataggac tgccatgaaa ctccgaagac tgcagaaggc cctttgcttg   2700
gatctcttga gcctgtcagc tgcatgtgat gccttggacc agcacaacct caagcaaaat   2760
gaccagccca tggatatcct gcagattatt aattgtttga ccactatttta tgaccgcctg   2820
```

```
gagcaagagc acaacaattt ggtcaacgtc cctctctgcg tggatatgtg tctgaactgg    2880
ctgctgaatg tttatgatac gggacgaaca gggaggatcc gtgtcctgtc ttttaaaact    2940
ggcatcattt ccctgtgtaa agcacatttg aagacaagt acagatacct tttcaagcaa     3000
gtggcaagtt caacaggatt ttgtgaccag cgcaggctgg gcctccttct gcatgattct    3060
atccaaattc caagacagtt gggtgaagtt gcatcctttg ggggcagtaa cattgagcca    3120
agtgtccgga gctgcttcca atttgctaat aataagccag agatcgaagc ggccctcttc    3180
ctagactgga tgagactgga accccagtcc atggtgtggc tgcccgtcct gcacagagtg    3240
gctgctgcag aaactgccaa gcatcaggcc aaatgtaaca tctgcaaaga gtgtccaatc    3300
attggattca ggtacaggag tctaaagcac tttaattatg acatctgcca aagctgcttt    3360
ttttctggtc gagttgcaaa aggccataaa atgcactatc ccatggtgga atattgcact    3420
ccgactacat caggagaaga tgttcgagac tttgccaagg tactaaaaaa caaatttcga    3480
accaaaaggt attttgcgaa gcatcccga atgggctacc tgccagtgca gactgtctta    3540
gagggggaca acatggaaac tgacacaatg                                     3570
```

<210> SEQ ID NO 13  
<211> LENGTH: 3552  
<212> TYPE: DNA  
<213> ORGANISM: Artificial Sequence  
<220> FEATURE:  
<223> OTHER INFORMATION: micro-Dys2

<400> SEQUENCE: 13

```
atgctttggt gggaagaagt agaggactgt tatgaaagag aagatgttca aaagaaaaca     60
ttcacaaaat gggtaaatgc acaattttct aagtttggga agcagcatat tgagaacctc    120
ttcagtgacc tacaggatgg gaggcgcctc ctagacctcc tcgaaggcct gacagggcaa    180
aaactgccaa agaaaaagg atccacaaga gttcatgccc tgaacaatgt caacaaggca    240
ctgcgggttt tgcagaacaa taatgttgat ttagtgaata ttggaagtac tgacatcgta    300
gatggaaatc ataaactgac tcttggtttg atttggaata taatcctcca ctggcaggtc    360
aaaaatgtaa tgaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggctttgaat gctctcatcc atagtcatag gccagaccta    540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaaggcc acctaaagtg    780
actaaagaag aacattttca gttacatcat caaatgcact attctcaaca gatcacggtc    840
agtctagcac agggatatga gagaacttct tcccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac    1020
ctggaccgtt atcaaacagc tttagaagaa gtattatcgt ggcttcttc tgctgaggac    1080 acattgcaag cacaaggaga gatttctaat gatgtggaag tggtgaaaga ccagtttcat    1140
actcatgagg ggtacatgat ggatttgaca gcccatcagg gccgggttgg taatattcta    1200
caattgggaa gtaagctgat tggaacagga aaattatcag aagatgaaga aactgaagta    1260
caagagcaga tgaatctcct aaattcaaga tgggaatgcc tcagggtagc tagcatggaa    1320
```

-continued

```
aaacaaagca atttacattc ttatgtgcct tctacttatt tgactgaaat cactcatgtc    1380
tcacaagccc tattagaagt ggaacaactt ctcaatgctc ctgacctctg tgctaaggac    1440
tttgaagatc tctttaagca agaggagtct ctgaagaata taaaagatag tctacaacaa    1500
agctcaggtc ggattgacat tattcatagc aagaagacag cagcattgca aagtgcaacg    1560
cctgtggaaa gggtgaagct acaggaagct ctctcccagc ttgatttcca atgggaaaaa    1620
gttaacaaaa tgtacaagga ccgacaaggg cgatttgaca gatctgttga gaaatggcgg    1680
cgttttcatt atgatataaa gatatttaat cagtggctaa cagaagctga acagtttctc    1740
agaaagacac aaattcctga gaattgggaa catgctaaat acaaatggta tcttaaggaa    1800
ctccaggatg gcattgggca gcggcaaact gttgtcagaa cattgaatgc aactggggaa    1860
gaaataattc agcaatcctc aaaaacagat gccagtattc tacaggaaaa attgggaagc    1920
ctgaatctgc ggtggcagga ggtctgcaaa cagctgtcag acagaaaaaa gaggctagaa    1980
gaacaagagc tgcctcctga ggagagagcc cagaatgtca ctcggcttct acgaaagcag    2040
gctgaggagg tcaatactga gtgggaaaaa ttgaacctgc actccgctga ctggcagaga    2100
aaaatagatg agacccttga aagactccag gaacttcaag aggccacgga tgagctggac    2160
ctcaagctgc gccaagctga ggtgatcaag ggatcctggc agcccgtggg cgatctcctc    2220
attgactctc tccaagatca cctcgagaaa gtcaaggcac ttcgaggaga aattgcgcct    2280
ctgaaagaga acgtgagcca cgtcaatgac cttgctcgcc agcttaccac tttgggcatt    2340
cagctctcac cgtataacct cagcactctg gaagacctga acaccagatg gaagcttctg    2400
caggtggccg tcgaggaccg agtcaggcag ctgcatgaag cccacaggga ctttggtcca    2460
gcatctcagc actttctttc cacgtctgtc cagggtccct gggagagagc catctcgcca    2520
aacaaagtgc cctactatat caaccacgag actcaaacaa cttgctggga ccatcccaaa    2580
atgacagagc tctaccagtc tttagctgac ctgaataatg tcagattctc agcttatagg    2640
actgccatga aactccgaag actgcagaag gcccttttgct tggatctctt gagcctgtca    2700
gctgcatgtg atgccttgga ccagcacaac ctcaagcaaa atgaccagcc catggatatc    2760
ctgcagatta ttaattgttt gaccactatt tatgaccgcc tggagcaaga gcacaacaat    2820
ttggtcaacg tccctctctg cgtggatatg tgtctgaact ggctgctgaa tgtttatgat    2880
acgggacgaa cagggaggat ccgtgtcctg tcttttaaaa ctggcatcat ttccctgtgt    2940
aaagcacatt tggaagacaa gtacagatac cttttcaagc aagtggcaag ttcaacagga    3000
ttttgtgacc agcgcaggct gggcctcctt ctgcatgatt ctatccaaat tccaagacag    3060
ttgggtgaag ttgcatcctt tggggggcagt aacattgagc caagtgtccg gagctgcttc    3120
caatttgcta ataataagcc agagatcgaa gcggccctct tcctagactg gatgagactg    3180
gaaccccagt ccatggtgtg gctgcccgtc ctgcacagag tggctgctgc agaaactgcc    3240
aagcatcagg ccaaatgtaa catctgcaaa gagtgtccaa tcattggatt caggtacagg    3300
agtctaaagc actttaatta tgacatctgc caaagctgct tttttttctgg tcgagttgca    3360 aaaggccata aaatgcacta tcccatggtg gaatattgca ctccgactac atcaggagaa    3420
gatgttcgag actttgccaa ggtactaaaa acaaatttc gaaccaaaag gtattttgcg    3480
aagcatcccc gaatgggcta cctgccagtg cagactgtct tagaggggga caacatggaa    3540
actgacacaa tg                                                        3552
```

<210> SEQ ID NO 14

<211> LENGTH: 3564
<212> TYPE: DNA
<213> ORGANISM: Artificial Sequence
<220> FEATURE:
<223> OTHER INFORMATION: micro-Dys3

<400> SEQUENCE: 14

| | | | | | |
|---|---|---|---|---|---|
| atgctttggt | gggaagaagt | agaggactgt | tatgaaagag | aagatgttca | aaagaaaaca | 60 |
| ttcacaaaat | gggtaaatgc | acaatttct | aagtttggga | agcagcatat | tgagaacctc | 120 |
| ttcagtgacc | tacaggatgg | gaggcgcctc | ctagacctcc | tcgaaggcct | gacagggcaa | 180 |
| aaactgccaa | agaaaaagg | atccacaaga | gttcatgccc | tgaacaatgt | caacaaggca | 240 |
| ctgcgggttt | tgcagaacaa | taatgttgat | ttagtgaata | ttggaagtac | tgacatcgta | 300 |
| gatggaaatc | ataaactgac | tcttggtttg | atttggaata | taatcctcca | ctggcaggtc | 360 |
| aaaaatgtaa | tgaaaatat | catggctgga | ttgcaacaaa | ccaacagtga | aaagattctc | 420 |
| ctgagctggg | tccgacaatc | aactcgtaat | tatccacagg | ttaatgtaat | caacttcacc | 480 |
| accagctggt | ctgatggcct | ggctttgaat | gctctcatcc | atagtcatag | gccagaccta | 540 |
| tttgactgga | atagtgtggt | ttgccagcag | tcagccacac | aacgactgga | acatgcattc | 600 |
| aacatcgcca | gatatcaatt | aggcatagag | aaactactcg | atcctgaaga | tgttgatacc | 660 |
| acctatccag | ataagaagtc | catcttaatg | tacatcacat | cactcttcca | agttttgcct | 720 |
| caacaagtga | gcattgaagc | catccaggaa | gtggaaatgt | tgccaaggcc | acctaaagtg | 780 |
| actaagaag | aacattttca | gttacatcat | caaatgcact | attctcaaca | gatcacggtc | 840 |
| agtctagcac | agggatatga | gagaacttct | tcccctaagc | ctcgattcaa | gagctatgcc | 900 |
| tacacacagg | ctgcttatgt | caccacctct | gaccctacac | ggagcccatt | tccttcacag | 960 |
| catttggaag | ctcctgaaga | caagtcattt | ggcagttcat | tgatggagag | tgaagtaaac | 1020 |
| ctggaccgtt | atcaaacagc | tttagaagaa | gtattatcgt | ggcttcttc | tgctgaggac | 1080 |
| acattgcaag | cacaaggaga | gatttctaat | gatgtggaag | tggtgaaaga | ccagtttcat | 1140 |
| actcatgagg | ggtacatgat | ggatttgaca | gcccatcagg | gccgggttgg | taatattcta | 1200 |
| caattgggaa | gtaagctgat | tggaacagga | aaattatcag | aagatgaaga | aactgaagta | 1260 |
| caagagcaga | tgaatctcct | aaattcaaga | tgggaatgcc | tcagggtagc | tagcatggaa | 1320 |
| aaacaaagca | atttacatag | agttttaatg | gatctccaga | atcagaaact | gaaagagttg | 1380 |
| aatgactggc | taacaaaaac | agaagaaaga | acaaggaaaa | tggaggaaga | gcctcttgga | 1440 |
| cctgatcttg | aagacctaaa | acgccaagta | caacaacata | aggtgcttca | agaagatcta | 1500 |
| gaacaagaac | aagtcagggt | caattctctc | actcacatgg | tggtggtagt | tgatgaatct | 1560 |
| agtggagatc | acgcaactgc | tgctttggaa | gaacaactta | aggtattggg | agatcgatgg | 1620 |
| gcaaacatct | gtagatggac | agaagaccgc | tgggttcttt | tacaagacat | ccttctcaaa | 1680 |
| tggcaacgtc | ttactgaaga | acagtgcctt | tttagtgcat | ggcttcaga | aaagaagat | 1740 |
| gcagtgaaca | agattcacac | aactggcttt | aaagatcaaa | atgaaatgtt | atcaagtctt | 1800 |
| caaaaactgg | ccgttttaaa | agcggatcta | gaaaagaaaa | agcaatccat | gggcaaactg | 1860 |
| tattcactca | aacaagatct | tctttcaaca | ctgaagaata | agtcagtgac | ccagaagacg | 1920 |
| gaagcatggc | tggataactt | tgcccggtgt | tgggataatt | tagtccaaaa | acttgaaaag | 1980 |
| agtacagcac | agatttcaca | ggctgctcct | ggactgacca | ctattggagc | ctctcctact | 2040 |
| cagactgtta | ctctggtgac | acaacctgtg | gttactaagg | aaactgccat | ctccaaacta | 2100 |
| gaaatgccat | cttccttgat | gttggaggta | cctgctctgg | cagatttcaa | ccggcttgg | 2160 |

```
acagaactta ccgactggct ttctctgctt gatcaagtta taaaatcatg gcagcccgtg    2220
ggcgatctcc tcattgactc tctccaagat cacctcgaga aagtcaaggc acttcgagga    2280
gaaattgcgc ctctgaaaga gaacgtgagc cacgtcaatg accttgctcg ccagcttacc    2340
actttgggca ttcagctctc accgtataac ctcagcactc tggaagacct gaacaccaga    2400
tggaagcttc tgcaggtggc cgtcgaggac cgagtcaggc agctgcatga agcccacagg    2460
gactttggtc cagcatctca gcactttctt tccacgtctg tccagggtcc ctgggagaga    2520
gccatctcgc caaacaaagt gccctactat atcaaccacg agactcaaac aacttgctgg    2580
gaccatccca aaatgacaga gctctaccag tctttagctg acctgaataa tgtcagattc    2640
tcagcttata ggactgccat gaaactccga agactgcaga aggccctttg cttggatctc    2700
ttgagcctgt cagctgcatg tgatgccttg gaccagcaca acctcaagca aaatgaccag    2760
cccatggata tcctgcagat tattaattgt ttgaccacta tttatgaccg cctggagcaa    2820
gagcacaaca atttggtcaa cgtccctctc tgcgtggata tgtgtctgaa ctggctgctg    2880
aatgtttatg atacgggacg aacagggagg atccgtgtcc tgtcttttaa aactggcatc    2940
atttccctgt gtaaagcaca tttggaagac aagtacagat accttttcaa gcaagtggca    3000
agttcaacag gattttgtga ccagcgcagg ctgggcctcc ttctgcatga ttctatccaa    3060
attccaagac agttgggtga agttgcatcc tttgggggca gtaacattga gccaagtgtc    3120
cggagctgct tccaatttgc taataataag ccagagatcg aagcggccct cttcctagac    3180
tggatgagac tggaacccca gtccatggtg tggctgcccg tcctgcacag agtggctgct    3240
gcagaaactg ccaagcatca ggccaaatgt aacatctgca aagagtgtcc aatcattgga    3300
ttcaggtaca ggagtctaaa gcactttaat tatgacatct gccaaagctg cttttttttct    3360 ggtcgagttg caaaaggcca taaatgcac tatcccatgg tggaatattg cactccgact    3420
acatcaggag aagatgttcg agactttgcc aaggtactaa aaacaaatt tcgaaccaaa    3480 aggtattttg cgaagcatcc ccgaatgggc tacctgccag tgcagactgt cttagagggg    3540
gacaacatgg aaactgacac aatg                                          3564
```

<210> SEQ ID NO 15
<211> LENGTH: 3693
<212> TYPE: DNA
<213> ORGANISM: Artificial Sequence
<220> FEATURE:
<223> OTHER INFORMATION: micro-Dys4

<400> SEQUENCE: 15

```
atgctttggt gggaagaagt agaggactgt tatgaaagag aagatgttca aaagaaaaca     60
ttcacaaaat gggtaaatgc acaatttctct aagtttggga agcagcatat tgagaacctc    120
ttcagtgacc tacaggatgg gaggcgcctc ctagacctcc tcgaaggcct gacagggcaa    180
aaactgccaa agaaaaagg atccacaaga gttcatgccc tgaacaatgt caacaaggca    240
ctgcgggttt tgcagaacaa taatgttgat ttagtgaata ttggaagtac tgacatcgta    300
gatggaaatc ataaactgac tcttggtttg atttggaata taatcctcca ctggcaggtc    360
aaaaatgtaa tgaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggcttttgaat gctctcatcc atagtcatag gccagaccta    540
tttgactgga atagtgtggt ttgccagcag tcagccacac aacgactgga acatgcattc    600
```

```
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaaggcc acctaaagtg    780
actaaagaag aacattttca gttacatcat caaatgcact attctcaaca gatcacggtc    840
agtctagcac agggatatga gagaacttct tcccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
aaacaaagca atttacatag agttttaatg gatctccaga atcagaaact gaaagagttg   1380
aatgactggc taacaaaaac agaagaaaga acaaggaaaa tggaggaaga gcctcttgga   1440
cctgatcttg aagacctaaa acgccaagta caacaacata aggtgcttca agaagatcta   1500
gaacaagaac aagtcagggt caattctctc actcacatgg tggtggtagt tgatgaatct   1560
agtggagatc acgcaactgc tgctttggaa gaacaactta aggtattggg agatcgatgg   1620
gcaaacatct gtagatggac agaagaccgc tgggttcttt tacaagacat ccttctcaaa   1680
tggcaacgtc ttactgaaga acagtgcctt tttagtgcat ggctttcaga aaagaagat    1740 gcagtgaaca agattcacac aactggcttt aaagatcaaa atgaaatgtt atcaagtctt   1800
caaaaactgg ccgtttttaaa agcggatcta gaaaagaaaa agcaatccat gggcaaactg   1860
tattcactca aacaagatct tctttcaaca ctgaagaata agtcagtgac ccagaagacg   1920
gaagcatggc tggataactt tgcccggtgt tgggataatt tagtccaaaa acttgaaaag   1980
agtacagcac agatttcaca ggctgctcct ggactgacca ctattggagc ctctcctact   2040
cagactgtta ctctggtgac acaacctgtg gttactaagg aaactgccat ctccaaacta   2100
gaaatgccat cttccttgat gttggaggag ctgcctcctg aggagagagc ccagaatgtc   2160
actcggcttc tacgaaagca ggctgaggag gtcaatactg agtgggaaaa attgaacctg   2220
cactccgctg actggcagag aaaaatagat gagacccttg aaagactcca ggaacttcaa   2280
gaggccacgg atgagctgga cctcaagctg cgccaagctg aggtgatcaa gggatcctgg   2340
cagcccgtgg gcgatctcct cattgactct ctccaagatc acctcgagaa agtcaaggca   2400
cttcgaggag aaaattgcgcc tctgaaagag aacgtgagcc acgtcaatga ccttgctcgc   2460
cagcttacca ctttgggcat tcagctctca ccgtataacc tcagcactct ggaagacctg   2520
aacaccagat ggaagcttct gcaggtggcc gtcgaggacc gagtcaggca gctgcatgaa   2580
gcccacaggg actttggtcc agcatctcag cactttcttt ccacgtctgt ccagggtccc   2640
tgggagagag ccatctcgcc aaacaaagtg ccctactata tcaaccacga gactcaaaca   2700
acttgctggg accatcccaa aatgacagag ctctaccagt ctttagctga cctgaataat   2760
gtcagattct cagcttatag gactgccatg aaactccgaa gactgcagaa ggccctttgc   2820
ttggatctct gagcctgtc agctgcatgt gatgccttgg accagcacaa cctcaagcaa   2880
aatgaccagc ccatggatat cctgcagatt attaattgtt tgaccactat ttatgaccgc   2940
ctggagcaag agcacaacaa tttggtcaac gtccctctct gcgtggatat gtgtctgaac   3000
```

```
tggctgctga atgtttatga tacgggacga acagggagga tccgtgtcct gtcttttaaa    3060
actggcatca tttccctgtg taaagcacat ttgaagaca agtacagata ccttttcaag    3120
caagtggcaa gttcaacagg attttgtgac cagcgcaggc tgggcctcct tctgcatgat    3180
tctatccaaa ttccaagaca gttgggtgaa gttgcatcct tgggggcag  taacattgag    3240 ccaagtgtcc ggagctgctt ccaatttgct aataataagc cagagatcga agcggccctc    3300
ttcctagact ggatgagact ggaacccag  tccatggtgt ggctgcccgt cctgcacaga    3360
gtggctgctg cagaaactgc caagcatcag gccaaatgta acatctgcaa agagtgtcca    3420
atcattggat tcaggtacag gagtctaaag cactttaatt atgacatctg ccaaagctgc    3480 ttttttttctg gtcgagttgc aaaaggccat aaaatgcact atcccatggt ggaatattgc    3540
actccgacta catcaggaga agatgttcga ctttgccca aggtactaaa aaacaaattt    3600
cgaaccaaaa ggtattttgc gaagcatccc cgaatgggct acctgccagt gcagactgtc    3660
ttagaggggg acaacatgga aactgacaca atg                                 3693
```

<210> SEQ ID NO 16
<211> LENGTH: 3810
<212> TYPE: DNA
<213> ORGANISM: Artificial Sequence
<220> FEATURE:
<223> OTHER INFORMATION: micro-Dys5

<400> SEQUENCE: 16

```
atgctttggt gggaagaagt agaggactgt tatgaaagag aagatgttca aaagaaaaca      60
ttcacaaaat gggtaaatgc acaatttctct aagtttggga agcagcatat tgagaacctc    120
ttcagtgacc tacaggatgg gaggcgcctc ctagacctcc tcgaaggcct gacagggcaa    180
aaactgccaa agaaaaagg  atccacaaga gttcatgccc tgaacaatgt caacaaggca    240
ctgcgggttt tgcagaacaa taatgttgat ttagtgaata ttggaagtac tgacatcgta    300
gatggaaatc ataaactgac tcttggtttg atttggaata taatcctcca ctggcaggtc    360
aaaaatgtaa tgaaaatat  catggctgga ttgcaacaaa ccaacagtga aaagattctc    420
ctgagctggg tccgacaatc aactcgtaat tatccacagg ttaatgtaat caacttcacc    480
accagctggt ctgatggcct ggcttttgaat gctctcatcc atagtcatag gccagaccta    540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaaggcc acctaaagtg    780
actaaagaag aacattttttca gttacatcat caaatgcact attctcaaca gatcacggtc    840
agtctagcac agggatatga gagaacttct tcccctaagc ctcgattcaa gagctatgcc    900
tacacacagg ctgcttatgt caccacctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
```

```
aaacaaagca atttacattc ttatgtgcct tctacttatt tgactgaaat cactcatgtc   1380
tcacaagccc tattagaagt ggaacaactt ctcaatgctc ctgacctctg tgctaaggac   1440
tttgaagatc tctttaagca agaggagtct ctgaagaata taaaagatag tctacaacaa   1500
agctcaggtc ggattgacat tattcatagc aagaagacag cagcattgca aagtgcaacg   1560
cctgtggaaa gggtgaagct acaggaagct ctctcccagc ttgatttcca atgggaaaaa   1620
gttaacaaaa tgtacaagga ccgacaaggg cgatttgaca gatctgttga gaaatggcgg   1680
cgttttcatt atgatataaa gatatttaat cagtggctaa cagaagctga acagtttctc   1740
agaaagacac aaattcctga gaattgggaa catgctaaat acaaatggta tcttaaggaa   1800
ctccaggatg gcattgggca gcggcaaact gttgtcagaa cattgaatgc aactggggaa   1860 gaataattc agcaatcctc aaaaacagat gccagtattc tacaggaaaa attgggaagc   1920
ctgaatctgc ggtggcagga ggtctgcaaa cagctgtcag acagaaaaaa gaggctagaa   1980
gaacaatctg accagtggaa gcgtctgcac ctttctctgc aggaacttct ggtgtggcta   2040
cagctgaaag atgatgaatt aagccggcag gcacctattg gagcgacttt ccagcagtt    2100 cagaagcaga acgatgtaca tagggccttc aagagggaat tgaaaactaa agaacctgta   2160
atcatgagta ctcttgagac tgtacgaata tttctgacag agcagccttt ggaaggacta   2220
gagaaactct accaggagcc cagagagctg cctcctgagg agagagccca gaatgtcact   2280
cggcttctac gaaagcaggc tgaggaggtc aatactgagt gggaaaaatt gaacctgcac   2340
tccgctgact ggcagagaaa aatagatgag acccttgaaa gactccagga acttcaagag   2400
gccacggatg agctggacct caagctgcgc caagctgagg tgatcaaggg atcctggcag   2460
cccgtgggcg atctcctcat tgactctctc caagatcacc tcgagaaagt caaggcactt   2520
cgaggagaaa ttgcgcctct gaaagagaac gtgagccacg tcaatgacct tgctcgccag   2580
cttaccactt tgggcattca gctctcaccg tataacctca gcactctgga agacctgaac   2640
accagatgga agcttctgca ggtggccgtc gaggaccgag tcaggcagct gcatgaagcc   2700
cacagggact ttggtccagc atctcagcac tttctttcca cgtctgtcca gggtccctgg   2760
gagagagcca tctcgccaaa caaagtgccc tactatatca accacgagac tcaaacaact   2820
tgctgggacc atcccaaaat gacagagctc taccagtctt tagctgacct gaataatgtc   2880
agattctcag cttataggac tgccatgaaa ctccgaagac tgcagaaggc cctttgcttg   2940
gatctcttga gcctgtcagc tgcatgtgat gccttggacc agcacaacct caagcaaaat   3000
gaccagccca tggatatcct gcagattatt aattgtttga ccactattta tgaccgcctg   3060
gagcaagagc acaacaattt ggtcaacgtc cctctctgcg tggatatgtg tctgaactgg   3120
ctgctgaatg tttatgatac gggacgaaca gggaggatcc gtgtcctgtc ttttaaaact   3180
ggcatcattt ccctgtgtaa agcacatttg gaagacaagt acagataccta tttcaagcaa   3240 gtggcaagtt caacaggatt tgtgaccag cgcaggctgg gcctccttct gcatgattct   3300
atccaaattc aagacagtt gggtgaagtt gcatcctttg ggggcagtaa cattgagcca   3360
agtgtccgga gctgcttcca atttgctaat aataagccag agatcgaagc ggccctcttc   3420
ctagactgga tgagactgga accccagtcc atggtgtggc tgcccgtcct gcacagagtg   3480
gctgctgcag aaactgccaa gcatcaggcc aaatgtaaca tctgcaaaga gtgtccaatc   3540
attggattca ggtacaggag tctaaagcac tttaattatg acatctgcca aagctgcttt   3600
ttttctggtc gagttgcaaa aggccataaa atgcactatc ccatggtgga atattgcact   3660
ccgactacat caggagaaga tgttcgagac tttgccaagg tactaaaaaa caaatttcga   3720
```

-continued

| | |
|---|---|
| accaaaaggt attttgcgaa gcatcccga atgggctacc tgccagtgca gactgtctta | 3780 |
| gaggggggaca acatggaaac tgacacaatg | 3810 |

<210> SEQ ID NO 17
<211> LENGTH: 4149
<212> TYPE: DNA
<213> ORGANISM: Artificial Sequence
<220> FEATURE:
<223> OTHER INFORMATION: micro-Dys6

<400> SEQUENCE: 17

| | |
|---|---|
| atgctttggt gggaagaagt agaggactgt tatgaaagag aagatgttca aaagaaaaca | 60 |
| ttcacaaaat gggtaaatgc acaattttct aagtttggga agcagcatat tgagaacctc | 120 |
| ttcagtgacc tacaggatgg gaggcgcctc ctagacctcc tcgaaggcct gacagggcaa | 180 |
| aaactgccaa agaaaaagg atccacaaga gttcatgccc tgaacaatgt caacaaggca | 240 |
| ctgcgggttt tgcagaacaa taatgttgat ttagtgaata ttggaagtac tgacatcgta | 300 |
| gatggaaatc ataaactgac tcttggtttg atttggaata taatcctcca ctggcaggtc | 360 |
| aaaaatgtaa tgaaaatat catggctgga ttgcaacaaa ccaacagtga aaagattctc | 420 |
| ctgagctggg tccgacaatc aactcgtaat tatccacagg ttaatgtaat caacttcacc | 480 |
| accagctggt ctgatggcct ggctttgaat gctctcatcc atagtcatag gccagaccta | 540 |
| tttgactgga atagtgtggt tgccagcag tcagccacac aacgactgga acatgcattc | 600 |
| aacatcgcca gatatcaatt aggcatagag aaactactcg atcctgaaga tgttgatacc | 660 |
| acctatccag ataagaagtc catcttaatg tacatcacat cactcttcca agttttgcct | 720 |
| caacaagtga gcattgaagc catccaggaa gtggaaatgt tgccaaggcc acctaaagtg | 780 |
| actaaagaag aacattttca gttacatcat caaatgcact attctcaaca gatcacggtc | 840 |
| agtctagcac agggatatga gagaacttct tcccctaagc ctcgattcaa gagctatgcc | 900 |
| tacacacagg ctgcttatgt caccacctct gaccctacac ggagcccatt tccttcacag | 960 |
| catttggaag ctcctgaaga caagtcattt ggcagttcat tgatggagag tgaagtaaac | 1020 |
| ctggaccgtt atcaaacagc tttagaagaa gtattatcgt ggcttcttc tgctgaggac | 1080 |
| acattgcaag cacaaggaga gatttctaat gatgtggaag tggtgaaaga ccagtttcat | 1140 |
| actcatgagg ggtacatgat ggatttgaca gcccatcagg gccgggttgg taatattcta | 1200 |
| caattgggaa gtaagctgat tggaacagga aaattatcag aagatgaaga aactgaagta | 1260 |
| caagagcaga tgaatctcct aaattcaaga tgggaatgcc tcagggtagc tagcatggaa | 1320 |
| aaacaaagca atttacatag agttttaatg gatctccaga tcagaaact gaaagagttg | 1380 |
| aatgactggc taacaaaaac agaagaaaga acaggaaaa tggaggaaga gcctcttgga | 1440 |
| cctgatcttg aagacctaaa acgccaagta caacaacata aggtgcttca agaagatcta | 1500 |
| gaacaagaac aagtcagggt caattctctc actcacatgg tggtggtagt tgatgaatct | 1560 |
| agtggagatc acgcaactgc tgctttggaa gaacaactta aggtattggg agatcgatgg | 1620 |
| gcaaacatct gtagatggac agaagaccgc tgggttcttt tacaagacat ccttctcaaa | 1680 |
| tggcaacgtc ttactgaaga acagtgcctt tttagtgcat ggcttcaga aaagaagat | 1740 |
| gcagtgaaca agattcacac aactggcttt aaagatcaaa atgaaatgtt atcaagtctt | 1800 |
| caaaaactgg ccgttttaaa agcggatcta gaaaagaaaa agcaatccat gggcaaactg | 1860 |
| tattcactca acaagatct tctttcaaca ctgaagaata agtcagtgac ccagaagacg | 1920 |

-continued

```
gaagcatggc tggataactt tgcccggtgt tgggataatt tagtccaaaa acttgaaaag    1980
agtacagcac agatttcaca ggctattcac actgtccgtg aagaaacgat gatggtgatg    2040
actgaagaca tgcctttgga aatttcttat gtgccttcta cttatttgac tgaaatcact    2100
catgtctcac aagccctatt agaagtggaa caacttctca atgctcctga cctctgtgct    2160
aaggactttg aagatctctt taagcaagag gagtctctga agaatataaa agatagtcta    2220
caacaaagct caggtcggat tgacattatt catagcaaga agacagcagc attgcaaagt    2280
gcaacgcctg tggaaagggt gaagctacag gaagctctct cccagcttga tttccaatgg    2340
gaaaaagtta acaaaatgta caaggaccga caagggcgat ttgacagatc tgttgagaaa    2400
tggcggcgtt ttcattatga tataaagata tttaatcagt ggctaacaga agctgaacag    2460
tttctcagaa agacacaaat tcctgagaat tgggaacatg ctaaatacaa atggtatctt    2520
aaggaactcc aggatggcat tgggcagcgg caaactgttg tcagaacatt gaatgcaact    2580
ggggaagaaa taattcagca atcctcaaaa acagatgcca gtattctaca ggaaaaattg    2640
ggaagcctga atctgcggtg gcaggaggtc tgcaaacagc tgtcagacag aaaaaagagg    2700
ctagaagaac aacttgaaag actccaggaa cttcaagagg ccacggatga gctggacctc    2760
aagctgcgcc aagctgaggt gatcaaggga tcctggcagc ccgtgggcga tctcctcatt    2820
gactctctcc aagatcacct cgagaaagtc aaggcacttc gaggagaaat tgcgcctctg    2880
aaagagaacg tgagccacgt caatgacctt gctcgccagc ttaccacttt gggcattcag    2940
ctctcaccgt ataacctcag cactctggaa gacctgaaca ccagatggaa gcttctgcag    3000
gtggccgtcg aggaccgagt caggcagctg catgaagccc acagggactt tggtccagca    3060
tctcagcact ttcttttccac gtctgtccag ggtccctggg agagagccat ctcgccaaac    3120
aaagtgccct actatatcaa ccacgagact caaacaactt gctgggacca tcccaaaatg    3180
acagagctct accagtcttt agctgacctg aataatgtca gattctcagc ttataggact    3240
gccatgaaac tccgaagact gcagaaggcc ctttgcttgg atctcttgag cctgtcagct    3300
gcatgtgatg ccttggacca gcacaacctc aagcaaaatg accagcccat ggatatcctg    3360
cagattatta attgtttgac cactatttat gaccgcctgg agcaagagca caacaatttg    3420
gtcaacgtcc ctctctgcgt ggatatgtgt ctgaactggc tgctgaatgt ttatgatacg    3480
ggacgaacag ggaggatccg tgtcctgtct tttaaaactg gcatcatttc cctgtgtaaa    3540
gcacatttgg aagacaagta cagatacctt ttcaagcaag tggcaagttc aacaggattt    3600
tgtgaccagc gcaggctggg cctccttctg catgattcta tccaaattcc aagacagttg    3660
ggtgaagttg catcctttgg gggcagtaac attgagccaa gtgtccggag ctgcttccaa    3720
tttgctaata ataagccaga gatcgaagcg gccctcttcc tagactggat gagactggaa    3780
ccccagtcca tggtgtggct gcccgtcctg cacagagtgg ctgctgcaga aactgccaag    3840
catcaggcca aatgtaacat ctgcaaagag tgtccaatca ttggattcag gtacaggagt    3900
ctaaagcact ttaattatga catctgccaa agctgctttt tttctggtcg agttgcaaaa    3960
ggccataaaa tgcactatcc catggtggaa tattgcactc cgactacatc aggagaagat    4020
gttcgagact tgccaaggt actaaaaaac aaatttcgaa ccaaaaggta ttttgcgaag    4080
catccccgaa tgggctacct gccagtgcag actgtcttag aggggacaa catggaaact    4140
gacacaatg                                                           4149
```

<210> SEQ ID NO 18
<211> LENGTH: 4212

| | |
|---|---|
| <212> TYPE: DNA | |
| <213> ORGANISM: Artificial Sequence | |
| <220> FEATURE: | |
| <223> OTHER INFORMATION: micro-Dys7 | |

<400> SEQUENCE: 18

| | |
|---|---|
| atgctttggt gggaagaagt agaggactgt tatgaaagag aagatgttca aaagaaaaca | 60 |
| ttcacaaaat gggtaaatgc acaattttct aagtttggga agcagcatat tgagaacctc | 120 |
| ttcagtgacc tacaggatgg gaggcgcctc ctagacctcc tcgaaggcct gacagggcaa | 180 |
| aaactgccaa agaaaaagg atccacaaga gttcatgccc tgaacaatgt caacaaggca | 240 |
| ctgcgggttt tgcagaacaa taatgttgat ttagtgaata ttggaagtac tgacatcgta | 300 |
| gatggaaatc ataaactgac tcttggtttg atttggaata taatcctcca ctggcaggtc | 360 |
| aaaaatgtaa tgaaaatat catggctgga ttgcaacaaa ccaacagtga aaagattctc | 420 |
| ctgagctggg tccgacaatc aactcgtaat tatccacagg ttaatgtaat caacttcacc | 480 |
| accagctggt ctgatggcct ggctttgaat gctctcatcc atagtcatag gccagaccta | 540 |
| tttgactgga atagtgtggt ttgccagcag tcagccacac aacgactgga acatgcattc | 600 |
| aacatcgcca gatatcaatt aggcatagag aaactactcg atcctgaaga tgttgatacc | 660 |
| acctatccag ataagaagtc catcttaatg tacatcacat cactcttcca agttttgcct | 720 |
| caacaagtga gcattgaagc catccaggaa gtggaaatgt tgccaaggcc acctaaagtg | 780 |
| actaagaag aacattttca gttacatcat caaatgcact attctcaaca gatcacggtc | 840 |
| agtctagcac agggatatga gagaacttct tcccctaagc ctcgattcaa gagctatgcc | 900 |
| tacacacagg ctgcttatgt caccacctct gaccctacac ggagcccatt tccttcacag | 960 |
| catttggaag ctcctgaaga caagtcattt ggcagttcat tgatggagag tgaagtaaac | 1020 |
| ctggaccgtt atcaaacagc tttagaagaa gtattatcgt ggcttctttc tgctgaggac | 1080 |
| acattgcaag cacaaggaga gatttctaat gatgtggaag tggtgaaaga ccagtttcat | 1140 |
| actcatgagg ggtacatgat ggatttgaca gcccatcagg gccgggttgg taatattcta | 1200 |
| caattgggaa gtaagctgat tggaacagga aaattatcag aagatgaaga aactgaagta | 1260 |
| caagagcaga tgaatctcct aaattcaaga tgggaatgcc tcagggtagc tagcatggaa | 1320 |
| aaacaaagca atttacatag agttttaatg gatctccaga atcagaaact gaaagagttg | 1380 |
| aatgactggc taacaaaaac agaagaaaga acaaggaaaa tggaggaaga gcctcttgga | 1440 |
| cctgatcttg aagacctaaa acgccaagta caacaacata aggtgcttca agaagatcta | 1500 |
| gaacaagaac aagtcagggt caattctctc actcacatgg tggtggtagt tgatgaatct | 1560 |
| agtggagatc acgcaactgc tgctttggaa gaacaactta aggtattggg agatcgatgg | 1620 |
| gcaaacatct gtagatggac agaagaccgc tgggttcttt acaagacat ccttctcaaa | 1680 |
| tggcaacgtc ttactgaaga acagtgcctt tttagtgcat ggctttcaga aaagaagat | 1740 |
| gcagtgaaca agattcacac aactggcttt aaagatcaaa atgaaatgtt atcaagtctt | 1800 |
| caaaaactgg ccgttttaaa agcggatcta gaaaagaaaa agcaatccat gggcaaactg | 1860 |
| tattcactca acaagatct tctttcaaca ctgaagaata agtcagtgac ccagaagacg | 1920 |
| gaagcatggc tggataactt tgcccggtgt tgggataatt tagtccaaaa acttgaaaag | 1980 |
| agtacagcac agatttcaca ggctgctcct ggactgacca ctattggagc ctctcctact | 2040 |
| cagactgtta ctctggtgac acaacctgtg gttactaagg aaactgccat ctccaaacta | 2100 |
| gaaatgccat cttccttgat gttggagtct tatgtgcctt ctacttattt gactgaaatc | 2160 |

```
actcatgtct cacaagccct attagaagtg gaacaacttc tcaatgctcc tgacctctgt    2220
gctaaggact ttgaagatct cttttaagcaa gaggagtctc tgaagaatat aaaagatagt   2280
ctacaacaaa gctcaggtcg gattgacatt attcatagca agaagacagc agcattgcaa    2340
agtgcaacgc ctgtggaaag ggtgaagcta caggaagctc tctcccagct tgatttccaa    2400
tgggaaaaag ttaacaaaat gtacaaggac cgacaagggc gatttgacag atctgttgag    2460
aaatggcggc gttttcatta tgatataaag atatttaatc agtggctaac agaagctgaa    2520
cagtttctca gaaagacaca aattcctgag aattgggaac atgctaaata caaatggtat    2580
cttaaggaac tccaggatgg cattgggcag cggcaaactg ttgtcagaac attgaatgca    2640
actggggaag aaataattca gcaatcctca aaaacagatg ccagtattct acaggaaaaa    2700
ttgggaagcc tgaatctgcg gtggcaggag gtctgcaaac agctgtcaga cagaaaaaag    2760
aggctagaag aacaacttga aagactccag gaacttcaag aggccacgga tgagctggac    2820
ctcaagctgc gccaagctga ggtgatcaag ggatcctggc agcccgtggg cgatctcctc    2880
attgactctc tccaagatca cctcgagaaa gtcaaggcac ttcgaggaga aattgcgcct    2940
ctgaaagaga acgtgagcca cgtcaatgac cttgctcgcc agcttaccac tttgggcatt    3000
cagctctcac cgtataacct cagcactctg gaagacctga acaccagatg gaagcttctg    3060
caggtggccg tcgaggaccg agtcaggcag ctgcatgaag cccacaggga ctttggtcca    3120
gcatctcagc actttctttc cacgtctgtc cagggtccct gggagagagc catctcgcca    3180
aacaaagtgc cctactatat caaccacgag actcaaacaa cttgctggga ccatcccaaa    3240
atgacagagc tctaccagtc tttagctgac ctgaataatg tcagattctc agcttatagg    3300
actgccatga aactccgaag actgcagaag gcccttttgct tggatctctt gagcctgtca    3360
gctgcatgtg atgccttgga ccagcacaac ctcaagcaaa atgaccagcc catggatatc    3420
ctgcagatta ttaattgttt gaccactatt tatgaccgcc tggagcaaga gcacaacaat    3480
ttggtcaacg tccctctctg cgtggatatg tgtctgaact ggctgctgaa tgtttatgat    3540
acgggacgaa cagggaggat ccgtgtcctg tcttttaaaa ctggcatcat ttccctgtgt    3600
aaagcacatt tggaagacaa gtacagatac cttttcaagc aagtggcaag ttcaacagga    3660
ttttgtgacc agcgcaggct gggcctcctt ctgcatgatt ctatccaaat tccaagacag    3720
ttgggtgaag ttgcatcctt tgggggcagt aacattgagc caagtgtccg gagctgcttc    3780
caatttgcta ataataagcc agagatcgaa gcggccctct tcctagactg gatgagactg    3840
gaaccccagt ccatggtgtg gctgcccgtc ctgcacagag tggctgctgc agaaactgcc    3900
aagcatcagg ccaaatgtaa catctgcaaa gagtgtccaa tcattggatt caggtacagg    3960
agtctaaagc actttaatta tgacatctgc caaagctgct ttttttctgg tcgagttgca    4020
aaaggccata aaatgcacta tcccatggtg gaatattgca ctccgactac atcaggagaa    4080
gatgttcgag actttgccaa ggtactaaaa aacaaatttc gaaccaaaag gtattttgcg    4140
aagcatcccc gaatgggcta cctgccagtg cagactgtct tagaggggga caacatggaa    4200
actgacacaa tg                                                        4212
```

<210> SEQ ID NO 19
<211> LENGTH: 450
<212> TYPE: DNA
<213> ORGANISM: Artificial Sequence
<220> FEATURE:
<223> OTHER INFORMATION: CK8 promoter

<400> SEQUENCE: 19

```
ctagactagc atgctgccca tgtaaggagg caaggcctgg ggacacccga gatgcctggt    60
tataattaac ccagacatgt ggctgccccc cccccccaa cacctgctgc ctctaaaaat   120
aaccctgcat gccatgttcc cggcgaaggg ccagctgtcc cccgccagct agactcagca   180
cttagtttag gaaccagtga gcaagtcagc ccttggggca gcccatacaa ggccatgggg   240
ctgggcaagc tgcacgcctg gtccgggggt gggcacggtg cccgggcaac gagctgaaag   300
ctcatctgct ctcaggggcc cctccctggg acagcccct cctggctagt cacaccctgt   360
aggctcctct atataaccca ggggcacagg ggctgccctc attctaccac cacctccaca   420
gcacagacag acactcagga gccagccagc                                   450

<210> SEQ ID NO 20
<211> LENGTH: 20
<212> TYPE: PRT
<213> ORGANISM: Artificial Sequence
<220> FEATURE:
<223> OTHER INFORMATION: Hinge-like region between SR15 and SR16

<400> SEQUENCE: 20

Ile His Thr Val Arg Glu Glu Thr Met Met Val Met Thr Glu Asp Met
1               5                   10                  15

Pro Leu Glu Ile
            20

<210> SEQ ID NO 21
<211> LENGTH: 20
<212> TYPE: PRT
<213> ORGANISM: Artificial Sequence
<220> FEATURE:
<223> OTHER INFORMATION: Hinge-like region within SR23

<400> SEQUENCE: 21

Leu Glu Gly Leu Glu Lys Leu Tyr Gln Glu Pro Arg Glu Leu Pro Pro
1               5                   10                  15

Glu Glu Arg Ala
            20

<210> SEQ ID NO 22
<211> LENGTH: 8391
<212> TYPE: DNA
<213> ORGANISM: Artificial Sequence
<220> FEATURE:
<223> OTHER INFORMATION: CK8-micro-Dys5 cassette

<400> SEQUENCE: 22
cagcagctgc gcgctcgctc gctcactgag gccgcccggg caaagcccgg gcgtcgggcg    60
acctttggtc gcccggcctc agtgagcgag cgagcgcgca gagggagt ggccaactcc   120 atcactaggg gttccttgta gttaatgatt aacccgccat gctacttatc tacaaacgct   180
agcatgctgc ccatgtaagg aggcaaggcc tgggacacc cgagatgcct ggttataatt   240
aacccagaca tgtggctgcc cccccccccc caacacctgc tgcctctaaa ataaccctg   300 catgccatgt tcccggcgaa gggccagctg tccccgcca gctagactca gcacttagtt   360
taggaaccag tgagcaagtc agcccttggg gcagcccata caaggccatg gggctgggca   420
agctgcacgc ctgggtccgg ggtgggcacg gtgcccgggc aacgagctga agctcatct   480 gctctcaggg gcccctccct ggggacagcc cctcctggct agtcacaccc tgtaggctcc   540
tctatataac caggggcac aggggctgcc ctcattctac caccacctcc acagcacaga   600
```

```
cagacactca ggagccagcc agcgtcgagg ttaacccgcg gccgtttttt ttatcgctgc    660
cttgatatac actttccacc atgctttggt gggaagaagt agaggactgt tatgaaagag    720
aagatgttca aaagaaaaca ttcacaaaat gggtaaatgc acaattttct aagtttggga    780
agcagcatat tgagaacctc ttcagtgacc tacaggatgg gaggcgcctc ctagacctcc    840
tcgaaggcct gacagggcaa aaactgccaa agaaaaagg atccacaaga gttcatgccc     900
tgaacaatgt caacaaggca ctgcgggttt tgcagaacaa taatgttgat ttagtgaata    960
ttggaagtac tgacatcgta gatggaaatc ataaactgac tcttggtttg atttggaata   1020
taatcctcca ctggcaggtc aaaaatgtaa tgaaaatat catggctgga ttgcaacaaa    1080
ccaacagtga aaagattctc ctgagctggg tccgacaatc aactcgtaat tatccacagg   1140
ttaatgtaat caacttcacc accagctggt ctgatggcct ggctttgaat gctctcatcc   1200
atagtcatag gccagaccta tttgactgga atagtgtggt ttgccagcag tcagccacac   1260
aacgactgga acatgcattc aacatcgcca gatatcaatt aggcatagag aaactactcg   1320
atcctgaaga tgttgatacc acctatccag ataagaagtc catcttaatg tacatcacat   1380
cactcttcca agtttgcct caacaagtga gcattgaagc catccaggaa gtggaaatgt    1440
tgccaaggcc acctaaagtg actaaagaag aacattttca gttacatcat caaatgcact   1500
attctcaaca gatcacggtc agtctagcac agggatatga gagaacttct tcccctaagc   1560
ctcgattcaa gagctatgcc tacacacagg ctgcttatgt caccacctct gaccctacac   1620
ggagcccatt tccttcacag catttggaag ctcctgaaga caagtcattt ggcagttcat   1680
tgatggagag tgaagtaaac ctggaccgtt atcaaacagc tttagaagaa gtattatcgt   1740
ggcttctttc tgctgaggac acattgcaag cacaaggaga gatttctaat gatgtggaag   1800
tggtgaaaga ccagtttcat actcatgagg ggtacatgat ggatttgaca gcccatcagg   1860
gccgggttgg taatattcta caattgggaa gtaagctgat tggaacagga aaattatcag   1920
aagatgaaga aactgaagta caagagcaga tgaatctcct aaattcaaga tgggaatgcc   1980
tcagggtagc tagcatggaa aaacaaagca atttacattc ttatgtgcct tctacttatt   2040
tgactgaaat cactcatgtc tcacaagccc tattagaagt ggaacaactt ctcaatgctc   2100
ctgacctctg tgctaaggac tttgaagatc tctttaagca agaggagtct ctgaagaata   2160
taaaagatag tctacaacaa agctcaggtc ggattgacat tattcatagc aagaagacag   2220
cagcattgca aagtgcaacg cctgtggaaa gggtgaagct acaggaagct ctctcccagc   2280
ttgatttcca atgggaaaaa gttaacaaaa tgtacaagga ccgacaaggg cgatttgaca   2340
gatctgttga gaaatggcgg cgttttcatt atgatataaa gatatttaat cagtggctaa   2400
cagaagctga acagtttctc agaaagacac aaattcctga gaattgggaa catgctaaat   2460
acaaatggta tcttaaggaa ctccaggatg gcattgggca gcggcaaact gttgtcagaa   2520
cattgaatgc aactggggaa gaaataattc agcaatcctc aaaaacagat gccagtattc   2580
tacaggaaaa attgggaagc ctgaatctgc ggtggcagga ggtctgcaaa cagctgtcag   2640
acagaaaaaa gaggctagaa gaacaatctg accagtggaa gcgtctgcac ctttctctgc   2700
aggaacttct ggtgtggcta cagctgaaag atgatgaatt aagccggcag gcacctattg   2760
gaggcgactt tccagcagtt cagaagcaga acgatgtaca tagggccttc aagagggaat   2820
tgaaaactaa agaacctgta atcatgagta ctcttgagac tgtacgaata tttctgacag   2880
agcagccttt ggaaggacta gagaaactct accaggagcc cagagagctg cctcctgagg   2940
agagagccca gaatgtcact cggcttctac gaaagcaggc tgaggaggtc aatactgagt   3000
```

```
gggaaaaatt gaacctgcac tccgctgact ggcagagaaa aatagatgag acccttgaaa   3060
gactccagga acttcaagag gccacggatg agctggacct caagctgcgc caagctgagg   3120
tgatcaaggg atcctggcag cccgtgggcg atctcctcat tgactctctc caagatcacc   3180
tcgagaaagt caaggcactt cgaggagaaa ttgcgcctct gaaagagaac gtgagccacg   3240
tcaatgacct tgctcgccag cttaccactt tgggcattca gctctcaccg tataacctca   3300
gcactctgga agacctgaac accagatgga agcttctgca ggtggccgtc gaggaccgag   3360
tcaggcagct gcatgaagcc cacagggact tggtccagc atctcagcac tttctttcca    3420
cgtctgtcca gggtccctgg gagagagcca tctcgccaaa caaagtgccc tactatatca   3480
accacgagac tcaaacaact tgctgggacc atcccaaaat gacagagctc taccagtctt   3540
tagctgacct gaataatgtc agattctcag cttataggac tgccatgaaa ctccgaagac   3600
tgcagaaggc cctttgcttg gatctcttga gcctgtcagc tgcatgtgat gccttggacc   3660
agcacaacct caagcaaaat gaccagccca tggatatcct gcagattatt aattgtttga   3720
ccactattta tgaccgcctg gagcaagagc acaacaattt ggtcaacgtc cctctctgcg   3780
tggatatgtg tctgaactgg ctgctgaatg tttatgatac gggacgaaca gggaggatcc   3840
gtgtcctgtc ttttaaaact ggcatcattt ccctgtgtaa agcacatttg gaagacaagt   3900
acagatacct tttcaagcaa gtggcaagtt caacaggatt ttgtgaccag cgcaggctgg   3960
gcctccttct gcatgattct atccaaattc aagacagtt gggtgaagtt gcatcctttg    4020
ggggcagtaa cattgagcca agtgtccgga gctgcttcca atttgctaat aataagccag   4080
agatcgaagc ggccctcttc ctagactgga tgagactgga accccagtcc atggtgtggc   4140
tgcccgtcct gcacagagtg gctgctgcag aaactgccaa gcatcaggcc aaatgtaaca   4200
tctgcaaaga gtgtccaatc attggattca ggtacaggag tctaaagcac tttaattatg   4260
acatctgcca aagctgcttt ttttctggtc gagttgcaaa aggccataaa atgcactatc   4320
ccatggtgga atattgcact ccgactacat caggagaaga tgttcgagac tttgccaagg   4380
tactaaaaaa caaatttcga accaaaaggt attttgcgaa gcatcccga atgggctacc     4440
tgccagtgca gactgtctta gagggggaca acatggaaac tgacacaatg taggaagtct   4500
tttccacatg gcagatgaac cggtggctag taataaaaga tccttatttt cattggatct   4560
gtgtgttggt tttttgtgtg ggtaccgttt gtagataagt agcatggcgg gttaatcatt   4620
aactacaagg aaccctagt gatggagttg gccactccct ctctgcgcgc tcgctcgctc     4680
actgaggccg ggcgaccaaa ggtcgcccga cgcccgggct tgcccgggc ggcctcagtg     4740
agcgagcgag cgcgccagct ggcgtaatag cgaagaggcc cgcaccgatc gcccttccca   4800
acagttgcgc agcctgaatg gcgaatggaa ttccagacga ttgagcgtca aaatgtaggt   4860
atttccatga gcgttttcc tgttgcaatg gctgcggta atattgttct ggatattacc     4920
agcaaggccg atagtttgag ttcttctact caggcaagtg atgttattac taatcaaaga   4980
agtattgcga caacggttaa tttgcgtgat ggacagactc ttttactcgg tggcctcact   5040
gattataaaa acacttctca ggattctggc gtaccgttcc tgtctaaaat ccctttaatc   5100
ggcctcctgt ttagctcccg ctctgattct aacgaggaaa gcacgttata cgtgctcgtc   5160
aaagcaacca tagtacgcgc cctgtagcgg cgcattaagc gcggcgggtg tggtggttac   5220
gcgcagcgtg accgctacac ttgccagcgc cctagcgccc gctcctttcg ctttcttccc   5280
ttcctttctc gccacgttcg ccggctttcc ccgtcaagct ctaaatcggg ggctcccttt   5340
```

```
agggttccga tttagtgctt tacggcacct cgaccccaaa aaacttgatt agggtgatgg    5400
ttcacgtagt gggccatcgc cctgatagac ggttttttcgc cctttgacgt tggagtccac   5460
gttctttaat agtggactct tgttccaaac tggaacaaca ctcaacccta tctcggtcta    5520
ttcttttgat ttataaggga ttttgccgat ttcggcctat tggttaaaaa atgagctgat    5580
ttaacaaaaa tttaacgcga attttaacaa aatattaacg tttacaattt aaatatttgc    5640
ttatacaatc ttcctgtttt tggggctttt ctgattatca accggggtac atatgattga    5700
catgctagtt ttacgattac cgttcatcga ttctcttgtt tgctccagac tctcaggcaa    5760
tgacctgata gcctttgtag agacctctca aaaatagcta ccctctccgg catgaattta    5820
tcagctagaa cggttgaata tcatattgat ggtgatttga ctgtctccgg cctttctcac    5880
ccgtttgaat ctttacctac acattactca ggcattgcat ttaaaatata tgagggttct    5940 aaaaatttt atccttgcgt tgaaataaag gcttctcccg caaaagtatt acagggtcat     6000 aatgttttg gtacaaccga tttagctta tgctctgagg ctttattgct taattttgct      6060
aattctttgc cttgcctgta tgatttattg gatgttggaa ttcctgatgc ggtattttct    6120
ccttacgcat ctgtgcggta tttcacaccg catatggtgc actctcagta caatctgctc    6180
tgatgccgca tagttaagcc agccccgaca cccgccaaca cccgctgacg cgccctgacg    6240
ggcttgtctg ctcccggcat ccgcttacag acaagctgtg accgtctccg ggagctgcat    6300
gtgtcagagg ttttcaccgt catcaccgaa acgcgcgaga cgaaagggcc tcgtgatacg    6360 cctatttta taggttaatg tcatgataat aatggtttct tagacgtcag gtggcacttt    6420
tcggggaaat gtgcgcggaa ccctatttg tttattttc taaatacatt caaatatgta     6480
tccgctcatg agacaataac cctgataaat gcttcaataa tattgaaaaa ggaagagtat    6540
gagtattcaa catttccgtg tcgcccttat tcccttttt gcggcatttt gccttcctgt     6600
ttttgctcac ccagaaacgc tggtgaaagt aaaagatgct gaagatcagt tgggtgcacg    6660
agtgggttac atcgaactgg atctcaacag cggtaagatc cttgagagtt ttcgccccga    6720
agaacgtttt ccaatgatga gcacttttaa agttctgcta tgtggcgcgg tattatcccg    6780
tattgacgcc gggcaagagc aactcggtcg ccgcatacac tattctcaga atgacttggt    6840
tgagtactca ccagtcacag aaaagcatct tacggatggc atgacagtaa gagaattatg    6900
cagtgctgcc ataaccatga gtgataacac tgcggccaac ttacttctga caacgatcgg    6960
aggaccgaag gagctaaccg cttttttgca acatggggg atcatgtaa ctcgccttga     7020 tcgttgggaa ccggagctga atgaagccat accaaacgac gagcgtgaca ccacgatgcc    7080
tgtagcaatg gcaacaacgt tgcgcaaact attaactggc gaactactta ctctagcttc    7140
ccggcaacaa ttaatagact ggatggaggc ggataaagtt gcaggaccac ttctgcgctc    7200
ggcccttccg gctggctggt ttattgctga taaatctgga gccggtgagc gtgggtctcg    7260
cggtatcatt gcagcactgg ggccagatgg taagccctcc cgtatcgtag ttatctacac    7320
gacggggagt caggcaacta tggatgaacg aaatagacag atcgctgaga taggtgcctc    7380
actgattaag cattggtaac tgtcagacca agtttactca tatatacttt agattgattt    7440
aaaacttcat ttttaattta aaaggatcta ggtgaagatc cttttttgata atctcatgac    7500 caaaatccct taacgtgagt tttcgttcca ctgagcgtca gaccccgtag aaaagatcaa    7560
aggatcttct tgagatcctt ttttctgcg cgtaatctgc tgcttgcaaa caaaaaaacc    7620
accgctacca gcggtggttt gtttgccgga tcaagagcta ccaactcttt ttccgaaggt    7680
aactggcttc agcagagcgc agataccaaa tactgtcctt ctagtgtagc cgtagttagg    7740
```

```
ccaccacttc aagaactctg tagcaccgcc tacatacctc gctctgctaa tcctgttacc    7800
agtggctgct gccagtggcg ataagtcgtg tcttaccggg ttggactcaa gacgatagtt    7860
accggataag gcgcagcggt cgggctgaac gggggttcg tgcacacagc ccagcttgga     7920
gcgaacgacc tacaccgaac tgagatacct acagcgtgag ctatgagaaa gcgccacgct    7980
tcccgaaggg agaaaggcgg acaggtatcc ggtaagcggc agggtcggaa caggagagcg    8040
cacgagggag cttccagggg gaaacgcctg gtatctttat agtcctgtcg ggtttcgcca    8100
cctctgactt gagcgtcgat ttttgtgatg ctcgtcaggg gggcggagcc tatggaaaaa    8160
cgccagcaac gcggcctttt tacggttcct ggccttttgc tggccttttg ctcacatgtt    8220
ctttcctgcg ttatcccctg attctgtgga taaccgtatt accgcctttg agtgagctga    8280
taccgctcgc cgcagccgaa cgaccgagcg cagcgagtca gtgagcgagg aagcggaaga    8340
gcgcccaata cgcaaaccgc ctctccccgc gcgttggccg attcattaat g             8391
```